(12) United States Patent
Gilson et al.

(10) Patent No.: US 11,877,922 B2
(45) Date of Patent: *Jan. 23, 2024

(54) VASCULAR FILTER

(71) Applicant: NOVATE MEDICAL LIMITED, Dublin (IE)

(72) Inventors: Paul Gilson, Moycullen (IE); Charles Taylor, Warninglid (GB); Steven Horan, Knocknacarra (IE); Ciara Gillespie, Delgany (IE)

(73) Assignee: NOVATE MEDICAL LIMITED, Dublin (IE)

( * ) Notice: Subject to any disclaimer, the term of this patent is extended or adjusted under 35 U.S.C. 154(b) by 88 days.

This patent is subject to a terminal disclaimer.

(21) Appl. No.: 17/405,882

(22) Filed: Aug. 18, 2021

(65) Prior Publication Data

US 2022/0047372 A1 Feb. 17, 2022

Related U.S. Application Data

(63) Continuation of application No. 15/595,470, filed on May 15, 2017, now Pat. No. 11,135,049, which is a
(Continued)

(51) Int. Cl.
*A61F 2/01* (2006.01)
*A61F 2/86* (2013.01)

(52) U.S. Cl.
CPC .............. *A61F 2/0105* (2020.05); *A61F 2/86* (2013.01); *A61F 2/011* (2020.05); *A61F 2/0103* (2020.05);
(Continued)

(58) Field of Classification Search
CPC ...... A61F 2/0103; A61F 2/0105; A61F 2/011; A61F 2/86; A61F 2002/016;
(Continued)

(56) References Cited

U.S. PATENT DOCUMENTS

| | | |
|---|---|---|
| 5,344,427 A | 9/1994 | Cottenceau et al. |
| 5,350,398 A | 9/1994 | Pavcnik et al. |

(Continued)

FOREIGN PATENT DOCUMENTS

| | | |
|---|---|---|
| DE | 4030998 A1 | 4/1991 |
| DE | 102008031299 A1 | 1/2010 |

(Continued)

OTHER PUBLICATIONS

International Search Report for PCT/IE2007/00066, dated Feb. 18, 2008.

*Primary Examiner* — Jocelin C Tanner
(74) *Attorney, Agent, or Firm* — Seager, Tufte & Wickhem LLP

(57) ABSTRACT

An inferior vena cava filter (340) for use in the inferior vena cava (4) to capture thrombus (8) passing through the inferior vena cava (4) towards the heart and lungs to prevent pulmonary embolism comprises a proximal support hoop (302), a distal support hoop (312) and a plurality of support struts (303) extending between the proximal support hoop (302) and the distal support hoop (312). The filter (340) also comprises a plurality of capture arms (121) which are movable from a capturing configuration to an open configuration. The capture arms (121) are biased towards the open configuration. A biodegradable suture holds the capture arms (121) in the capturing configuration.

19 Claims, 35 Drawing Sheets

Related U.S. Application Data continuation of application No. 14/149,435, filed on Jan. 7, 2014, now abandoned, which is a continuation of application No. 13/426,933, filed on Mar. 22, 2012, now Pat. No. 8,647,360, which is a continuation of application No. 11/822,680, filed on Jul. 9, 2007, now Pat. No. 8,162,970.

(60) Provisional application No. 60/831,674, filed on Jul. 19, 2006.

(52) U.S. Cl.
CPC . *A61F 2002/016* (2013.01); *A61F 2210/0004* (2013.01); *A61F 2230/005* (2013.01); *A61F 2230/0006* (2013.01); *A61F 2230/008* (2013.01); *A61F 2230/0021* (2013.01); *A61F 2230/0058* (2013.01); *A61F 2230/0067* (2013.01); *A61F 2230/0069* (2013.01); *A61F 2230/0091* (2013.01)

(58) Field of Classification Search
CPC ...... A61F 2210/0004; A61F 2230/0006; A61F 2230/0021; A61F 2230/005; A61F 2230/0058; A61F 2230/0067; A61F 2230/0069; A61F 2230/008; A61F 2230/0091; B01D 61/00
See application file for complete search history.

(56) References Cited

U.S. PATENT DOCUMENTS

| | | | |
|---|---|---|---|
| 5,375,612 | A | 12/1994 | Cottenceau et al. |
| 5,383,887 | A * | 1/1995 | Nadal .................. A61F 2/01 606/198 |
| 5,634,942 | A | 6/1997 | Chevillon et al. |
| 5,725,550 | A | 3/1998 | Nadal |
| 5,800,525 | A | 9/1998 | Bachinski et al. |
| 5,853,420 | A | 12/1998 | Chevillon et al. |
| 5,968,071 | A | 10/1999 | Chevillon et al. |
| 6,013,093 | A | 1/2000 | Nott et al. |
| 6,193,739 | B1 | 2/2001 | Chevillon et al. |
| 6,214,025 | B1 | 4/2001 | Thistle et al. |
| 6,241,746 | B1 | 6/2001 | Bosma et al. |
| 6,248,128 | B1 | 6/2001 | Berry et al. |
| 6,267,776 | B1 | 7/2001 | O'Connell |
| 6,312,461 | B1 | 11/2001 | Unsworth et al. |
| 6,482,227 | B1 | 11/2002 | Solovay |
| 6,517,559 | B1 * | 2/2003 | O'Connell ............ A61F 2/0103 606/108 |
| 6,527,962 | B1 | 3/2003 | Nadal |
| 6,582,447 | B1 * | 6/2003 | Patel .................. A61B 17/221 606/200 |
| 6,605,111 | B2 | 8/2003 | Bose et al. |
| 6,652,558 | B2 | 11/2003 | Patel et al. |
| 6,666,882 | B1 | 12/2003 | Bose et al. |
| 6,669,721 | B1 | 12/2003 | Bose et al. |
| 6,852,076 | B2 | 2/2005 | Nikolic et al. |
| 6,881,218 | B2 * | 4/2005 | Beyer .................. A61F 2/0103 606/198 |
| 6,932,832 | B2 | 8/2005 | Patel et al. |
| 6,966,923 | B2 | 11/2005 | Gittings |
| 6,972,025 | B2 | 12/2005 | Wasdyke |
| 7,001,424 | B2 | 2/2006 | Patel et al. |
| 7,094,248 | B2 | 8/2006 | Bachinski et al. |
| 7,261,731 | B2 | 8/2007 | Patel et al. |
| 7,279,007 | B2 | 10/2007 | Nikolic et al. |
| 7,534,251 | B2 | 5/2009 | Wasdyke |
| 8,057,507 | B2 | 11/2011 | Horan et al. |
| 8,162,970 | B2 * | 4/2012 | Gilson .................. A61F 2/0105 606/200 |
| 8,647,360 | B2 * | 2/2014 | Gilson .................. A61F 2/0105 606/200 |
| 8,668,713 | B2 | 3/2014 | Horan et al. |
| 11,135,049 | B2 * | 10/2021 | Gilson ...................... A61F 2/86 |
| 2001/0044652 | A1 * | 11/2001 | Moore .................... A61F 2/915 623/1.16 |
| 2002/0099439 | A1 | 7/2002 | Schwartz et al. |
| 2003/0040771 | A1 | 2/2003 | Hyodoh et al. |
| 2003/0040772 | A1 * | 2/2003 | Hyodoh .................. A61F 2/90 606/200 |
| 2003/0120303 | A1 | 6/2003 | Boyle et al. |
| 2003/0144688 | A1 | 7/2003 | Brady et al. |
| 2003/0176888 | A1 | 9/2003 | O'Connell |
| 2003/0208227 | A1 | 11/2003 | Thomas |
| 2004/0019374 | A1 | 1/2004 | Hojeibane et al. |
| 2004/0034407 | A1 * | 2/2004 | Sherry .................... A61F 2/848 623/1.15 |
| 2004/0220611 | A1 | 11/2004 | Ogle |
| 2005/0096735 | A1 | 5/2005 | Hojeibane et al. |
| 2005/0107822 | A1 | 5/2005 | Wasdyke |
| 2005/0222604 | A1 | 10/2005 | Schaeffer |
| 2005/0234504 | A1 | 10/2005 | Wasdyke |
| 2006/0025852 | A1 | 2/2006 | Armstrong et al. |
| 2007/0032816 | A1 | 2/2007 | O'Connell et al. |
| 2007/0112372 | A1 | 5/2007 | Sosnowski et al. |
| 2007/0203571 | A1 | 8/2007 | Kaplan et al. |
| 2008/0188887 | A1 | 8/2008 | Batiste |
| 2008/0208245 | A1 | 8/2008 | Hoffman |
| 2009/0105747 | A1 | 4/2009 | Chanduszko et al. |
| 2010/0185227 | A1 | 7/2010 | Horan et al. |
| 2010/0185229 | A1 | 7/2010 | Horan et al. |
| 2010/0185230 | A1 | 7/2010 | Horan et al. |
| 2010/0228281 | A1 | 9/2010 | Gilson et al. |
| 2012/0029552 | A1 | 2/2012 | Horan et al. |

FOREIGN PATENT DOCUMENTS

| | | |
|---|---|---|
| EP | 0565395 A1 | 10/1993 |
| EP | 0582493 A1 | 2/1994 |
| EP | 0599635 A1 | 5/1994 |
| EP | 0605276 A1 | 7/1994 |
| EP | 0655228 A1 | 5/1995 |
| EP | 0678284 A1 | 10/1995 |
| EP | 0737451 A1 | 10/1996 |
| EP | 0759287 A1 | 2/1997 |
| EP | 0864301 A1 | 9/1998 |
| EP | 0935975 A1 | 8/1999 |
| EP | 1103233 A1 | 5/2001 |
| EP | 1258228 A1 | 11/2002 |
| EP | 1616530 A1 | 1/2006 |
| FR | 2718950 A1 | 10/1995 |
| FR | 2764503 A1 | 12/1998 |
| FR | 2814670 A1 | 4/2002 |
| WO | 9638101 A1 | 12/1996 |
| WO | 0012004 A2 | 3/2000 |
| WO | 0056390 A1 | 9/2000 |
| WO | 0066031 A1 | 11/2000 |
| WO | 0162184 A2 | 8/2001 |
| WO | 0222048 A1 | 3/2002 |
| WO | 03092537 A2 | 11/2003 |
| WO | 2004016192 A2 | 2/2004 |
| WO | 2006020425 A1 | 2/2006 |
| WO | 2006074163 A2 | 7/2006 |
| WO | 2006116636 A1 | 11/2006 |
| WO | 2008010197 A2 | 1/2008 |

* cited by examiner

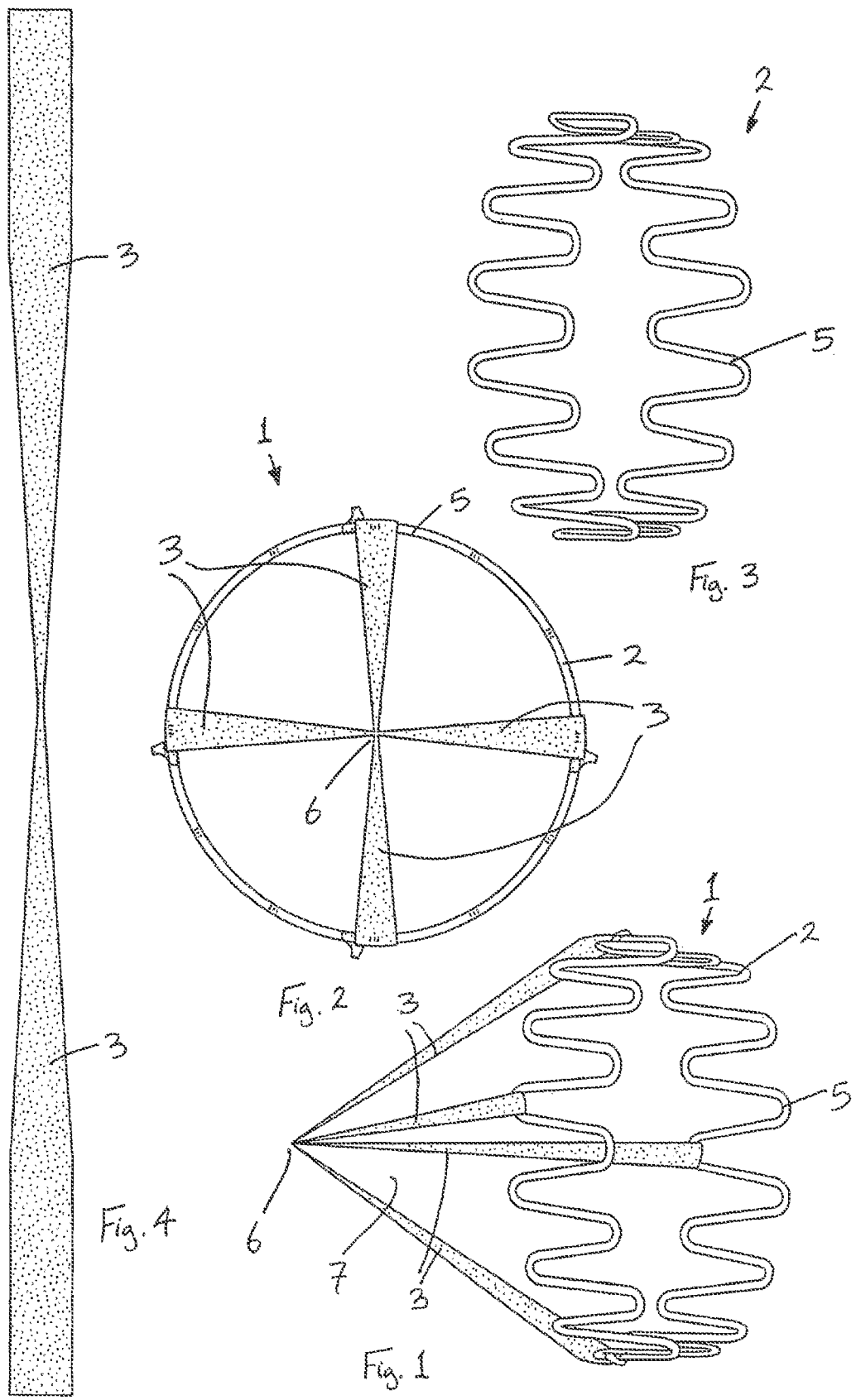

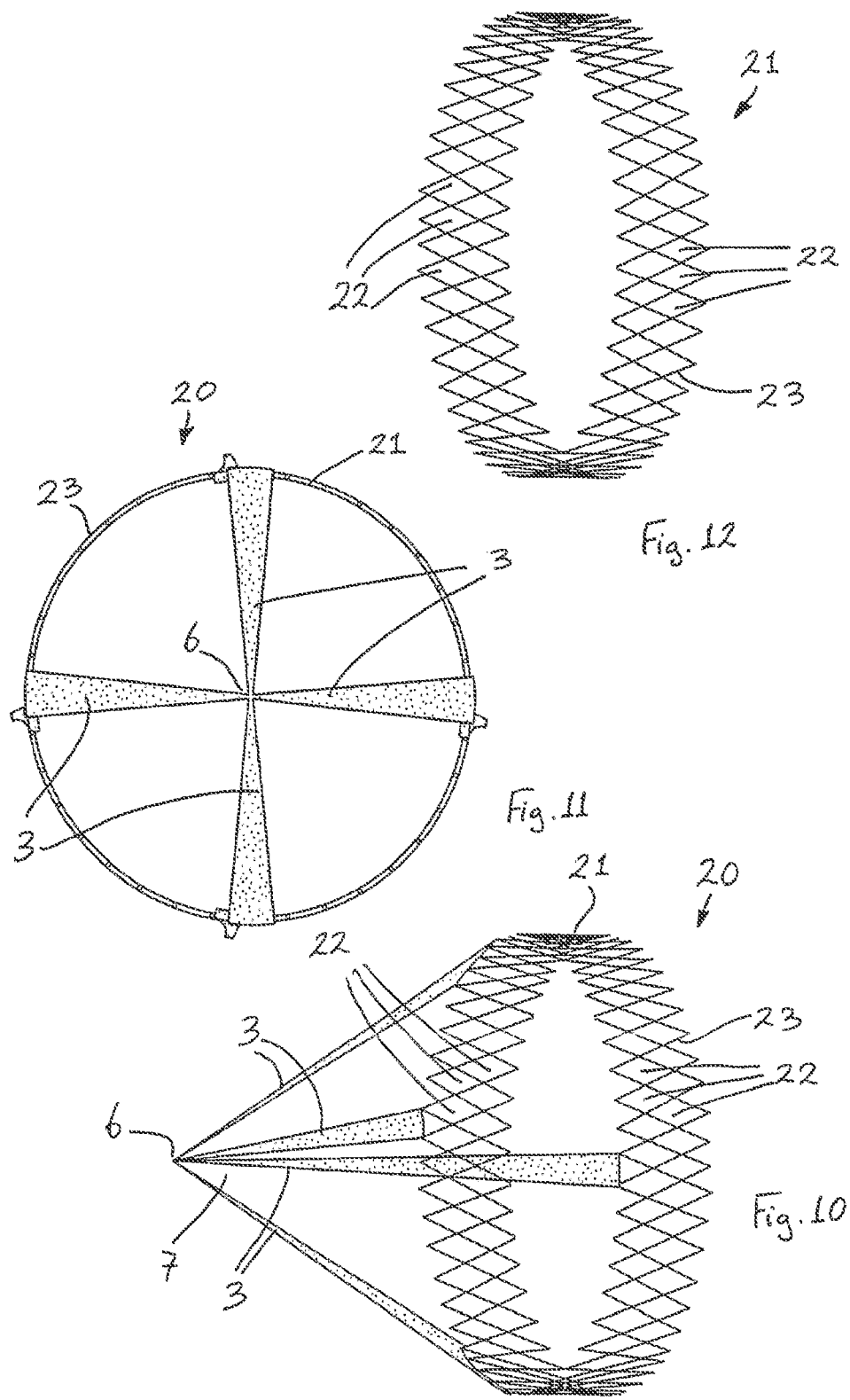

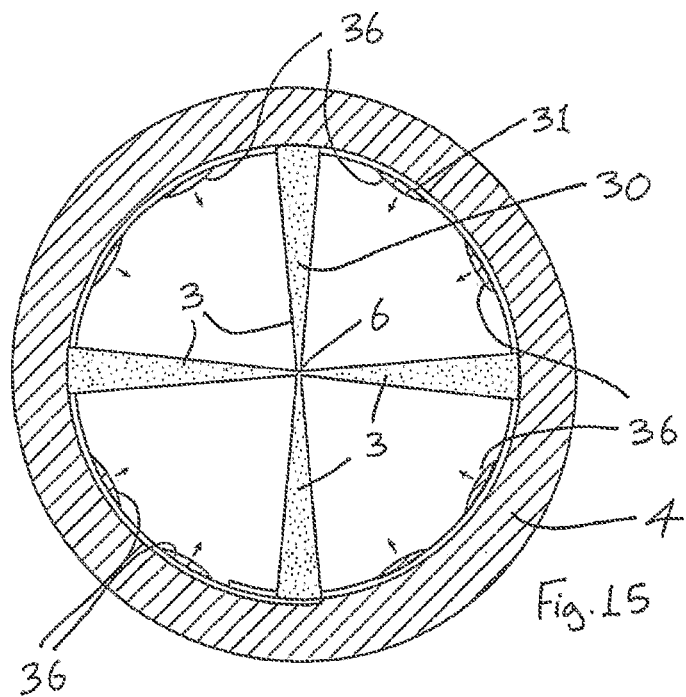
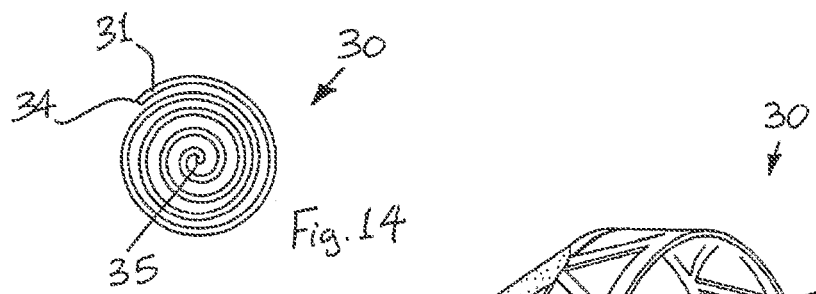
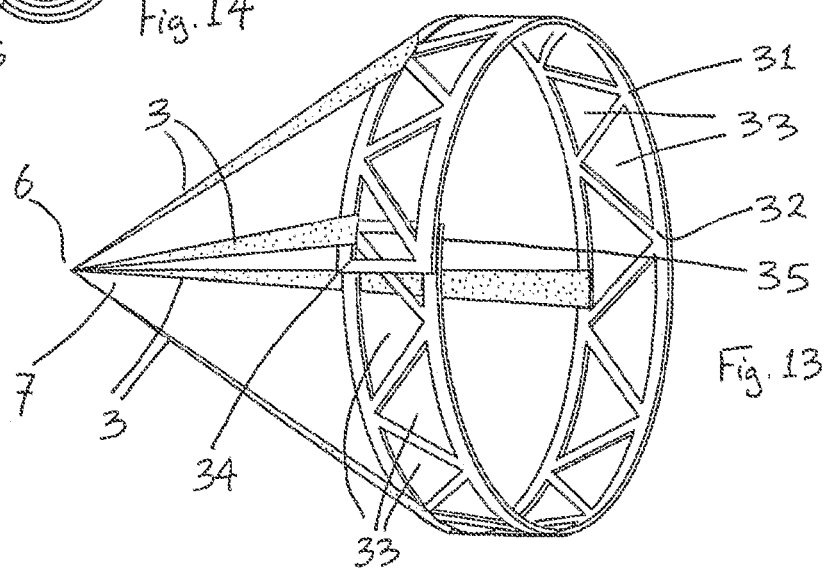

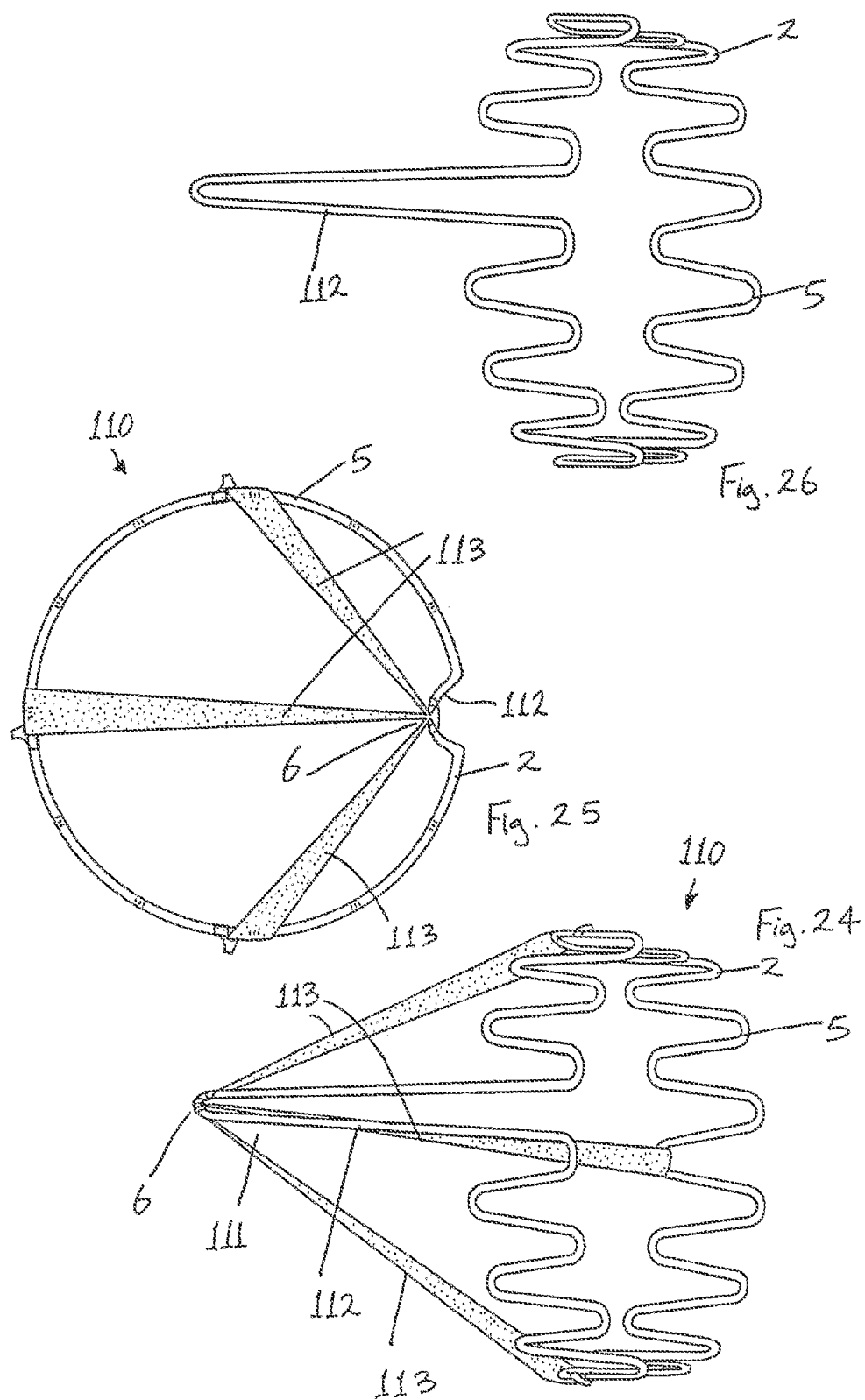

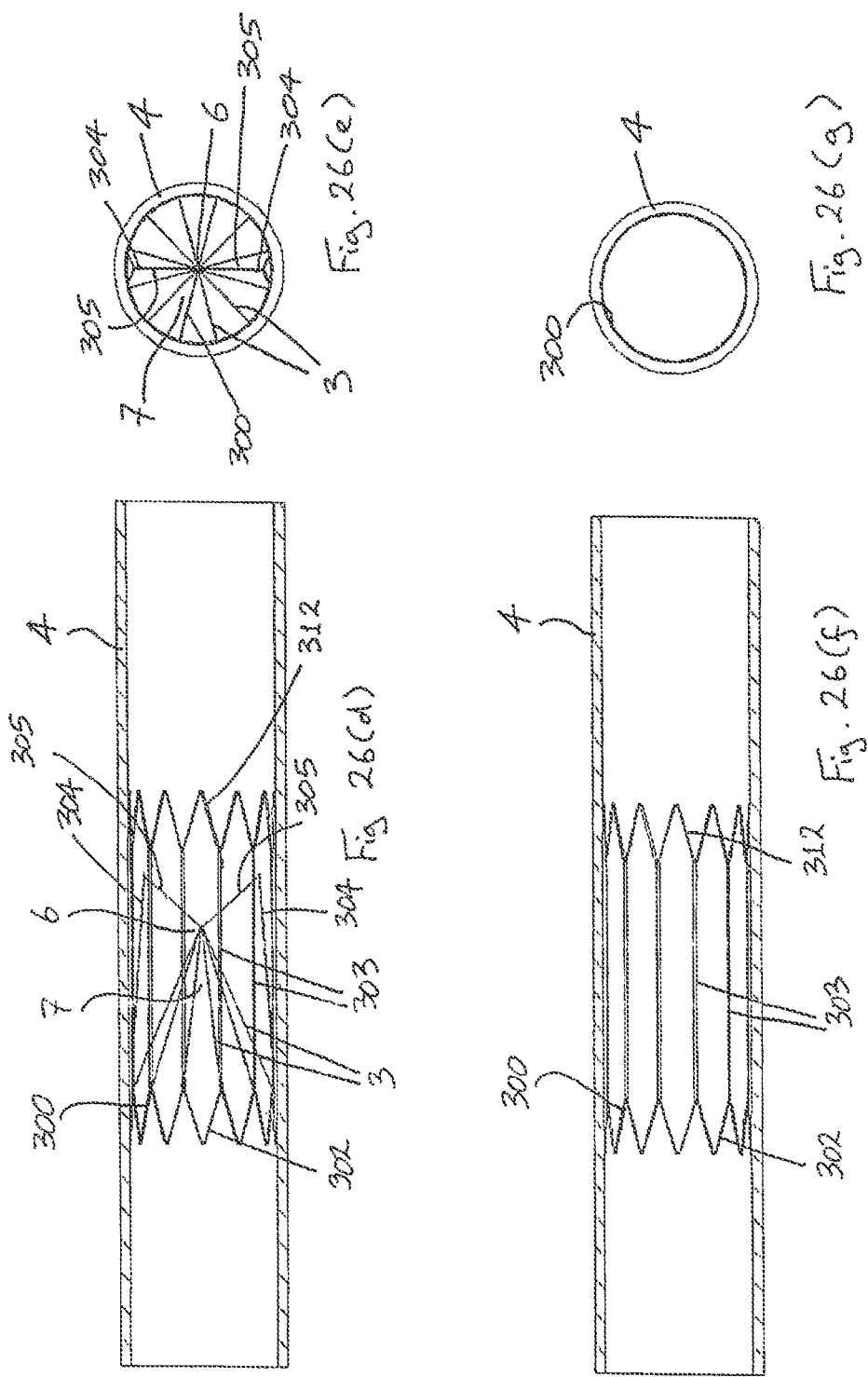

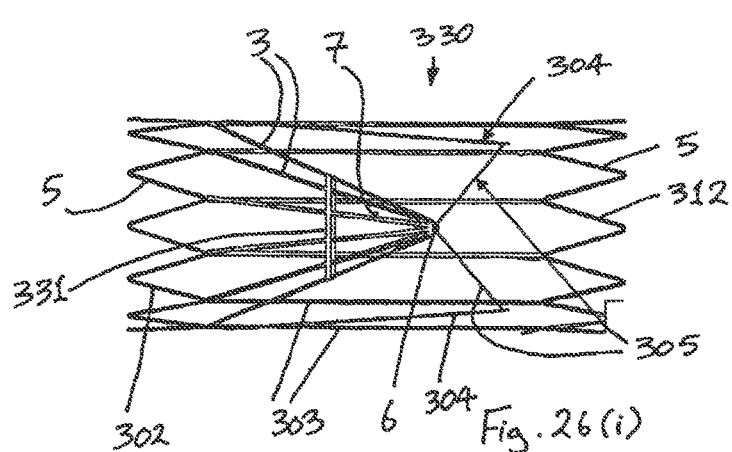
Fig. 26(i)
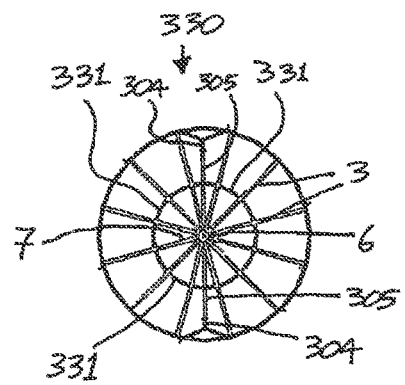
Fig. 26(j)
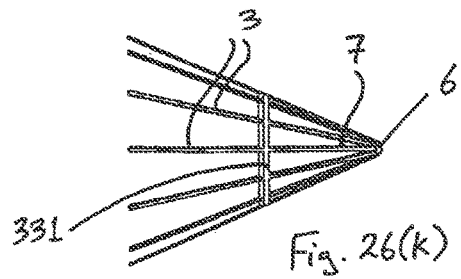
Fig. 26(k)
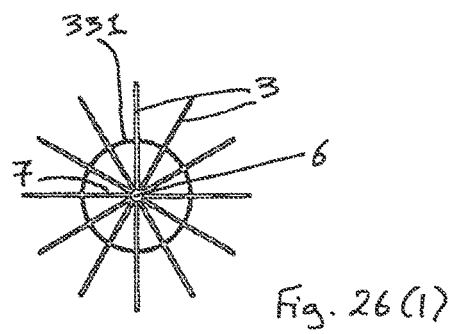
Fig. 26(l)
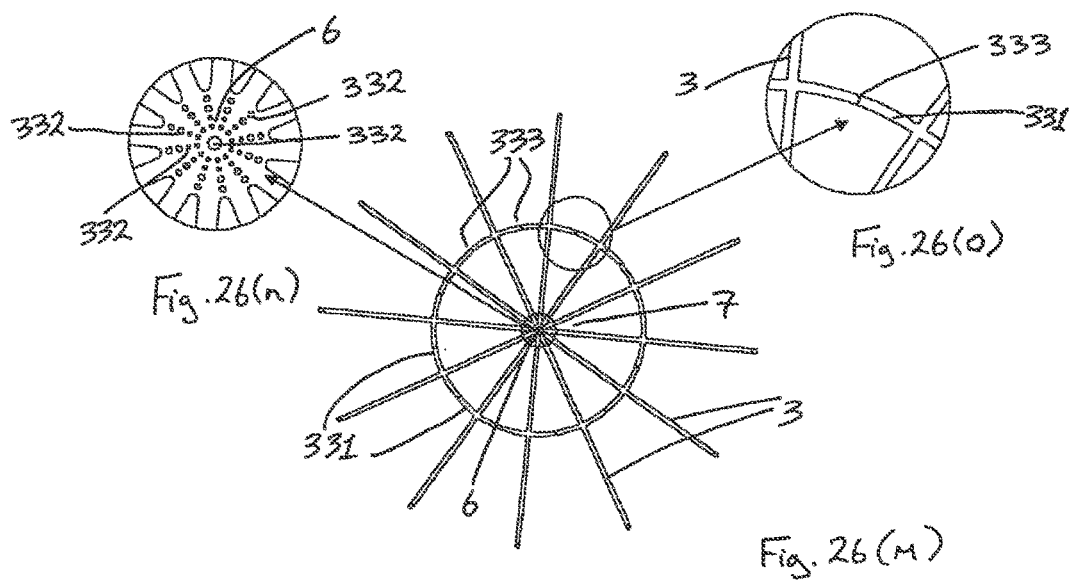
Fig. 26(n)
Fig. 26(o)
Fig. 26(m)

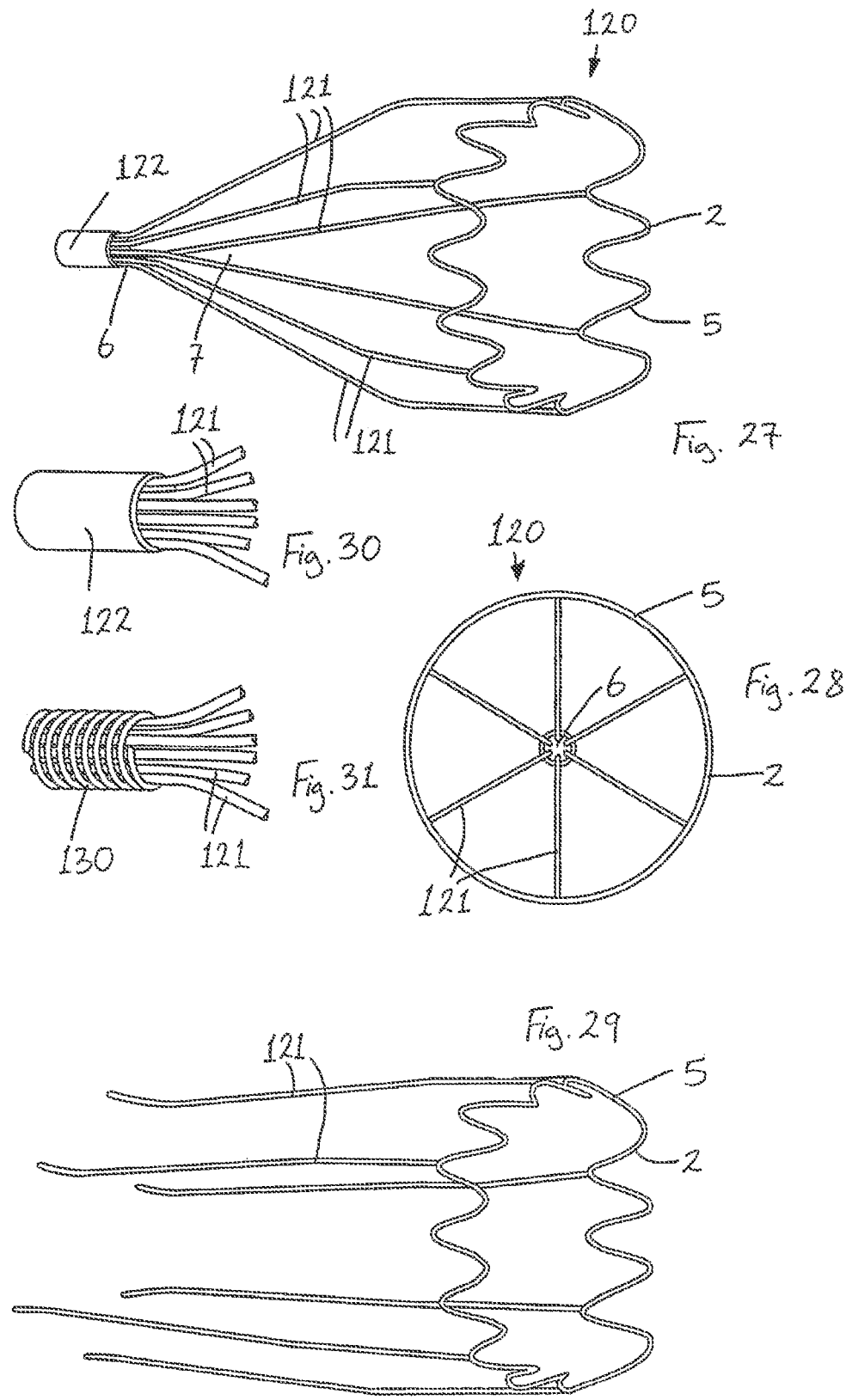

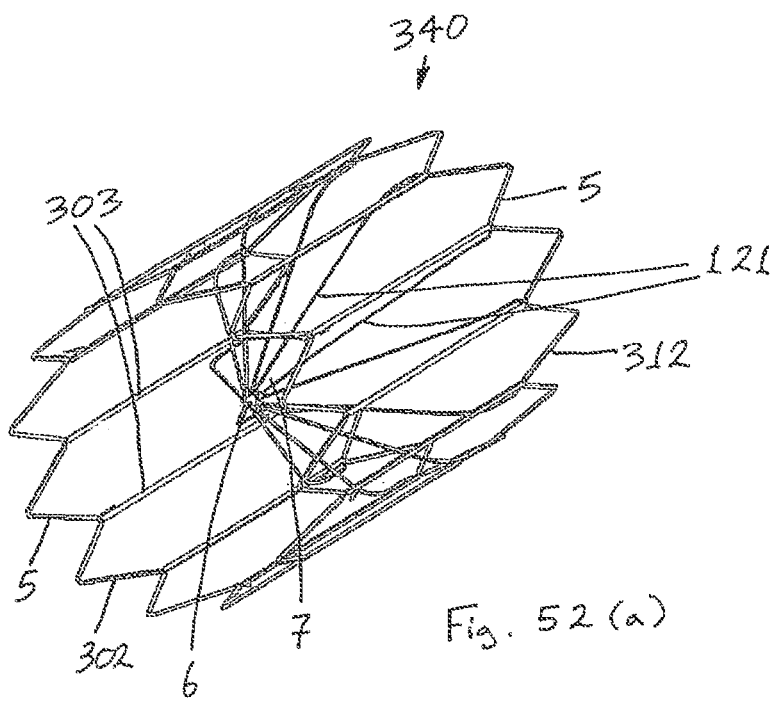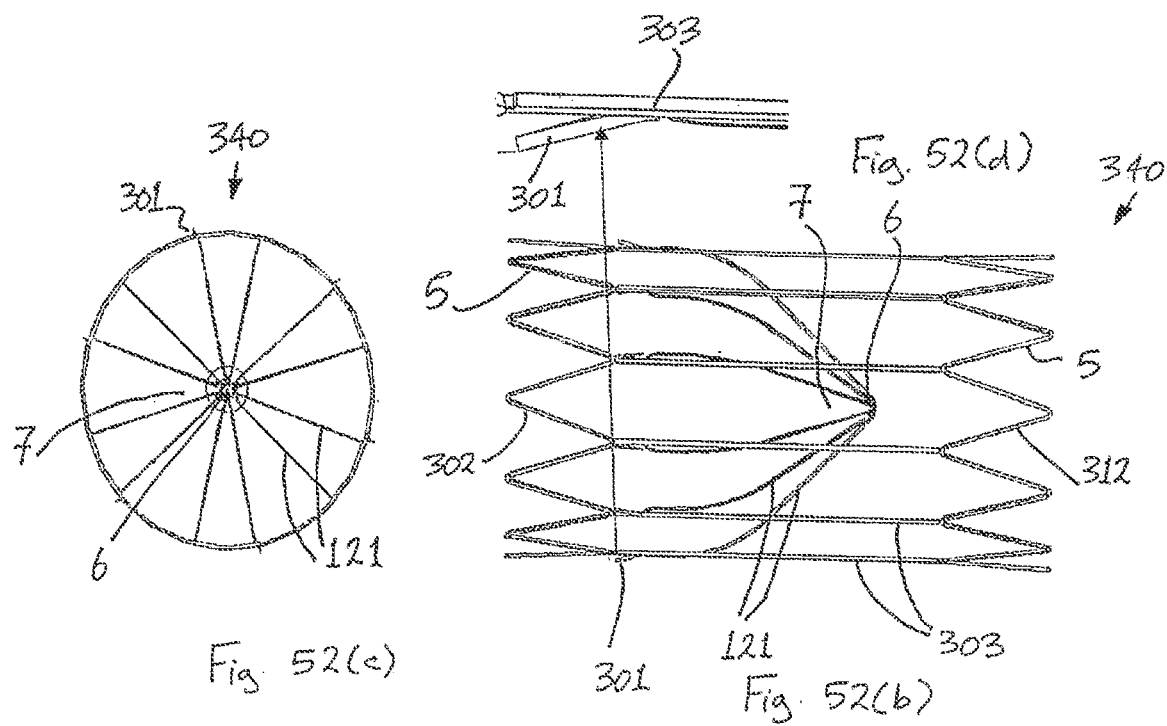

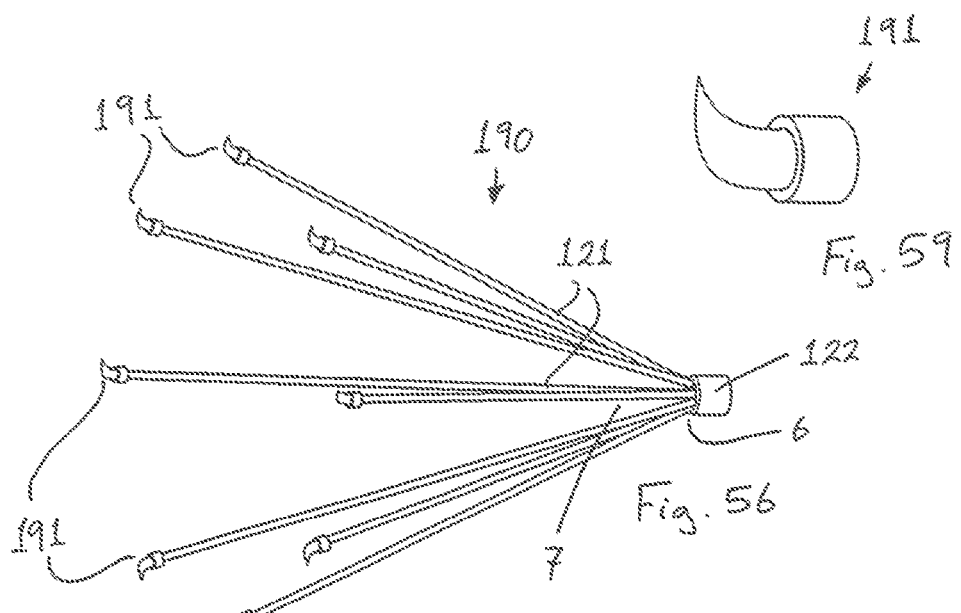
Fig. 56
Fig. 59
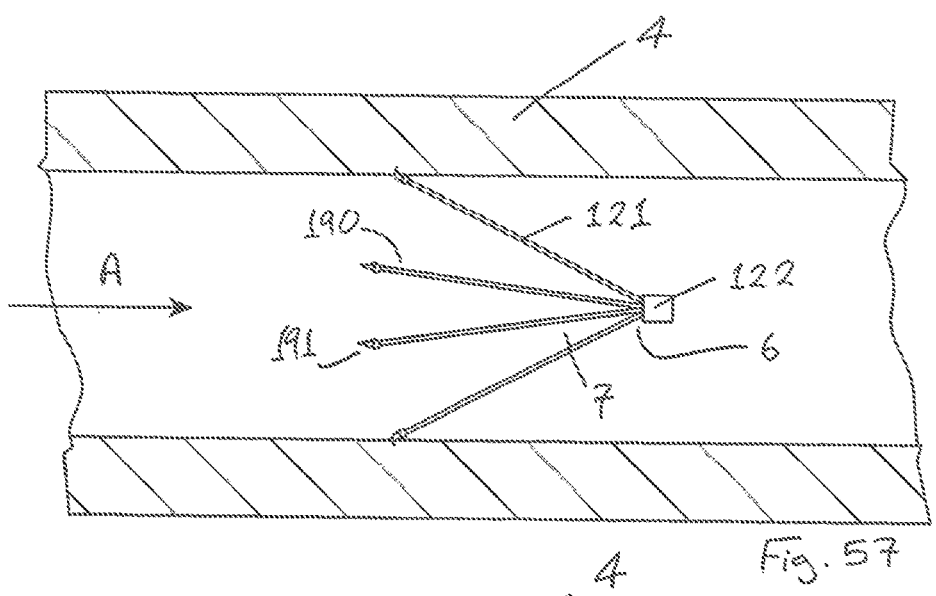
Fig. 57
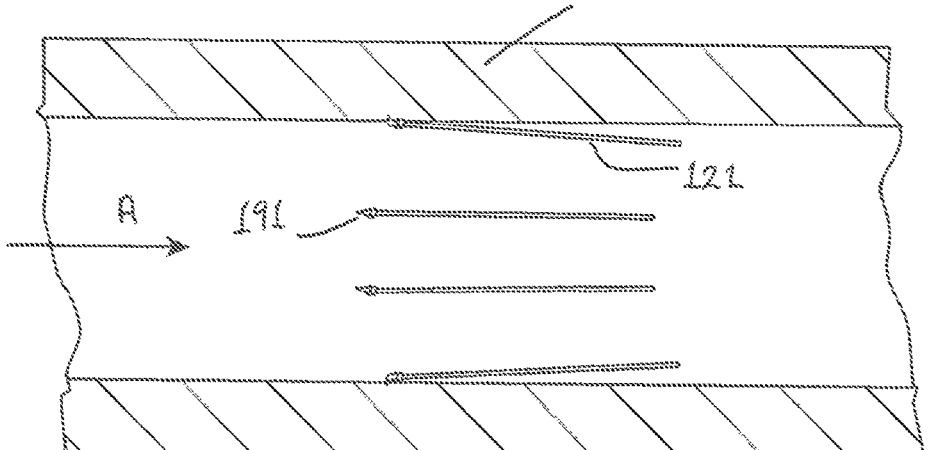
Fig. 58

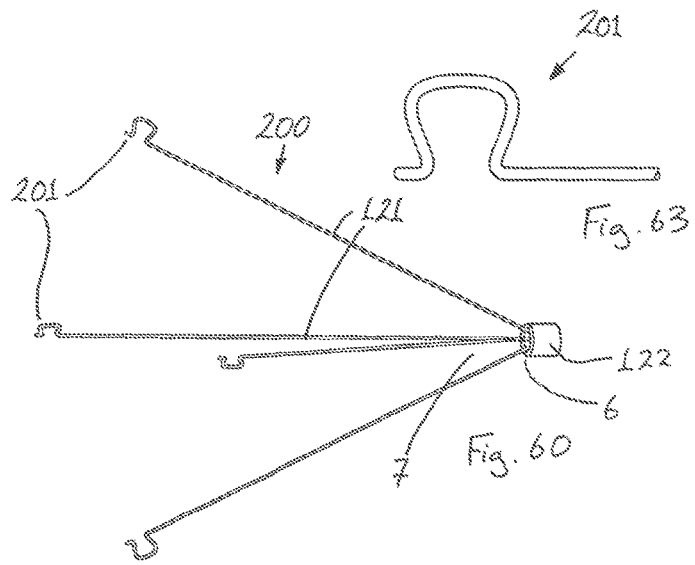
Fig. 63
Fig. 60
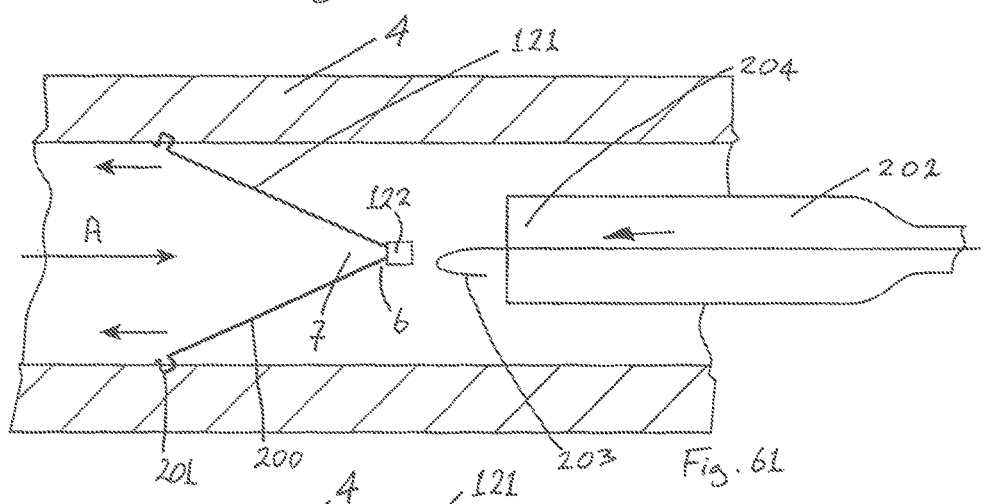
Fig. 61
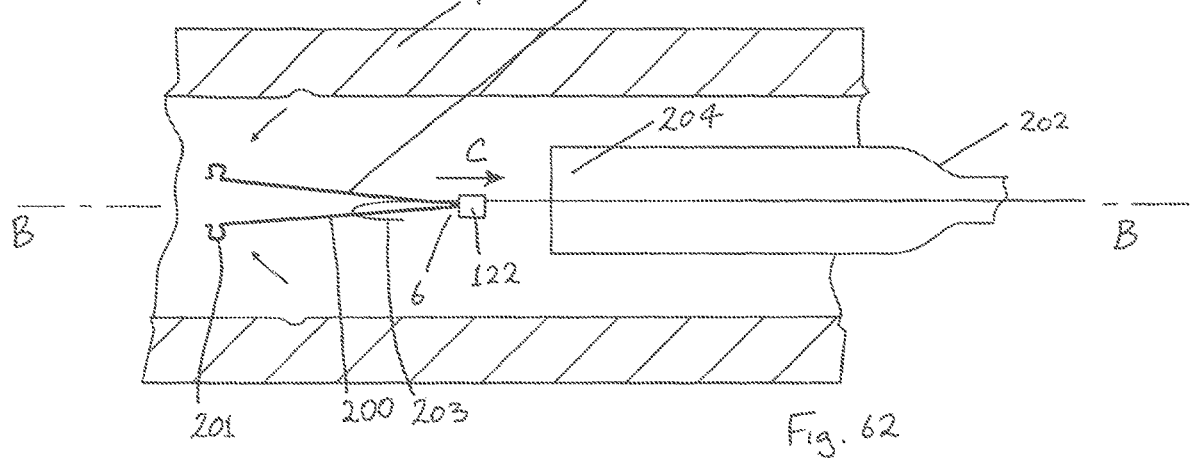
Fig. 62

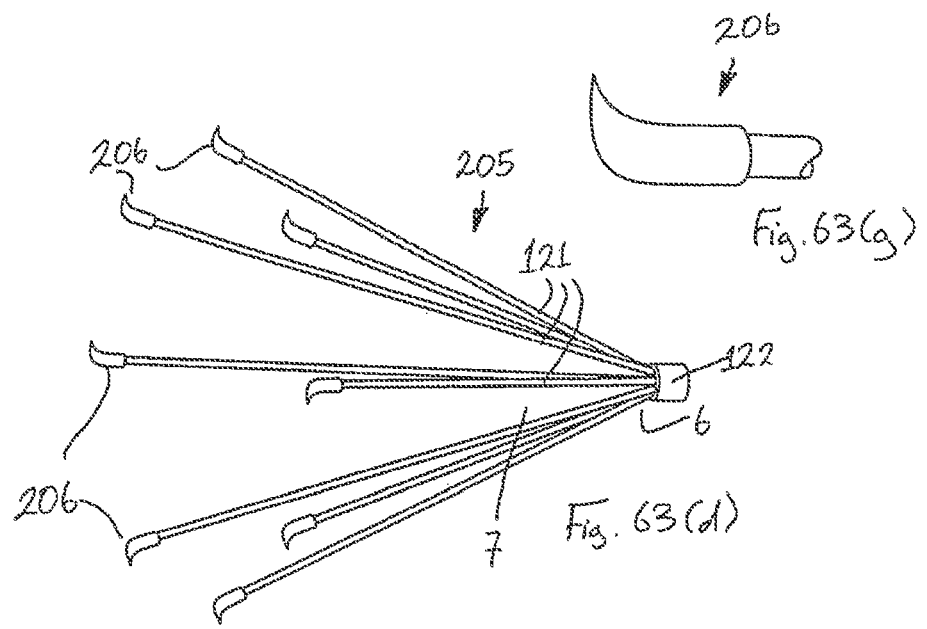
Fig. 63(g)
Fig. 63(d)
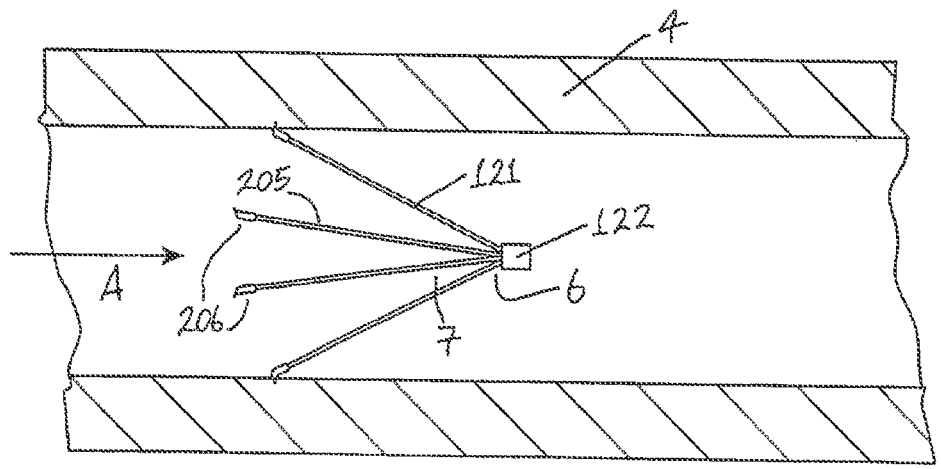
Fig. 63(e)
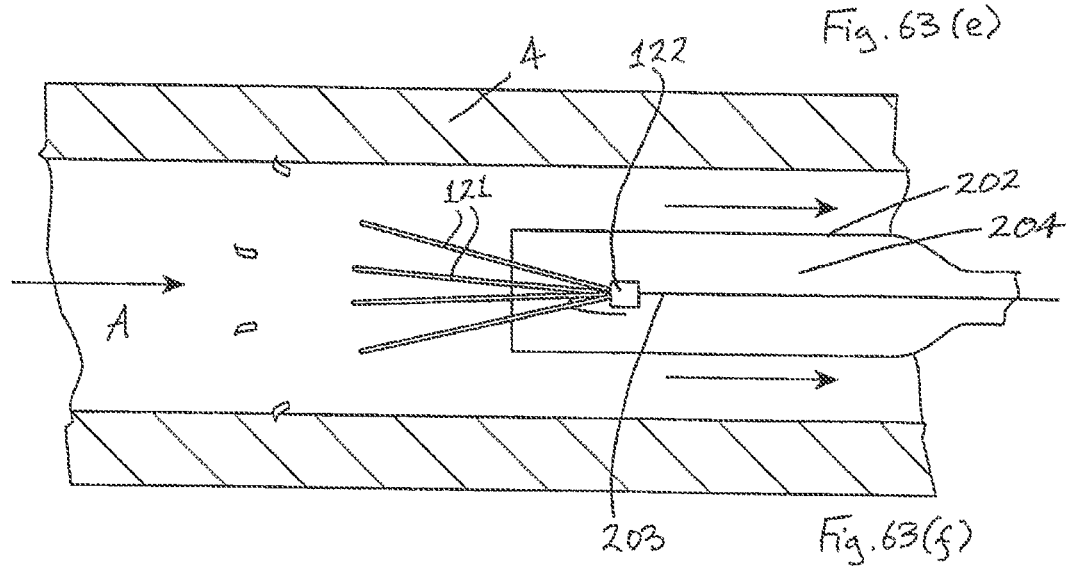
Fig. 63(f)

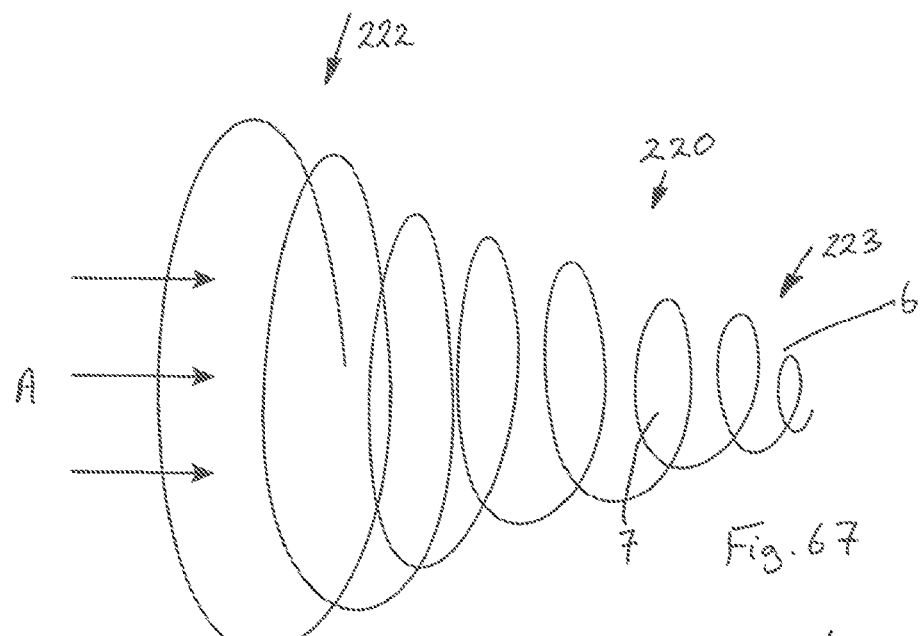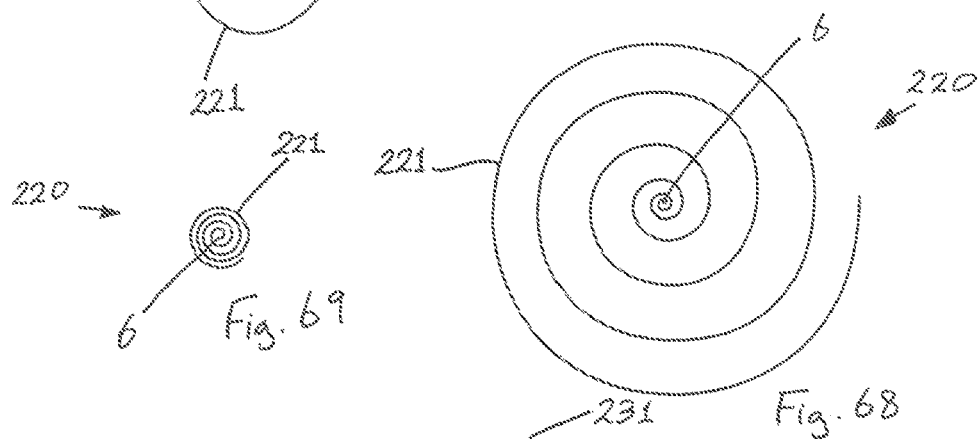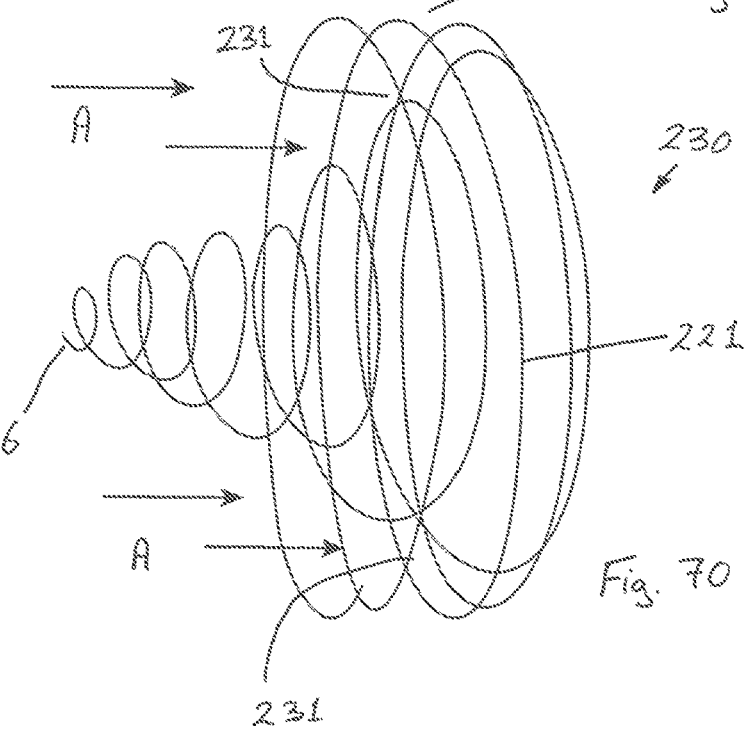

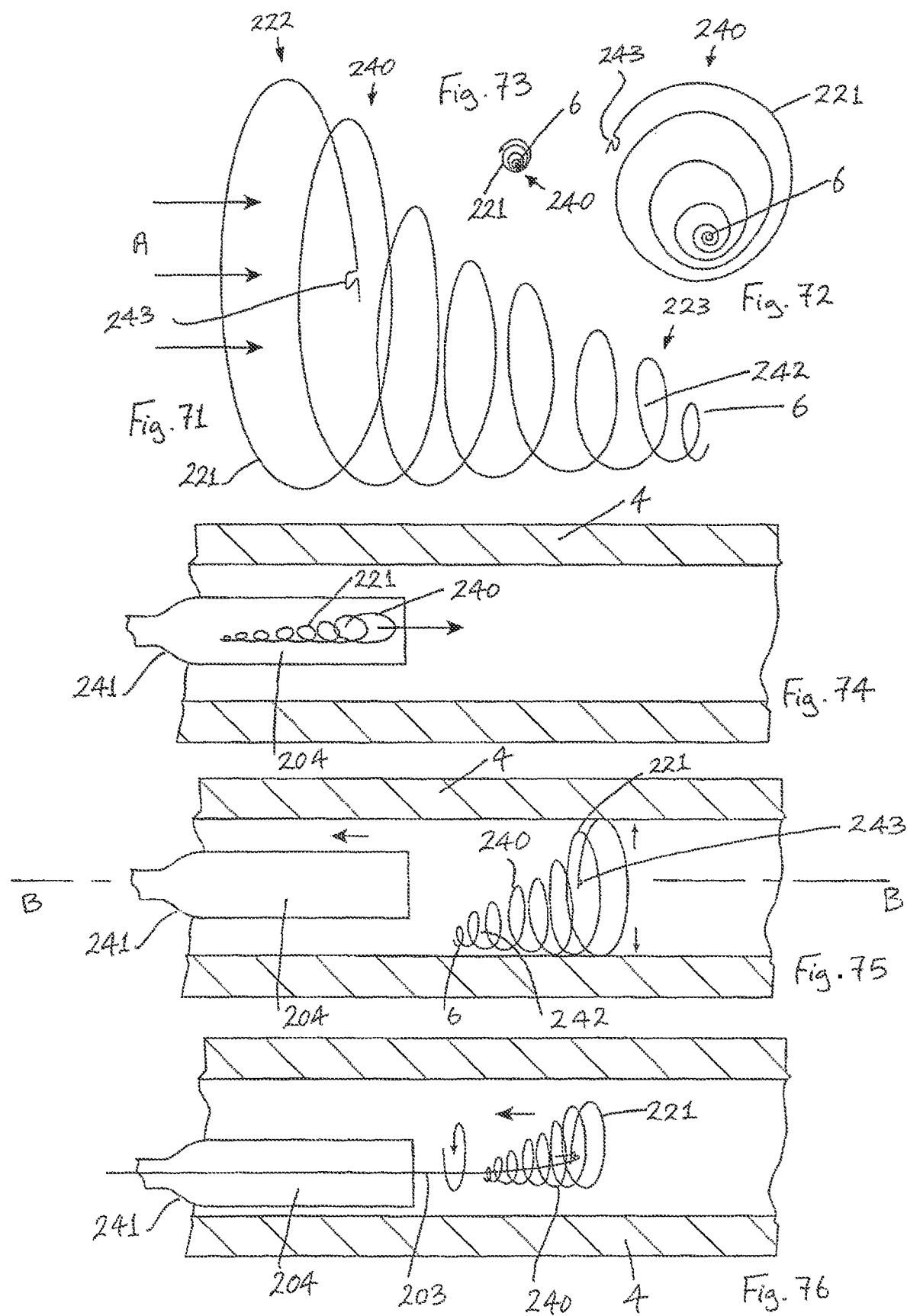

VASCULAR FILTER

CROSS-REFERENCE TO RELATED APPLICATIONS

This application is a continuation of U.S. application Ser. No. 15/595,470, filed May 15, 2017, which is a continuation of U.S. application Ser. No. 14/149,435, filed Jan. 7, 2014, which is a continuation of U.S. application Ser. No. 13/426,933, filed Mar. 22, 2012, which is a continuation of U.S. application Ser. No. 11/822,680, filed Jul. 9, 2007, which claims the benefit of priority of U.S. Provisional Application No. 60/831,674, filed Jul. 19, 2006. The entirety of these disclosures of which are hereby incorporated by reference.

This invention relates to a vascular filter. In one particular embodiment this invention relates to an inferior vena cava filter.

It is known to implant a vena cava filter in the vena cava to prevent thrombus entering the right atrium. They have been in use clinically for a number or years. The use of filters implanted in the inferior vena cava is for the prevention of pulmonary embolism in high-risk patients.

Deep vein thrombosis (DVT) and pulmonary embolism (PE) are common medical conditions that contribute substantially to individual patient morbidity and mortality as well as global healthcare costs. DVT develops within the deep veins of the lower extremities but also can involve or arise solely from the veins in the pelvis or the upper extremities. When blood clots float from a large vein in the lower body through the vena cava to the heart and lungs they may cause pulmonary embolism (PE). Because DVT and PE share a common pathophysiology and frequently occur together they are currently being perceived as two points on the continuum of a single disease process identified as venous thromboembolism (VTE).

Experts estimate that pulmonary embolism (PE) affects over 1.2 million people in the US and Europe every year. The highest recognized incidence of PE occurs in hospitalized patients, with 60% of hospitalized patients having had a PE. However, the diagnosis of PE is missed in approximately 70% of those patients. PE is the third leading acute cardiovascular cause of death in the developed world accounting for approximately 10% of in-hospital deaths. In spite of the potentially disastrous outcomes, not all surgical patients receive appropriate protection. This is in part due to the fact that current treatments are not ideal. There are two broad categories of vena cava filters: permanent and retrievable. Permanently implanted devices can migrate and their clinical use is not preferred in younger patients. Retrievable filters can be notoriously difficult to remove and the addition intervention poses risks to patients.

Common clinical risk factors for DVT and PE include age older than 50 years, prolonged immobilization because of illness, travel or surgery, oestrogen therapy, pregnancy and malignancy among others. A genetic predisposition has also been suggested.

Candidates for inferior vena cava (IVC) filter placement are typically evaluated for the presence of lower-extremity DVT and/or PE. Imaging methods used to document the presence of lower-extremity DVT include ultra sound and peripheral venography. PE can also be diagnosed by using nuclear medicine ventilation-perfusion scans. Although pulmonary arteriography remains today's criterion standard for computed tomography (CT) to evaluate patients in whom PE is suspected. Magnetic resonance angiography (MRA) of the pulmonary vasculature is also performed an alternative diagnostic imaging technique.

Inferior vena cavography is currently the modality used most commonly to assess the inferior vena cava (IVC). Access to the IVC is typically achieved via a left or right femoral vein or via the right internal jugular vein. Ultrasound may be used to guide the puncture.

Although the indications for IVC filter placement have expanded over the years, a DVT or PE in a patient with a contraindication for anticoagulation therapy remains the most frequent indication, accounting for 65% or patients undergoing IVC filter placement. Insertion of a vena cava filter is indicated for patients who:

Cannot receive medications that can dissolve the clot

Have a thrombus in a deeply situated vein

Experience complication of anticoagulation therapy such as bleeding.

Experience failure of anticoagulation therapy to prevent pulmonary embolism

Have an embolus in the lungs removed (pulmonary embolectomy)

Have a recurrent embolism while receiving adequate medications

Have significant bleeding complications during anticoagulation

The inferior vena cava (IVC) is the largest venous structure in the body. It drains the venous return from the lower extremities, pelvis, and abdomen into the right atrium. Before filter placement, an inferior vena cavogram is obtained to assess caval diameter and patency, the extent of thrombus and to understand the presence of any venous anomalies.

Filters can be placed by either a femoral or jugular approach. The basic principle lot femoral insertion is to choose the side that has patent and preferably thrombus-free veins. Right femoral puncture is preferable because there is less angulation in the iliac veins. A careful left femoral approach may be successful if a right-sided puncture in contraindicated. A jugular approach can be used when there is inferior vena cava or bilateral iliofemoral thrombosis. For the femoral approach, the common femoral vein is punctured, while for the jugular approach, the puncture site is at the internal jugular vein. Another inferior vena cavogram is performed after filter placement to check the position and stability of the filter.

The invention is aimed towards providing an improved vascular filter.

STATEMENTS OF INVENTION

According to the invention there is provided a vascular further comprising:

one or more capture members for capturing thrombus passing through a blood vessel; and one or more support members for supporting the one or more capture members relative to a wall of the blood vessel.

By capturing the thrombus, the filter prevents the thrombus from passing to the heart or lungs, which may cause pulmonary embolism.

By supporting the capture members this ensures that the capture members are maintained the desired location in the blood vessel.

In one embodiment of the invention the support member is configured to extend circumferentially around a wall of a blood vessel. The support member may extend circumferentially in a wave pattern. The support member may extend circumferentially in a zigzag pattern. The support member may extend circumferentially in a crown patter. The support member may extend circumferentially in a sinusoid pattern.

The wave/sinusoid pattern of the support member facilitates collapse of the support member for ease of delivery and/or retrieval through the blood vessel. The support member may be configured to extend longitudinally along a wall of a blood vessel. A distal end of the support member may be located distally of a distal end of the capture member. A proximal end of the support member may be located proximally of a proximal end of the capture member. The filter may comprise a first support member configured to extend circumferentially around a wall of a blood vessel, a second support member configured to extend circumferentially around the wall of the blood vessel, and a third support member configured to extend longitudinally along the wall of the blood vessel. The third support member may connect the first support member to the second support member. The first support member, the second support member and the third support member may be formed integrally. The first support member may be provided at the proximal end of the filter. The second support member may be provided at the distal end of the filter.

In one case the rapport member comprises a body portion and one or more openings in the body portion. The openings in the a support member facilitate tissue ingrowth. A drug coating may be added to the structure to manage the tissue response at and near site of implant. This may take the form of a polymer or metal coating containing the pharmaceutical that releases the drug in a controlled manner or a separate or integral sleeve that covers the entire device and is implanted between the device and the vena cava. This sleeve may be bio-degradable or bio-resorbable. The support member may comprise a mesh. The support member easy comprise a trellis.

In another embodiment the support member comprises an anchor member. The anchor member may be configured to be embedded at least partially into a wall of a blood vessel. The anchor member may comprise a barb element. The anchor member may be configured to be removed from a wall of blood vessel. The anchor member may be configured to be removed from a wall of a blood vessel upon application of a removed force in a direction substantially parallel to the longitudinal axis of the blood vessel. At least part of the anchor member may be biodegradable and/or bioabsorbable.

In another case at least part of the support member is biodegradable and/or bioabsorbable.

In one embodiment the support member is movable between a delivery configuration and a deployed configuration. The support member may be collapsed in the delivery configuration. The support member may be expanded in the deployed configuration. The support member may be biased towards the deployed configuration.

In one case at least part of the capture member is biodegradable and/or bioabsorbable. All of the capture member may be biodegradable and/or bioabsorbable.

In another case the capture member comprises one or more predetermined failure points. This enables controlled biodegrading/bioabsorbing of the capture member. The capture member may have a designed in reduced tensile strength failure point. The capture member may comprise one or more openings through a wall of the capture member at the failure point.

In one embodiment the filter comprises one or more linking members to link one capture member to an adjacent capture member. At least part of the linking member may be biodegradable and/or bioabsorbable.

In another embodiment the capture member is attached to the support member. The capture member may be attached to the support member in a snap-fit arrangement. Part of the capture member may be wrapped around the support member. The capture member may be provided integral with the support member.

In one case the capture member is movable between a capturing configuration and an open configuration. The capture members may remain in the capturing configuration while there exists a risk of thrombus. When the risk of thrombus passes, the capture members may then move to the open configuration. Thus it may not be necessary to retrieve the filter from the blood vessel. The capture member may be biased towards the open configuration. The filter may comprise a holder member to hold the capture member in the capturing configuration. At least part of the holder member may be biodegradable and/or bioabsorbable. The holder member may comprise a tube around at least part of the capture member. The holder member may comprise a tube around at least part of the capture member. The holder member may be permanent, removable or bioabsorbable. The holder member may extend through an opening in the capture member. The holder member may comprise a suture. The holder member may comprise one or more predetermined failure points. This enables controlled biodegrading/bioabsorbing of the holder member. The holder member may have a reduced tensile strength at the failure point. The holder member may comprise one or more openings through a wall of the holder member at the failure point.

In another embodiment the capture member extends towards an apex. In the capturing configuration, the capture member may extend towards the apex. The apex may be substantially in-line with a longitudinal axis extending through the centre of a blood vessel. The apex may be substantially offset from a longitudinal axis extending through the centre of a blood vessel. The offset apex may result in the captured thrombus being offset from the centre of the blood vessel. Thus blood flow through the blood vessel may be enhanced. Two or more of the capture member may engage one another at the apex. An end of a first capture member may be configured to nest with an end of a second capture member at the apex. The capture member may extend in the direction of blood flow through a blood vessel. The capture member may extend in a direction opposite to the direction of blood flow through a blood vessel. The capture member may extend in a spiral towards the apex. At least part of the capture member may extend in a curve. The convex portion of the curve, may face radially outwardly. The concave portion of the curve may face radially outwardly.

In another embodiment the capture member defines a capture region within which thrombus may be captured. In the capturing configuration, the capture member may define the capture region. The capture region may be configured to be located in the region of the centre of a blood vessel. The capture region may be configured to be located in the region of a wall of a blood-vessel. By locating the capture region in the region of the blood vessel wall, this may enhance blood flow through the blood vessel. The capture region may be substantially annular shaped. The capture region may be substantially conically shaped. The capture region may be substantially cylindrically shaped.

In one case the capture member is movable between a delivery configuration and a deployed configuration. The capture member may be collapsed in the delivery configuration. The capture member may be expanded in the deployed configuration. The capture member may be biased towards the deployed configuration.

In another case the filter comprises one or more tensioning members to tension the capture member. The tensioning member may be movable between a capturing configuration and an open configuration. The tensioning member may be biased towards the open configuration. The filter may comprise one or more connecting members to connect the tensioning member to the capture member. At least part of the connecting member may be biodegradable and/or bio-absorbable.

In another embodiment the filter comprises one or more balance members extending in the opposite direction to the capture member. In a filter configuration the one or more balance members may extend in the same direction as the capture member. The balance member may be attached to the support member. At least part of the balance member may extend in a curve. The convex portion of the curve may face radially outwardly.

In one case the filter comprises a vena cava filter. The filter may comprise an inferior vena cava filter.

In another aspect the invention provides a vascular filter assembly comprising: —
  a vascular filter of the invention; and
  a delivery device for delivering the filter to a desired location in a blood vessel.

In one embodiment of the invention at least part of the delivery device is movable between a delivery configuration and a deployed configuration. At least part of the delivery device may be collapsed in the delivery configuration. At least part of the delivery device may be expanded in the deployed configuration. The delivery device may be inflatable. The delivery device may comprise a balloon member.

In one case the delivery device comprises a cover member to at least partially cover the filter in the delivery configuration. The cover member may be movable relative to the filter to uncover the filter in the deployed configuration. The cover member may comprise a sheath.

In a further aspect of the invention there is provided a vascular filter assembly comprising: —
  a vascular filter of the invention; and
  a retrieval device for retrieving the filter from a location in a blood vessel.

In one embodiment of the invention the retrieval device comprises an engagement member for engaging the filter. The retrieval device may define a reception space for at least partially receiving the filter. The engagement member may be movable relative to the reception space to at least partially receive the filter in the reception space.

According to another aspect of the invention there is provided a method of treating a blood vessel, the method comprising the step of deploying a vascular filter at a desired location in the blood vessel, the filter capturing thrombus passing through the blood vessel.

In one embodiment of the invention the method comprises the step of delivering the filter in a delivery configuration to the desired location in the blood vessel. At least part of the filter may move from the delivery configuration to a deployed configuration at the desired location in the blood vessel.

Deployment of the filter may embed at least part of the filter into a wall of the blood vessel.

In one case at least part of the filter moves from a capturing configuration in which thrombus passing through the blood vessel is captured, to an open configuration.

The method may comprise the step of retrieving the filter from the blood vessel. The method may comprise the step of removing the filter from the wall of the blood vessel. A removal force may be applied in a direction substantially parallel to the longitudinal axis of the blood vessel to remove the filter from the wall of the blood vessel.

In one case the invention provides a method of treating the vena cave. In another case the invention provides a method of treating the inferior vena cava.

IVC filter placement may be used as a prophylactic means for preventing PE in patients at high risk for thromboembolic events. The invention in suit greatly aids the use of filters during a period of high risk for thromboembolic events.

The filter of the invention can be used either permanently, or temporarily with subsequent retrieval or conversion for PE prevention. If the filter is left in place, it functions as a permanent IVC filter. Alternatively, the filters may be retrieved once the duration of PE prophylaxis has been achieved.

The invention provides in one particular case a retrievable and/or bio-resorbable filter.

BRIEF DESCRIPTION OF THE DRAWINGS

The invention will be more clearly understood from the following description of some embodiments thereof, given by way of example only, with reference to the accompanying drawings, in which:

FIG. 1 is an isometric view of a vascular filter according to the invention;

FIG. 2 is an end view of the filter of FIG. 1;

FIG. 3 is an isometric view of a support member of the filter of FIG. 1;

FIG. 4 is a developed, plan view of two capture members of the filter of FIG. 1;

FIGS. 10 to 12 are views similar to FIGS. 1 to 3 of another vascular filter according to the invention;

FIG. 13 is an isometric view of another vascular filter according to the invention;

FIG. 14 is an end view of the filter of FIG. 13 is a delivery configuration;

FIG. 15 is an end view of the filter of FIG. 13 in a deployed configuration, in use;

FIGS. 24 to 26 are views similar to FIGS. 1 to 3 of another vascular filter according to the invention;

FIG. 26(d) is a side view of the filter of FIG. 26(a) in a capturing configuration, in use;

FIG. 26(e) is an end view of the filter of FIG. 26(d) in the capturing, in use;

FIGS. 26(f) and 26(g) are views similar to FIGS. 26(d) and 26(e) of the filter of FIG. 26(a) in an open configuration, in use;

FIGS. 26(i) and 26(j) are views similar to FIGS. 26(b) and 26(c) of another vascular filter according to the invention;

FIG. 26(k) is a side view of part of the filter of FIG. 26(i);

FIG. 26(l) is an end view of the part of FIG. 26(k);

FIG. 26(m) is an enlarged, end view of the part of FIG. 26(l);

FIGS. 26(n) and 26(o) are enlarged, end views of parts of the filter of FIG. 26(i);

FIGS. 27 and 28 are views similar to FIGS. 1 and 2 of another vascular filter according to the invention in a capturing configuration;

FIG. 29 is an isometric view of capture members and a support member of the filter of FIGS. 27 and 28 in an open configuration;

FIG. 30 is an isometric view of a holder member of the filter of FIGS. 27 and 28;

FIG. 31 is an isometric view of a holder member of another vascular filter according to the invention;

FIGS. 37 to 39 are views similar to FIGS. 27 to 29 of another vascular filter according to the invention;

FIG. 52(a) is an isometric view of another vascular filter according to the invention;

FIG. 52(b) is a side view of the filter of FIG. 52(a);

FIG. 52(c) is an end view of the filter of FIG. 52(a);

FIG. 52(d) is an enlarged, side view of part of the filter of FIG. 52(b);

FIGS. 55 and 56 are isometric views of further vascular filters according to the invention;

FIGS. 57 and 58 are partially cross-sectional, side views of the filter of FIG. 56, in use;

FIG. 59 is an isomeric view of one of the support members of the filter of FIG. 56;

FIGS. 60 to 63 are views similar to FIGS. 56 to 59 of another vascular filter according to the invention;

FIGS. 63(d) to 63(g) are views similar to FIGS. 56 to 59 of another vascular filter according to the invention;

FIG. 67 is an isometric view of a further vascular filter according to the invention;

FIG. 68 is an end view of the filter of FIG. 67 in a deployed configuration;

FIG. 69 is an end view of the filter of FIG. 67 in a delivery configuration;

FIG. 70 is isometric view of another vascular filter according to the invention;

FIGS. 71 to 73 are views similar to FIGS. 67 to 69 of a further vascular filter according to the invention;

FIGS. 74 and 76 are partially cross-sectional, side views of the filter of FIGS. 71 to 73, in use;

DETAILED DESCRIPTION

Figure 5:
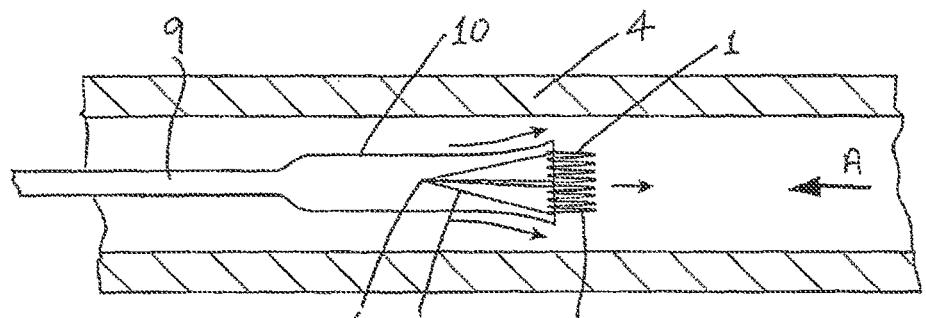
FIGS. 5 to 9 are partially cross-sectional, side views of the filter of FIG. 1, in use.

In this patent specification, the terms "proximal" will be understood to mean the end closest to a user when carrying out a procedure accessed from & femoral vein, or the caudal end. Similarly the term "distal" will be understood to mean the end furthest from a user when carrying out a procedure accessed from a femoral vein, or the cranial end.

Referring to the drawings, and initially in FIGS. 1 to 9 thereof, there is illustrated a vascular filter assembly according to the invention. The vascular filter assembly comprises a vascular filter 1 according to the invention and a delivery catheter 9 for delivering the filter 1 to a desired location in a blood vessel, such as the inferior vena cava 4. The vascular filter 1 is suitable for use as an inferior vena cava filter in the inferior vena cava 4 to capture thrombus 8 passing through the inferior vena cava 4 towards the heart and the lungs. The vascular filter 1 may thus be used to prevent pulmonary embolism.

The filter 1 comprises a support hoop 2 and four or more capture arms 3 for capturing thrombus 8 passing through the inferior vena cava 4.

The support hoop 2 comprises a wire element 5 which extends circumferentially in a sinusoid wave pattern (FIG. 3).

Figure 6:
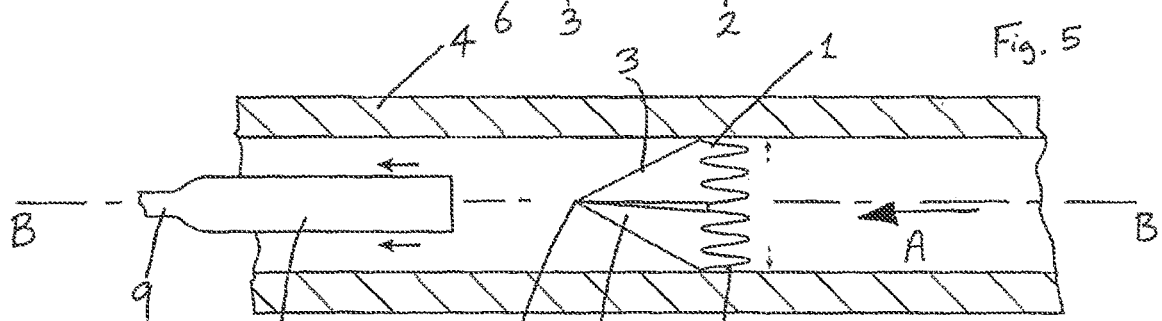

The support hoop 2 is movable between a collapsed delivery configuration (FIG. 5) and an expanded deployed configuration (FIG. 6). When the filter 1 is deployed in the inferior vena cava 4, the support hoop 2 extends circumferentially around the internal wall of the inferior vena cava (FIG. 6).

The support hoop 2 is biased radially outwardly towards the deployed configuration. When the filter 1 is deployed in the inferior vena cava 4, the support hoop 2 exerts a force radially outwardly on the wall of the inferior vena cava 4. In this manner the support hoop 2 supports the four capture arms 3 in position relative to the wall of the inferior vena cava 4.

Figure 7:
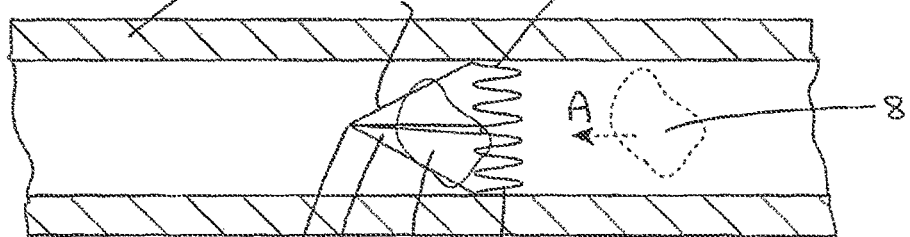

Each capture arm 3 is attached to the support hoop 2 by wrapping or knotting or bonding an end of the capture arm 3 around the wire element 5 (FIG. 1). The four capture arm 3 extend in a substantially straight line to an apex 6, where the four capture arms 3 engage each other (FIG. 1). In this manner the four capture arms 3 define a generally conically shaped capture region 7 within which thrombus 8 may be captured (FIG. 7). When the filter 1 is deployed in the inferior vena cava 4, the apex 6 is substantially in-line with the longitudinal axis B-B extending through the centre of the inferior vena cava 4 (FIG. 6), and the capture region 7 is located in the region of the centre of the inferior vena cava 4 (FIG. 6). The capture arms 3 may be taut as shown or hang loosely in the bloodstream.

The capture arms 3 are movable between a collapsed delivery configuration (FIG. 5) and an expanded deployed configuration (FIG. 6). When the filter 1 is deployed in the inferior vena cava 4, the capture arms 3 extend in the direction of blood flow A through the inferior vena cava 4 (FIG. 6). The capture arms 3 are biased towards the deployed configuration.

Each of the capture arms 3 is of a biodegradable and/or bioabsorbable material. Similarly, the support hoop 2 may also be formed a biodegradable and/or bio-absorbable material.

The filter element 1 has a taper configuration. The woven biodegradable arms 3 have a double taper (FIG. 4). The element 3 may equally be formed from a monofilament or multi-filament structure.

The filter 1 has as even number of elements 3 (FIG. 2). In an alternative configuration the filter may have an odd number of elements 3.

The multiple elements 3 degrade based on circumference from centre to outside of the vessel 4.

By increasing the number of capture arms 3, the size between adjacent arms 3 is reduced to enhance filtering performance.

The delivery catheter 9 comprises a restraining sheath 10 which covers at least part of the collapsed filter 1 in a delivery configuration (FIG. 5). The sheath 10 is movable proximally relative so the filter 1 to a deployed configuration to uncover the filter 1 and thus facilitate deployment of the filter 1 (FIG. 6).

The filter element 3 with the tapered configuration may be formed in a variety of possible manners. For example by casting, dipping into a polymer solution with an extraction rate controlled to allow evaporation of solvent and deposition of polymer. The filter element 3 may be alternatively formed by extruded bump tubing, in which cast the thermoplastic polymer is extruded into the tapered configuration.

In use the support hoop 2 and the four capture arms 3 are collapsed to the delivery configuration, and at least partially loaded into the delivery catheter 9. The delivery catheter 9 is advanced through the inferior vena cava 4 until the collapsed filter 1 reaches the desired location in the inferior vena cava 4 (FIG. 5) The restraining sheath 10 of the delivery catheter 9 is then moved proximally relative to the filter 1 to fully uncover the filter 1. Due to the biasing nature of the support hoop 2 and the capture arms 3, the support hoop 2 and the capture arms 3 move from the collapsed delivery configuration to the expanded deployed configuration (FIG. 6). In the deployed configuration, the support hoop 2 exerts a radially outwardly force on the internal wall of the inferior vena cava 4 to support the capture arms 3 in the desired position in the inferior vena cava 4.

Figure 8:
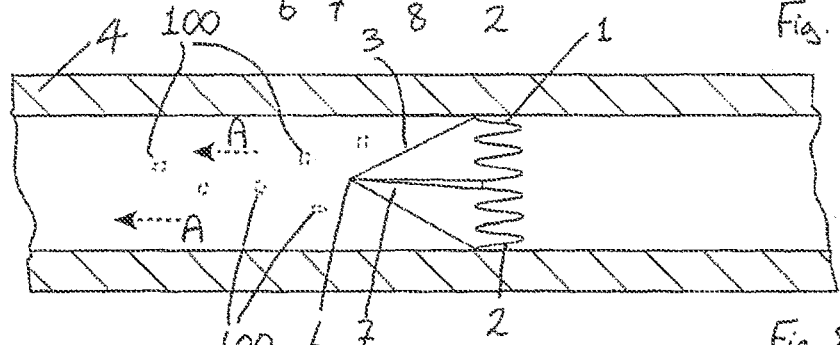

In the event of thrombus 8 passing through the inferior vena cava 4 towards the heart and the lungs, the thrombus 8 will be captured in the capture region 7 of the filter 1 (FIG. 7). The thrombus 8 will thus be prevented from passing into the heart and the lungs which could otherwise lead to pulmonary embolism. The captured thrombus 8 will gradually be broken down by the body into smaller size particles 100, which will significantly reduce the risk embolism (FIG. 8).

Figure 9:
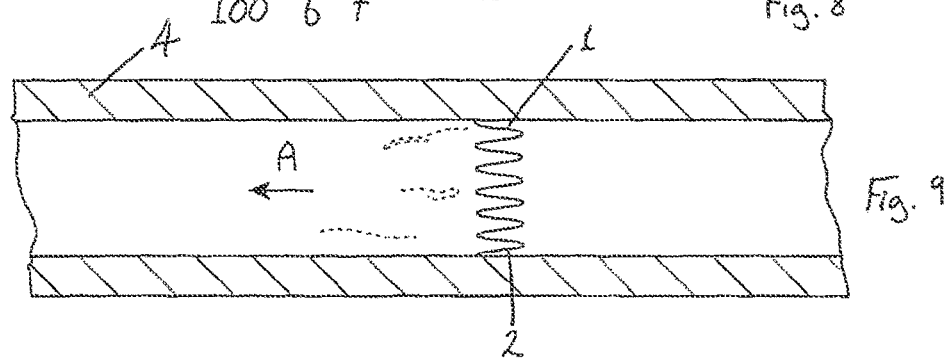

Due to the biodegradable/bioabsorbable material of the capture arms 3, the capture arms 3 will eventually biodegrade/bioabsorb (FIG. 9). Thus only the support hoop 2 will remain in the inferior vena cava 4.

The delivery systems for delivery of the vena cava filter 1 may employ push and/or pull from either the jugular or femoral side.

The delivery system may use rotational deployment.

The delivery system may be a rapid exchange system for single operator deployment.

The delivery system may use linear ratchet deployment and/or rotational ratchet deployment. The operator preferably keeps purchase on the filter 1 until the location is finalised. The delivery system may be a push forward system. In this case the operator aligns the distal catheter marker to the location of mural attachment, and then pushes out the filter 1.

It will be appreciated that part or all of the support hoop 2 may be biodegradable/bioabsorbable, so that no part of the filter 1 will remain permanently in the inferior vena cava 4.

In FIGS. 10 to 12 there is illustrated another vascular filter 20 according to the invention, which is similar to the vascular filter 1 of FIGS. 1 to 9, and similar elements in FIGS. 10 to 12 are assigned the same reference numerals.

In this case the support hoop 21 is provided in the form of a mesh or trellis 23. The mesh/trellis 23 comprises a number of openings 22 therethrough.

The trellis filter 20 of FIGS. 10 to 12 is similar to a mural trellis with a number of woven elements 3 extending to a proximal point 6. The elements 3 may be joined, or may be not joined at the apex 6.

The filter 20 may be of metallic material and/or of biodegradable material. For example the filter 20 may be a combination of a metallic mural 21 and biodegradable elements 3.

The trellis design may be either self expanding or balloon expandable.

In one embodiment the trellis 23 comprises thin wires with weave fixed at ends to prevent unravelling. In another embodiment the trellis 23 comprises thin wires interwoven with free ends. Either embodiment may be used for the mural element 21.

FIGS. 13 to 15 to illustrate a further vascular filter 30 according to the invention, which is similar to the vascular filter 20 of FIGS. 10 to 12, and similar elements in FIGS. 13 to 15 are assigned the same reference numerals.

In this case the support hoop 31 comprises a body portion 32 and a plurality of openings 33 extending through the body portion 32.

In the collapsed delivery configuration the support hoop 31 has a spiral configuration (FIG. 14). In the expanded deployed configuration, one end 34 of the support hoop 31 overlaps the other end 35 of the support hoop 31.

The openings 33 in the support hoop 31 facilitate tissue ingrowth 36 (FIG. 15).

The support hoop 31 may be a coil based system, FIG. 14 illustrates the closed configuration, and FIG. 15 illustrates the open configuration.

The wall or the support hoop 31 may be planar or be of an open structure (FIG. 13).

The element structure 3 may the knotted using sutures to the support hoop 31.

Figure 17:
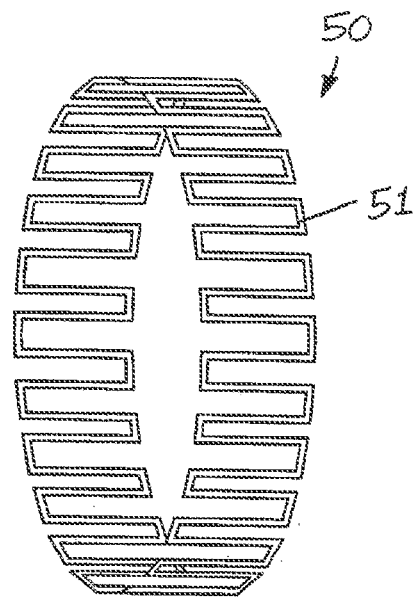
FIGS. 16 and 17 are isometric views of support members of other vascular filters according to the invention.
Figure 16:
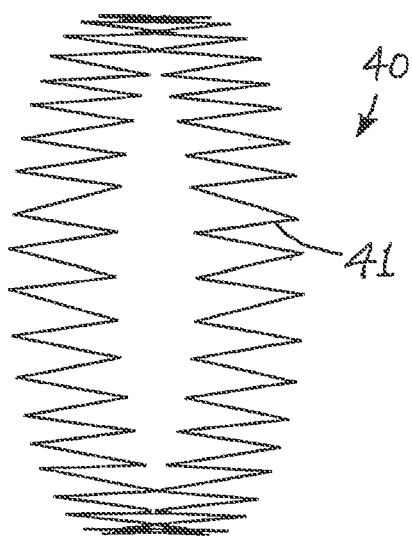

It will be appreciated that a variety of possible shapes and configurations are possible for the support hoop. For example, FIG. 16 illustrates a support hoop 40 which comprises a wire element 41 which extends circumferentially in a jagged wave pattern. FIG. 17 illustrates a support hoop 50 which comprises a body portion 51 which extends circumferentially in a square wave pattern.

The support hoop may have a peak to peak design in the circular deployed configuration (FIG. 16). The support hoop may be formed of fixed length wires joined at each end to the wire on either side (FIG. 16), or alternatively may be cut from a single sheet (FIG. 17).

The support hoop designs of FIGS. 16 and 17 may also be suitable for use as a stent.

Figure 17B:
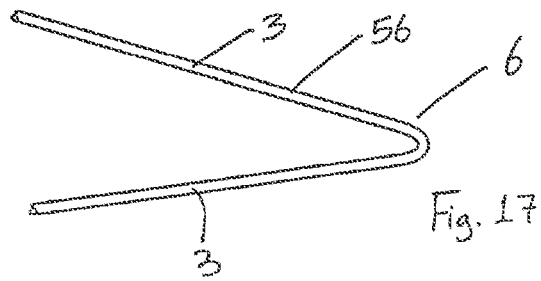
FIGS. 17(a) and 17(b) are side views of capture members of other vascular filters according to the invention.
Figure 17A:
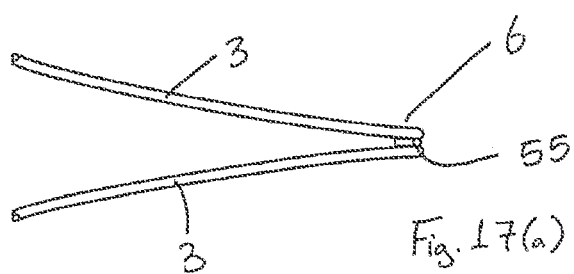
Figure 18:
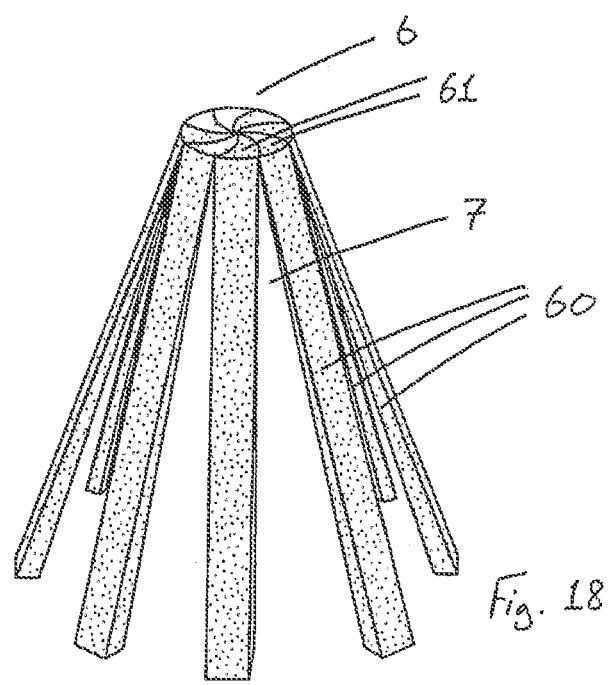
FIG. 18 is an isometric view of capture members of another vascular filter according to the invention.
Figure 20:
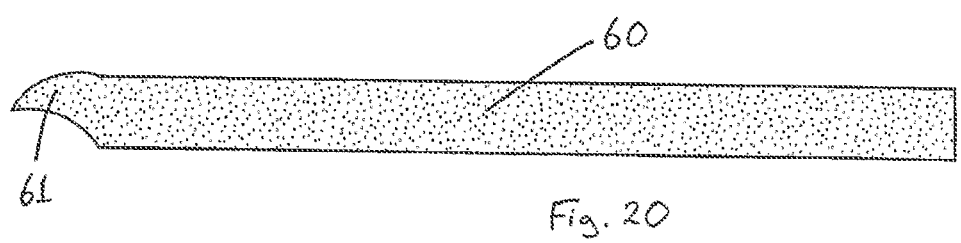
FIG. 20 is a plan view of one the capture members of FIG. 18.
Figure 19:
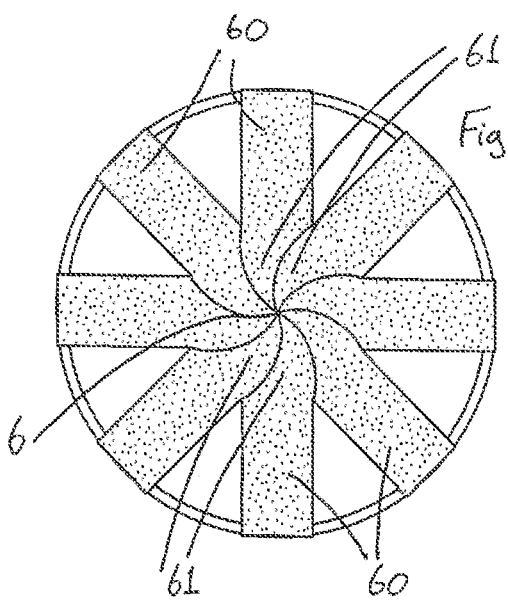
FIG. 19 is an end view of the capture members of FIG. 18.
Figure 21:
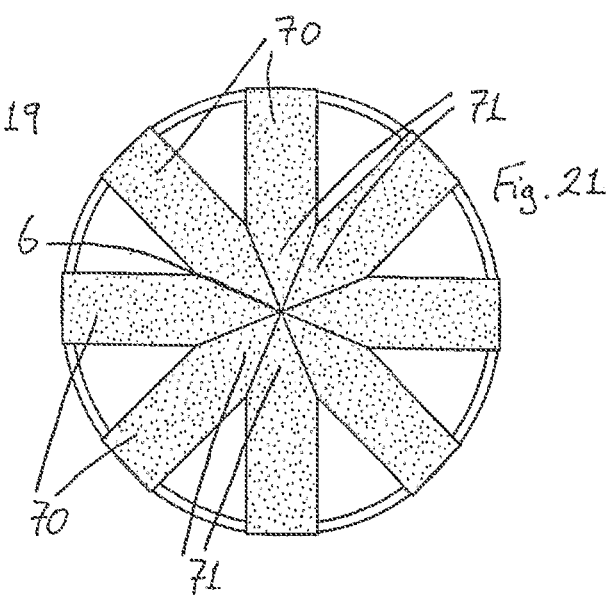
FIG. 21 is an end view of capture members of another vascular filter according to the invention.

It will further be appreciated that the capture arms may engage each other at the apex 6 in a variety of possible shaped and configurations. For example, the capture arms 3 may be fixedly attached to one another by a weld joint, solder or adhesive 55 at the apex 6 (FIG. 17(a)). Alternatively the capture arms 3 may be integrally formed from a single element 56 bent back on itself to form the capture arms 3 (FIG. 17(b)). As a further example in FIGS. 18 to 20 each capture arm 60 terminates in a curved, pointed tip 61 (FIG. 20). The tips 61 nest with one another at the apex 6 (FIG. 19). In FIG. 21 each capture arm 70 terminates in a straight, pointed tip 71. The tips 71 nest with one another at the apex 6 (FIG. 21).

FIG. 19 illustrates the nesting elements 60. The geometries of the elements 60 are configured to nest at the apex 6 of the filter such that a frame is erected during deployment that will not allow significant thrombus to pass.

Figure 22:
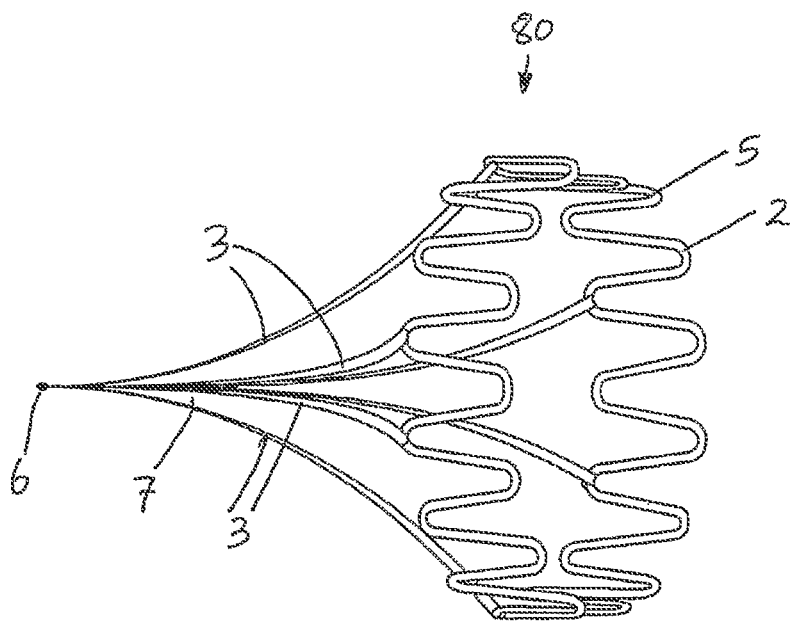
FIGS. 22 and 23 are isometric views of further vascular filters according to the invention.

Referring to FIG. 22 there is illustrated another vascular filter 80 according to the invention which is similar to the vascular filter 1 of FIGS. 1 to 9, and similar elements in FIG. 22 are assigned the same reference numerals.

In this case the capture arms 3 extend in a curve to the apex 6. The concave portion of the curve faces radially outwardly.

Figure 23:
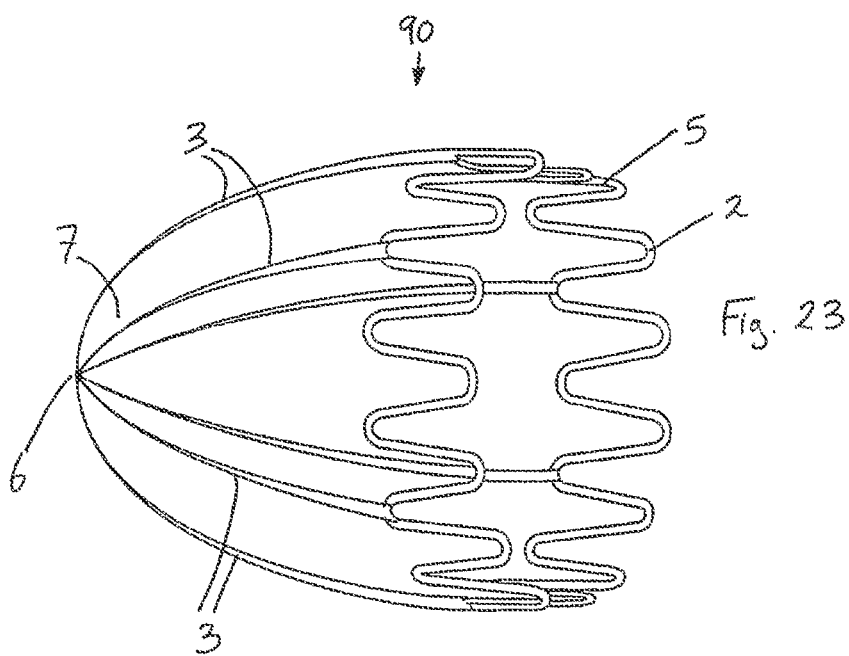

In FIG. 23 there is illustrated a further vascular filter 90 according to the invention which is similar to the vascular filter 80 of FIG. 22, and similar elements in FIG. 23 are assigned the same reference numerals.

In this case the capture arms 3 extend in a curve to the apex 6. The convex portion of the curve faces radially outwardly. These capture arms 3 may be moulded or machined into the configurations shown.

Possible geometries for the vena cava filter include conical shape, concave shape, and convex shape geometries.

FIGS. 24 to 26 illustrate another vascular filter 110 according to the invention, which is similar to the vascular filter 1 of FIGS. 1 to 9, and similar elements in FIGS. 24 to 26 are assigned the same reference numerals.

In this case the capture arm 112 is provided integral with the support hoop 2. In particular the capture arm 112 is provided as an extension of one of the sinusoid curves of the wire element 5 (FIG. 26). The other three capture arms 113 are similar to the capture arms 3 described previously with reference to FIGS. 1 to 9.

The capture arms 112, 113 define an offset conically shaped capture region 111. When the filter 110 is deployed in the inferior vena cava 4, the apex 6 is offset from the longitudinal axis B-B extending through the centre of the inferior vena cava 4, and the capture region 111 is located in the region of the internal wall of the inferior vena cava 4.

The support hoop 2 may be a Nitinol (Ni Ti) sinusoid or may be a stainless steel sinusoid. Alternatively the support hoop 2 may be of a zigzag or crown design. The elements 113 may be of Nitinol stainless steel, titanium or a biodegradable material.

The filter 110 has a single extended element 112.

The offset filter 110 directs embolus to the side wall. This arrangement may be advantageous. It may allow more blood flow at the centre of the vena cava 4 by directing thrombus 8 away from the centre of blood flow.

Alternatively, taper elements could be used.

Referring to FIGS. 26(a) to 26(g) there is illustrated another vascular filter 300 according to the invention, which is similar to the vascular filter 1 of FIGS. 1 to 9, and similar elements in FIGS. 26(a) to 26(g) are assigned the same reference numerals.

In this case the filter 300 comprises a proximal support hoop 302 at the proximal end of the filter 300, a distal support hoop 312 at the distal end of the filter 300, and a plurality of support struts 303 extending between the proximal support hoop 302 and the distal support hoop 312.

The proximal support hoop 302 comprises a wire element 5 which extends circumferentially around the wall of the inferior vena cava 4 in a sinusoid wave pattern. Similarly the distal support hoop 312 comprises a wire element 5 which extends circumferentially around the wall of the inferior vena cava 4 in a sinusoid wave pattern. The support struts 303 extent longitudinally along the wall of the inferior vena cava 4. The support struts 303 connect the proximal support hoop 302 to the distal support hoop 312. In this case the proximal support hoop 302, the distal support hoops 312 and the support struts 303 are formed integrally. The proximal support hoop 302, the distal support hoop 312 and the support struts 303 may be of a shape-memory material, such as Nitinol.

Figure 26A:
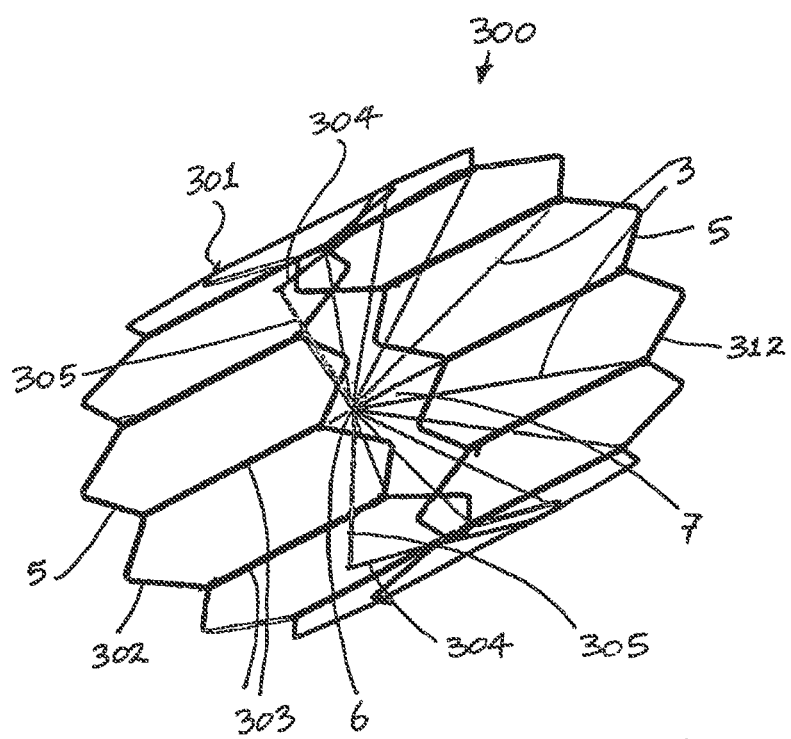
FIG. 26(a) is an isometric view of another vascular filter according to the invention.
Figure 26B:
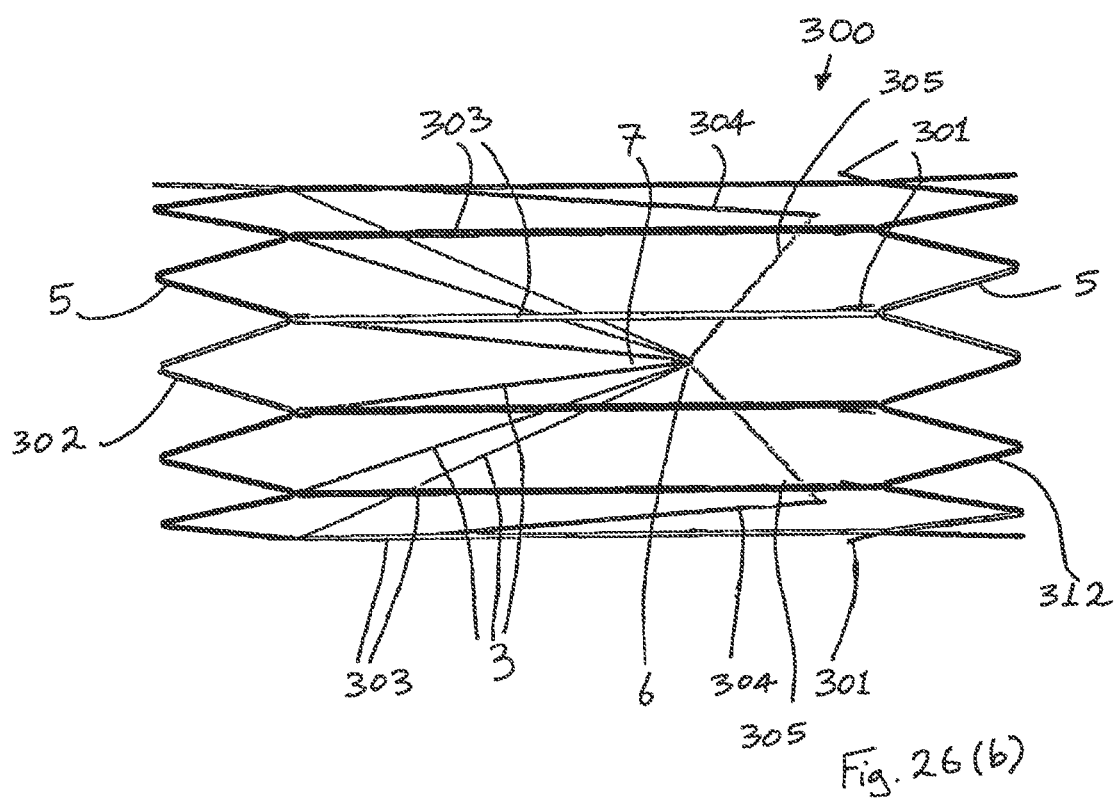
FIG. 26(b) is a side view of the filter of FIG. 26(a)
Figure 26C:
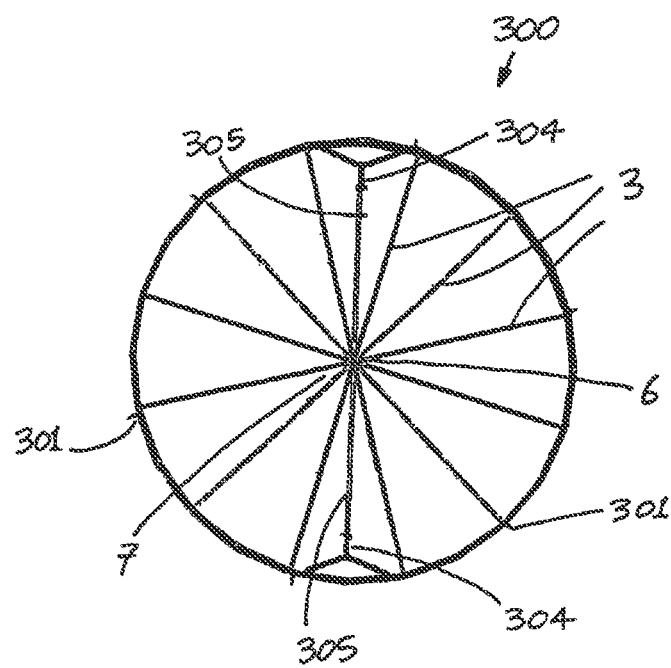
FIG. 26(c) is an end view of the filter of FIG. 26(a)
Figure 26H:
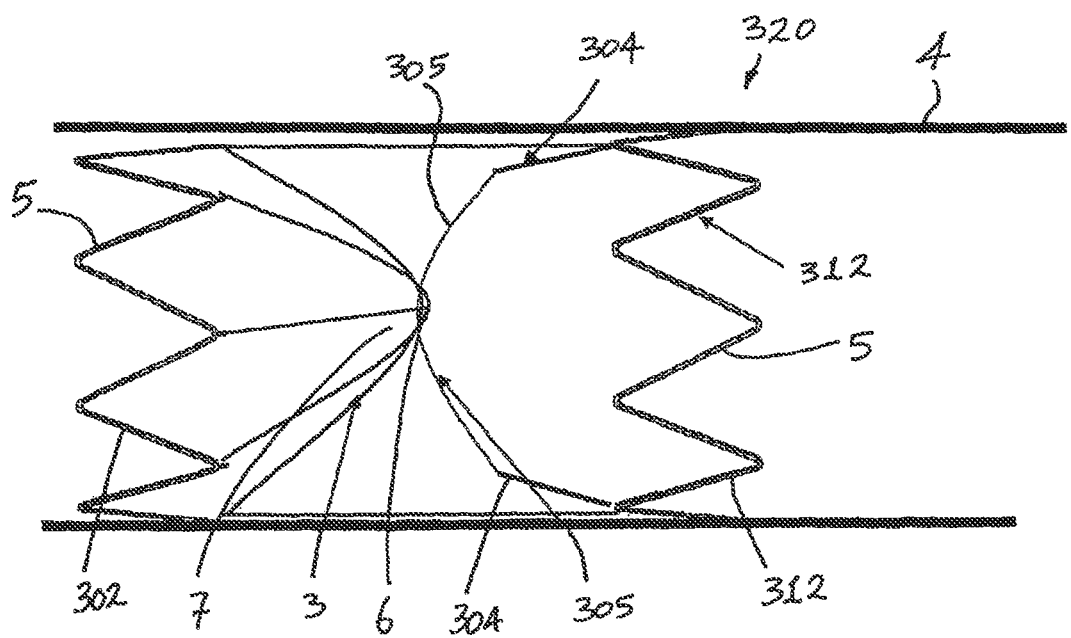
FIG. 26(h) is a view similar to FIG. 26(d) of another vascular filter according to the invention.
Figure 32:
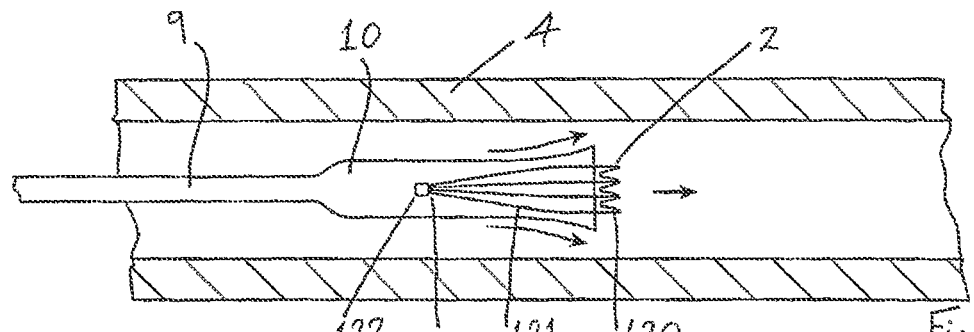
FIGS. 32 to 38 are partially side views of the filter of FIGS. 27 and 28, in use.

As illustrated in FIG. 26(b), the distal end of the distal support hoop 312 is located distally of the capture arms 3 and the apex 6, and the proximal end of the proximal support hoop 302 is located proximally of the capture arms 3.

The filter 300 also comprises a plurality of integral, or joined metal, or biodegradable/bioabsorbable barbs 301 to assist in anchoring the filter 300 relative to the inferior vena cava 4.

In addition the filter 300 comprises two or more tensioning arms 304 and two or more connecting arms 305.

Each tensioning arm 304 is provided in the form of a cantilever arm. The distal of the tensioning arm 304 is located distally of the apex 6, and the proximal end of the tensioning arms 304 is located proximally of the apex 6.

The tensioning arms 304 are movable between a capturing configuration (FIG. 26(d)) and an open configuration (FIG. 25(f)). In the capturing configuration, the tensioning arms 304 are inclined distally inwardly relative to the longitudinal axis of the inferior vena cava 4. In the open configuration, the tensioning arms 304 are aligned parallel to the wall of the inferior vena cava 4. The tensioning arms 304 are biased towards the open configuration. The tensioning arms 304 may be of a shape-memory material, such as Nitinol.

The connecting arms 305 connect the tensioning arms 304 to the capture arms 3 at the apex 6. In this manner the tensioning arms 304 act to tension the capture arms 3 to prevent the capture arms 3 from becoming slack and/or to prevent the apex 6 from moving off-centre. Alternatively the tensioning arms 304 may originate at the caudal end of the filter 300.

The connecting arms 305 are of biodegradable/bioabsorbable material, in this case.

In use, due to the biodegradable/bioabsorbable material of the connecting arms 305, the connecting arms 305 will eventually biodegrade/bioabsorb. This enables the tensioning arms 304 to move from the capturing configuration to the open configuration. Only the proximal support hoop 302, the distal support hoop 312, the support struts 303 and the tensioning arms 304 remain in the inferior vena cava 4 (FIG. 26(*f*)).

FIGS. 26(*a*) to 26(*g*) illustrate the net filter design.

FIG. 26(*b*) illustrates the filtering elements 3, the tensioning element 304, the tensioning filament 305, the crown elements 302, 312.

The net filter design comprises the Nitinol frame 302, 303, 312 with a tubular profile which has the number of bioabsorbable filaments 3 attached and spanning across its diameter in order to create a filter capable of trapping blood clots.

The Nitinol frame is a single component which comprises zigzag type design features called crowns 302, 312 at both its ends. This design allows the device 300 to be crimped or reduced in diameter so that it can be delivered through the vascular system in a catheter of much smaller diameter than the vena cava 4.

The elastic energy in the deformed crowns 302, 312 enables the device 300 to expand to the vessel diameter. The component is designed so these crowns 302, 312 exert outward radial pressure against the internal wall of the vena cava 4 within the range of vessels typically encountered. The two sets of crowns 302, 312 are linked by the connecting elements 303.

The filter 300 is created by the number of bioabsorbable filaments 3 which span the vessel lumen.

In order to deal with varying vessel diameters and to ensure that the filaments 3 are capable of trapping and retaining a piece of blood clot, it is desirable that the absorbable elements 3 take up a tensioned conical configuration.

This is achieved by means of a tensioning feature 304 on the Nitinol frame and a tensioning filament 305 which pulls the filtering filaments 3 in the cranial direction creating a tensioned filter not irrespective of the diameter of vessel 4 in which it is implanted.

The materials used have a known degradation profile such that they will provide protection to the patient while they are at risk and once this risk is minimised the materials will breakdown and become metabolised. The tensioning feature 304 on the Nitinol frame will spring back to the vessel wall with sufficient outward pressure to promote endothelial covering and encapsulation in tissue preventing or reducing the long term complications of obstructing blood flow associated with permanent vena cava filters.

In order to ensure that no migration takes place, the small barbs 301 are located at the cranial end of the connecting elements 303. They have sharp edges that are angled to anchor into the vessel tissue. The design features barbs 301 which may face in either direction, or may have separate barbs 301 facing in opposite directions.

The filter 300 comprising bioabsorbable elements 3 creates a rigid conical shape across a wide range of vessel diameters. This may be achieved using the tensioning system shown in FIG. 26(*b*). The short metallic cantilever type elements 304 are connected to the tensioning filament 305 that pulls the filtering element 3 in the cranial direction when positioned in the vessel 4 with a relatively smaller diameter.

These metallic elements 304 may be visualised during implantation using fluoroscopy of other imaging technology and thus act as a radiopaque indicator as to whether the filter elements 3 have degraded or not.

The metallic frame 304 bends inward to create the cone independent of vessel size. This also creates a radiopaque indicator as to whether the filter 300 is still functioning.

In FIG. 26(*h*) there is illustrated another vascular filter 320 according to the invention, which is similar to the vascular filter 300 of FIGS. 26(*a*) to 26(*g*), and similar elements in FIG. 26(*h*) are assigned the same reference numerals.

In this case the tensioning arms 304 are inclined proximally inwardly relative to the longitudinal axis of the inferior vena cava 4 in the capturing configuration.

FIG. 26(*h*) illustrates the metallic tensioning element 304, the support frame 312, the bioabsorbable filter elements 3, and the bioabsorbable tensioning element 305.

The filter 320 has the bioabsorbable elements 3 spanning across the vessel lumen protecting the patient while they are at risk of a pulmonary embolism. These elements break down when the risk has passed. The elements 3 are connected to the metal frame which promotes tissue ingrowth and becomes encapsulated in the vessel wall similar to a stent.

The filter 320 has the ability to align the elements 3 in the centre of the vessel 4 so that they provide the maximum clot trapping ability. A wide range or blood vessel diameters may be encountered. Typically the inferior vena cava 4 may be in the range of 16 mm to 27 mm. The filter 320 has the ability to relay visually whether the elements 3 have absorbed or not, i.e. whether the filter 320 is still functioning and the patient protected from pulmonary embolism.

The filter 320 has one or more tensioning elements 304 that remove any slack in the filter elements 3 by increasing the filter cone angle as the diameter increases. The small cantilever type metallic elements 304 are deformed inward by the bioabsorbable element 303 to achieve the sketching out of the bioabsorbable filter elements 3 until they are tense and central in the vessel. The device 320 may be x-rayed to establish if it is in the filter configuration if it has converted by assessing the angle of the metallic tensioning elements 304.

FIGS. 26(*i*) to 26(*m*) illustrate another vascular filter 330 according to the invention, which is similar to the vascular filter 300 of FIGS. 26(*a*) to 26(*g*), and similar elements in FIGS. 26(*i*) to 26(*m*) are assigned the same reference numerals.

In this case the filter 330 comprises a plurality of linking arms 331 to link each capture arm 3 to the adjacent capture arm 3. The linking arms 331 are of a biodegradable/bioabsorbable material.

The capture arms 3 comprise a plurality of openings 332 through the wall of the capture arms 3 at the apex 6. The openings 332 reduce the tensile strength of the capture arms 3. In this manner the capture arms 3 provided with predetermined failure points to control biodegrading/bioabsorbing of the capture arms 3.

Similarly each linking arm 331 comprises an opening 333 through the wall of the linking arms 331. The opening 333 reduces the tensile strength of the linking arm 331. In this manner the linking arm 331 is provided with a predetermined failure point to control biodegrading/bioabsorbing of the linking arm 331.

FIG. 26(*i*) illustrates the tensioning arm 304, and the tensioning filament 305.

The filter 330 has bioabsorbable elements 3 spanning across the vessel lumen protecting the patient while they are at risk of a pulmonary embolism. These elements 3 break down when the risk has passed. The elements 3 are connected to the metal frame which will promote tissue ingrowth and become encapsulated in the vessel wall similar to a stent.

Maintaining the conical shape in which any thromboemboli caught by the filter 330 are stored in a central location may be an important feature, as this exposes the clot 8 to the highest flow rates. Consequently the clot 8 may be lysed in a shorter time period and the risk of IVC occlusion due to thrombosis may be reduced or minimised.

The absorbable net design 330 is manufactured in one component and may offer a more consistent conical filter shape and clot trapping efficiency than a series of single filaments 3. The net can adjust to varying diameters by means of the tensioning system provided by the tensioning filament 305 and the tensioning arm 304.

The filter 330 may be made by producing a cone shaped film and cutting a shape in the film to produce a filter capable of protecting the patient from pulmonary embolism. This may be achieved by solution casting a polymer film and cutting away material to achieve various filter shapes that preserve blood flow yet filter pieces of thrombi efficiently. The cutting process would be achieved using laser technology to ensure accurate dimensioning and freedom of filter design.

The component may be designed so that it will degrade initially in a controlled location by designing areas of reduced cross sectional area into the device. This will have the advantage of allowing the net to reduce to single strands and minimise the risk of a clinically significant pulmonary emboli.

The component may be made from a compliant material such as Polycaprolactone and copolymers of caprolactone and Lactide and/or Gylcolide. Other suitable polymers would be polymers derived from Polyhydroxybutyrate.

Referring to FIGS. 27 to 30 and 32 to 36 there is illustrated a further vascular filter 120 according to the invention, which is similar to the filter 1 of FIGS. 1 to 9, and similar elements in FIGS. 27 to 30 and 32 to 36 are assigned the same reference numerals.

In this case the filter 120 comprises six capture arms 121 integrally formed with the support hoop 2. The capture arms 121 are movable between a capturing configuration (FIG. 27) and an open configuration (FIG. 29). In the capturing configuration, the capture arms 121 extend to the apex 6 and define the conically shaped capture region 7. The capture arms 121 are biased towards the open configuration, and a holder tube 122 is provided around the ends of the capture arms 121 to hold the capture arms 121 in the capturing configuration. The holder tube 122 is biodegradable and/or bioabsorbable. Upon biodegrading/bioabsorbing of the holder tube 122, the capture arms 121 are free to move from the capturing configuration to the open configuration (FIG. 29). The capture arms 121 are not biodegradable or bioabsorbable.

Figure 33:
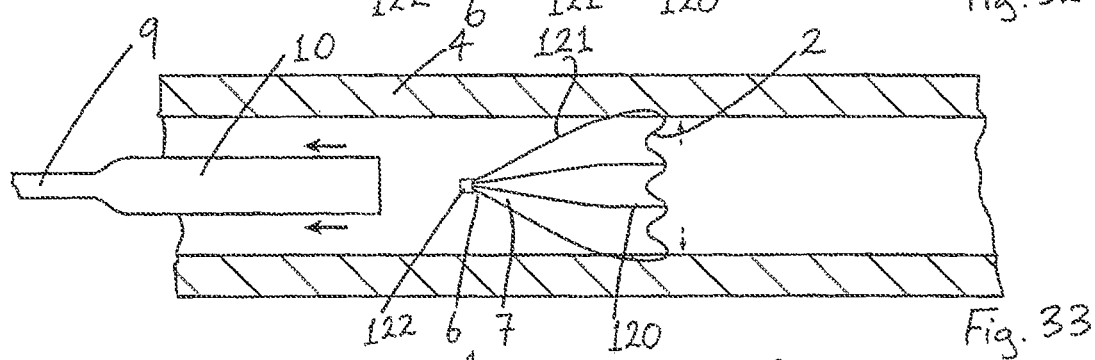
Figure 34:
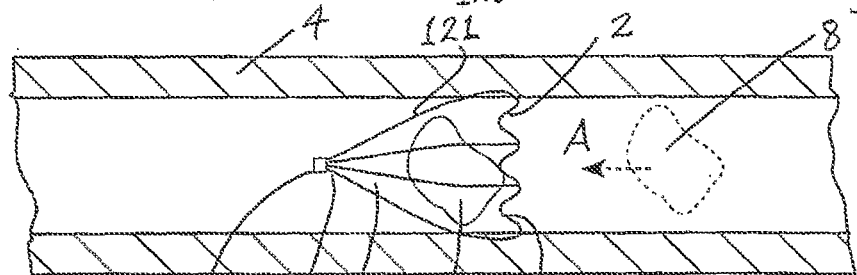
Figure 35:
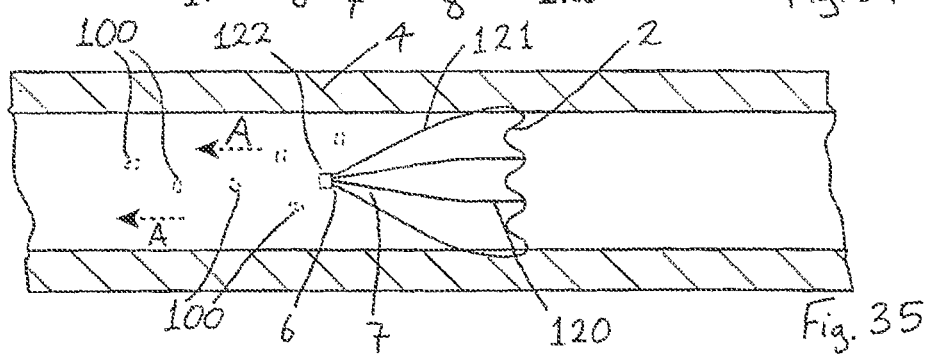
Figure 36:
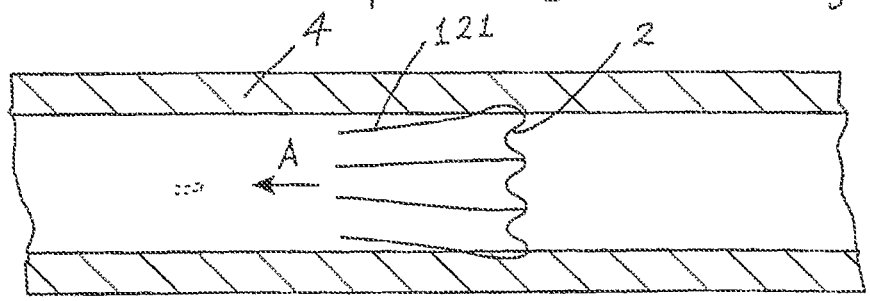

In use, in the deployed configuration, the support hoop 2 is partially embedded in the internal wall of the inferior vena cava 4 to support the capture arms 121 in the desired position in the inferior vena cava 4 (FIG. 33). Due to the biodegradable/bioabsorbable material of the holder tube 122, the holder tube 122 will eventually biodegrade/bioabsorb (FIG. 36), which enables the capture arms 121 to move from the capturing configuration to the open configuration. The support hoop 2 and the capture arms 121 remain in the inferior vena cava 4.

It will be appreciated that a variety of possible shapes and configurations are possible for the holder member which holds the capture arms 121 in the capturing configurations.

For example in FIG. 31, the holder member is provided in the form of a bioabsorbable and/or biodegradable coil 130 around the ends of the capture arms 121 to hold the capture arms 121 in the capturing configuration.

The shape memory of the capture arms 121 are configured to remember a tubular shape. The only biodegradable element of the filter 120 is the holder 122 at the apex 6 of the filter 120.

The apex suture 130 bioresolves and the arms 121 revert to the tubular configuration (FIG. 31). Alternatively, the cap 122 at the apex 6 can be bio-resorbed (FIG. 30).

The filter arms 121 are not retrieved in this embodiment. The bio-resorbable point 122 allows the filler (Ni Ti) 121 or other material to relax to the wall and remain in the body.

Alternatively, the filter cap 122 may not be resorbable but may be retrieved by a snare or other removal device.

Another alternative is to replace the bio-resorbable cap by way of an interventional procedure to extend the period for which protection is provided to the patient.

In a further alternative, a metallic or bio-stable polymer element may be used to replace the filter cap to convert the implant device into a permanent implant. Alternatively the permanent configuration may be welded or otherwise permanently joined at the apex.

Figure 37:
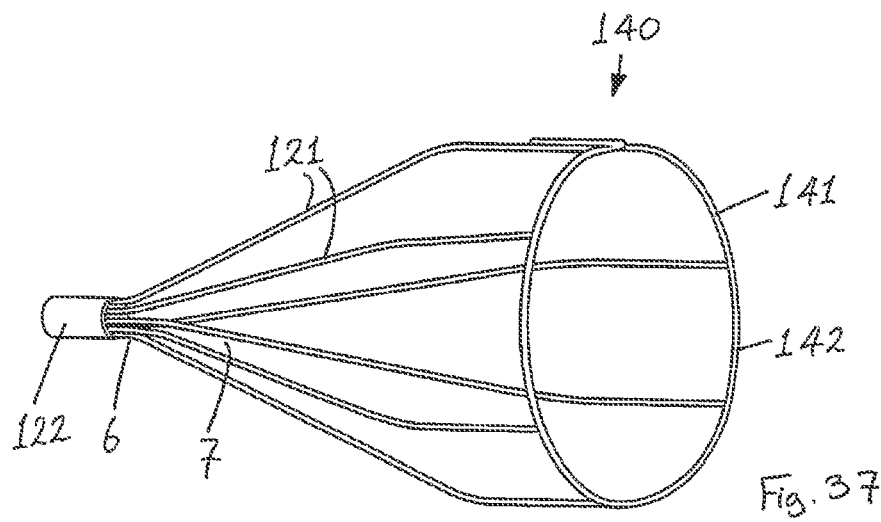
Figure 38:
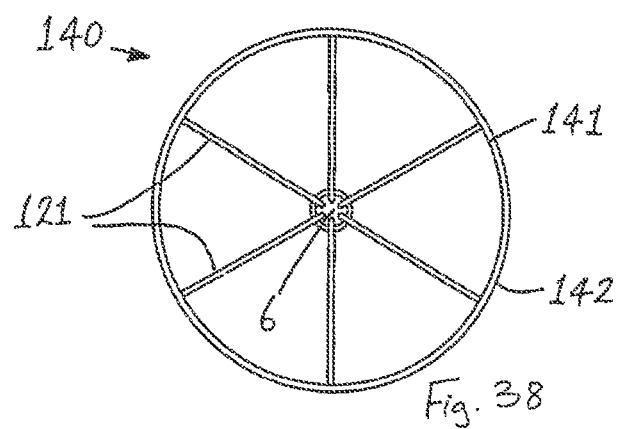
Figure 39:
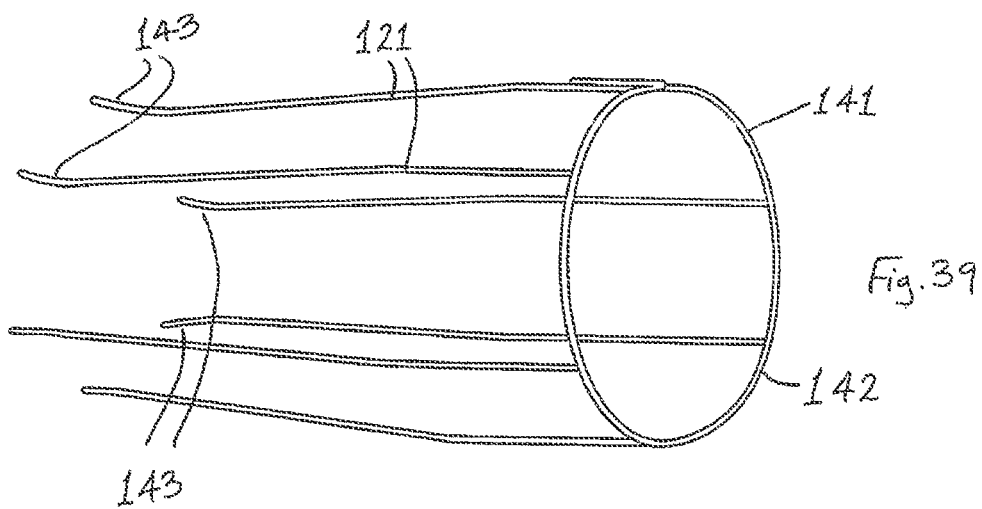

In FIGS. 37 to 39 there is illustrated another vascular filter 140 according to the invention, which is similar to the vascular filter 120 of FIGS. 27 to 30 and 32 to 36, and similar elements in FIGS. 37 to 39 are assigned the same reference numerals.

In this case the support hoop 141 comprises a wire element 142 which extends circumferentially in a plane.

As illustrated in FIG. 39 the free end 143 of each capture arm 121 curves radially outwardly.

FIGS. 39(a) to 44 illustrate another vascular filter 145 according to the invention, which is similar to the vascular filter 140 of FIGS. 37 to 39, and similar elements in FIGS. 39(a) to 44 are assigned the same reference numerals.

Figure 39B:
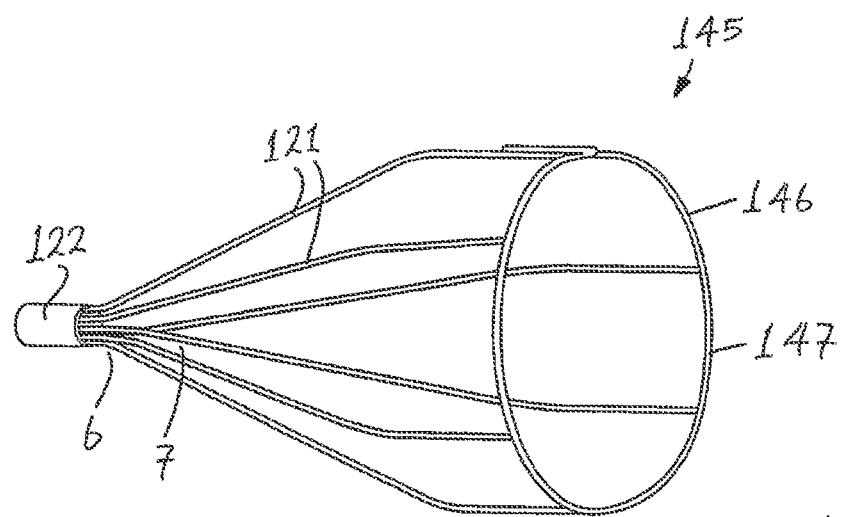
FIG. 39(b) is an isometric view of the filter of FIG. 39(a) in an expanded deployed configuration.
Figure 39A:
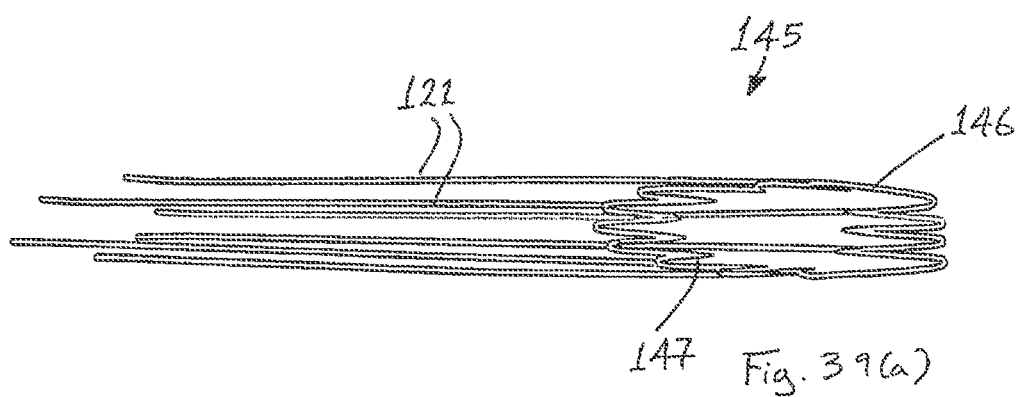
FIG. 39(a) is as isometric view of another vascular filter according to the invention in a collapsed delivery configuration.
Figure 40:
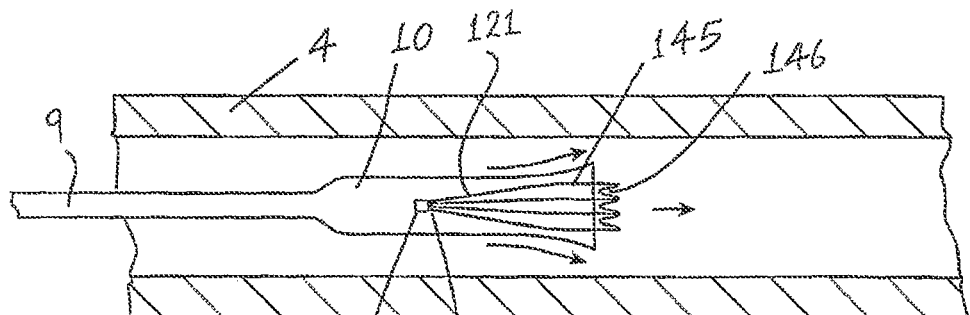
FIGS. 40 to 44 are partially cross-sectional, side views of the filter of FIGS. 39(a) and 39(b), in use.
Figure 41:
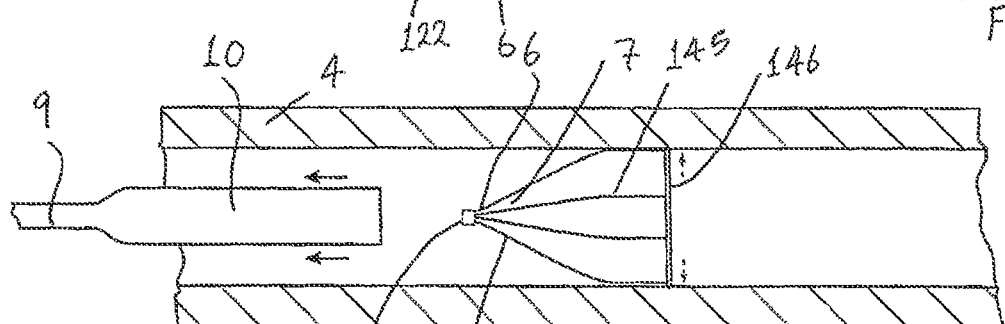
Figure 42:
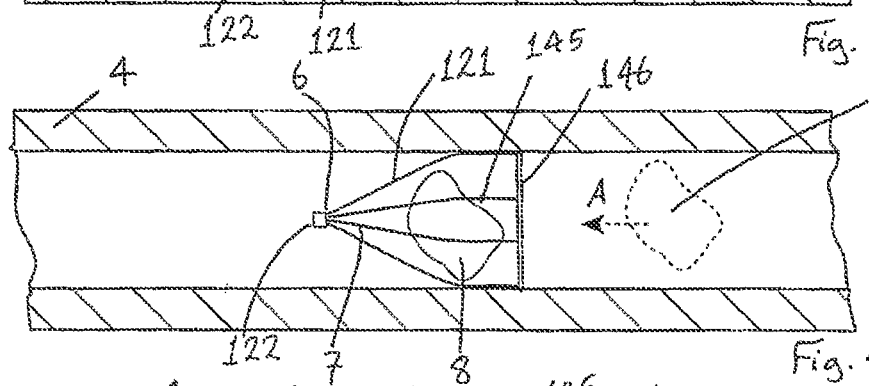
Figure 43:
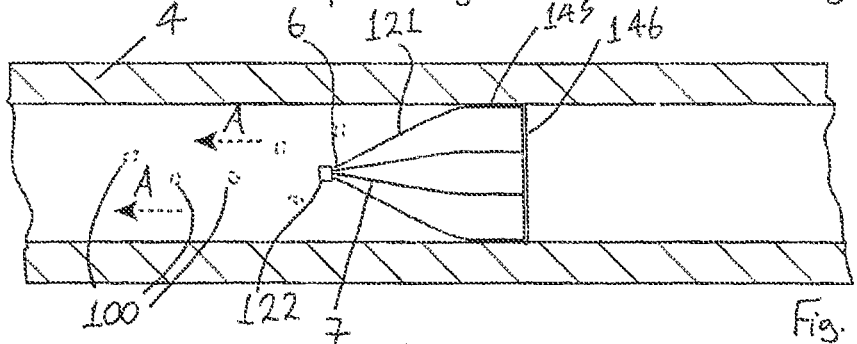

In this case the support hoop 146 comprises a wire element 147 which extends circumferentially in a sinusoid pattern in the collapsed delivery configuration (FIG. 39(a)), and which extends circumferentially in a plane in the expanded deployed configuration (FIG. 39(b)).

As illustrated in FIGS. 40 to 44, the filter 145 may be delivered to the desired location in the inferior vena cava 4 and deployed at the desired location using the delivery catheter 9 in a manner similar to that described previously with reference to FIGS. 1 to 9.

Figure 44:
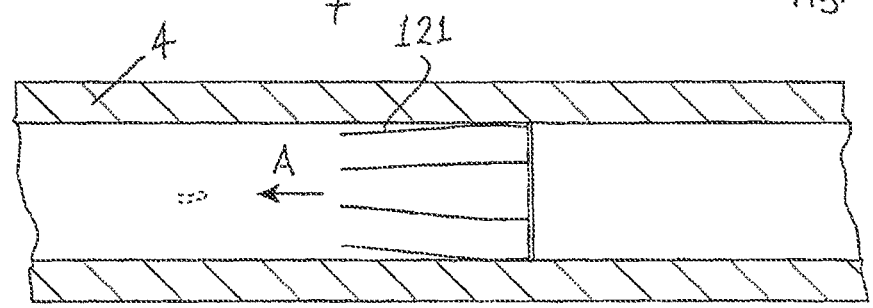
Figure 44B:
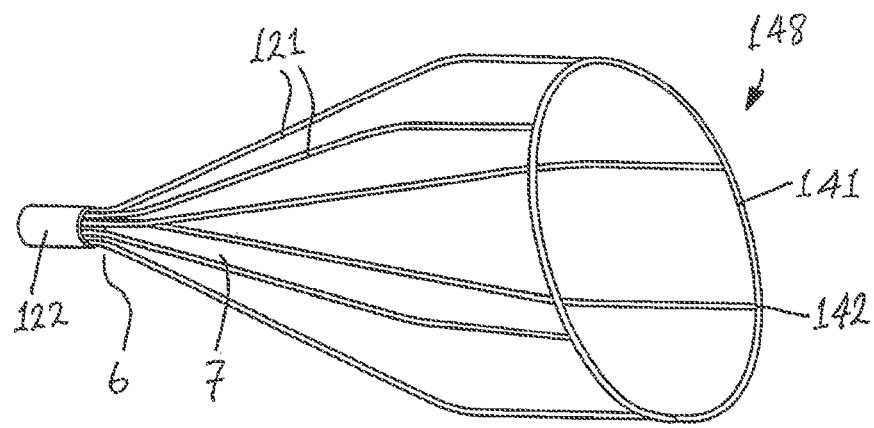
FIGS. 44(a) and 44(b) are views similar to FIGS. 39(a) and 39(b) of another vascular filter according to the invention.
Figure 44A:
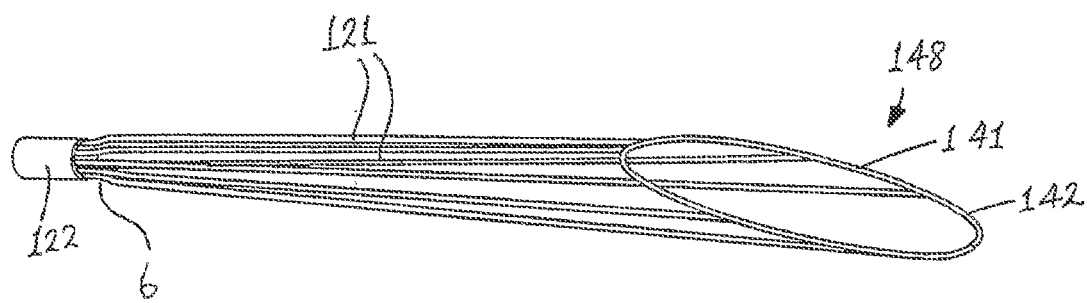

Referring to FIGS. 44(a) and 44(b) there is illustrated another vascular filter 148 according to the invention, which is similar to the vascular filter 140 of FIGS. 37 to 39, and similar elements in FIGS. 44(a) and 44(b) are assigned the same reference numerals.

In this case the support hoop 141 comprises the wire element 142 which extends circumferentially in a plane. In the collapsed delivery configuration the plane of the support hoop 141 is inclined relative to a plane perpendicular to the longitudinal axis of the inferior vena cava 4 (FIG. 44(a)). In the expanded deployed configuration, the plane of the support hoop 141 may or may not be inclined relative to the plane perpendicular to the longitudinal axis of the inferior vena cava 4 (FIG. 44(b)).

Figure 45:
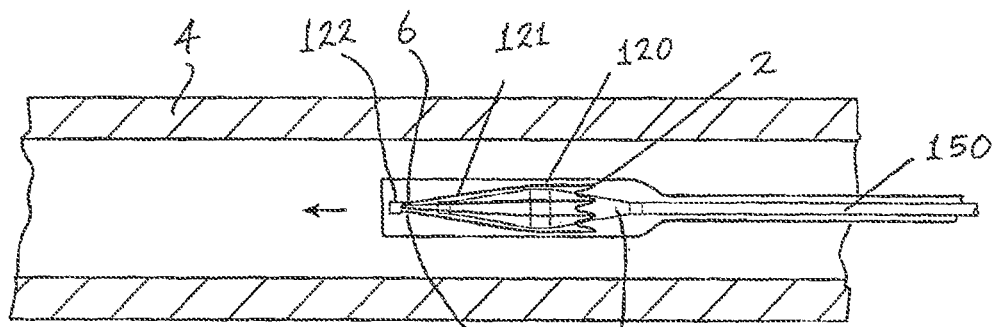
FIGS. 45 to 49 are partially cross-sectional, side views of the filter of FIGS. 27 and 28, in use.
Figure 46:
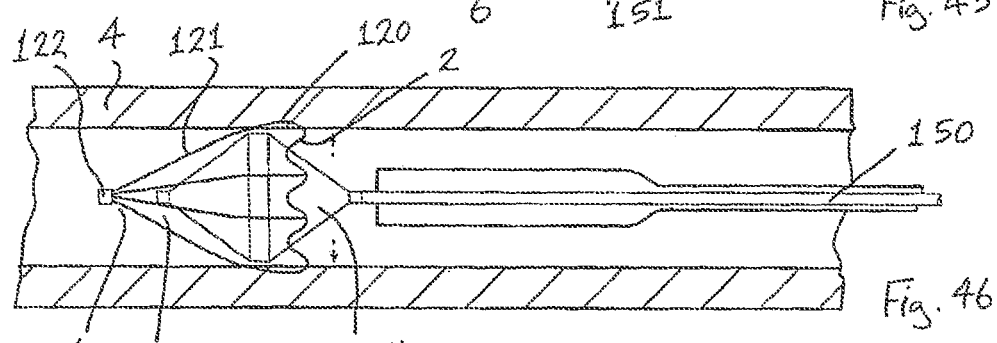
Figure 47:
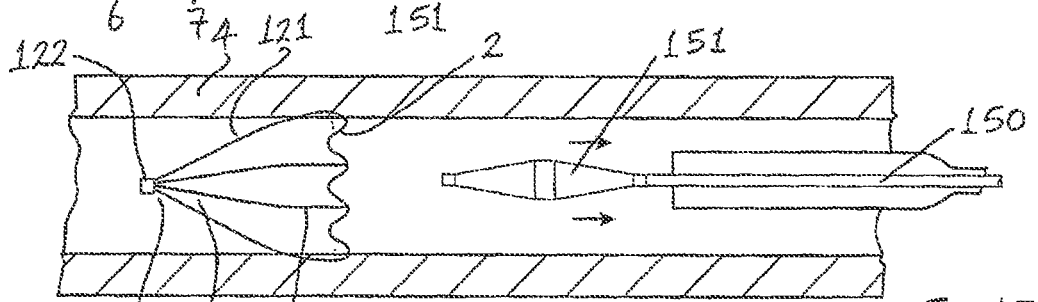

Alternatively, the filter 120, as described previously with reference to FIGS. 27 to 30, may be delivered to the desired location in the inferior vena cava 4 and deployed at the desired location using another delivery catheter 150 (FIGS. 45 to 49). The delivery catheter 150 comprises a balloon member 151 which is inflatable from a collapsed delivery configuration (FIG. 45) to an expanded deployed configuration (FIG. 46), and deflatable from the expanded deployed configuration to the collapsed delivery configuration (FIG. 47).

In use the support hoop 2 and the six capture arms 121 are collapsed to the delivery configuration, and mounted around the balloons member 151. The delivery catheter 150 is advanced through the inferior vena cava 4 until the collapsed filter 120 reaches the desired location in the inferior vena cava 4 (FIG. 45). The balloon member 151 is then inflated to move the support hoop 2 and the capture arms 121 from the collapsed delivery configuration to the expanded deployed configuration (FIG. 46). In the deployed configuration, the support hoop 2 exerts a radially outward force on the internal wall of the interior vena cava 4 to support the capture arms 121 in the desired position in the inferior vena cava 4.

The balloon member 151 is deflated from the expanded deployed configuration to the collapsed delivery configuration, and the delivery catheter 150 is withdrawn (FIG. 47).

Figure 48:
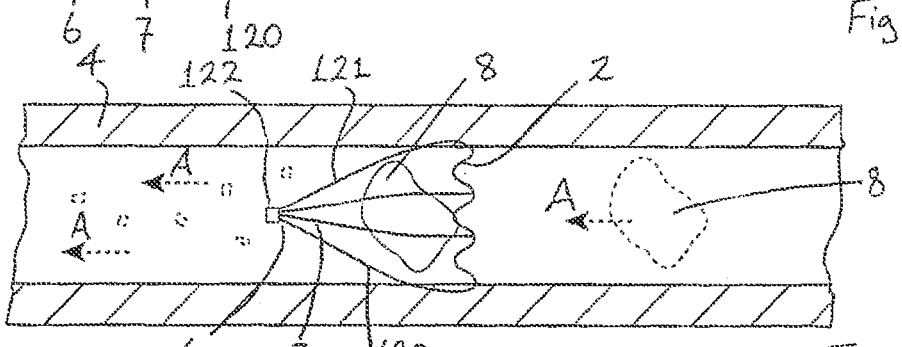
Figure 49:
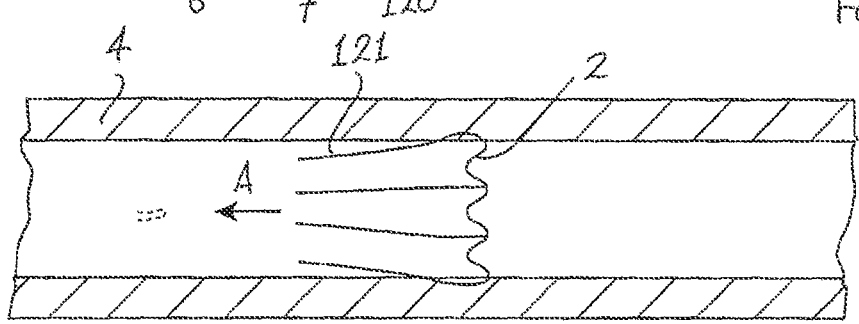

In the event of thrombus 8 passing through the inferior vena cava 4 towards the heart and the lungs, the thrombus 8 will be captured in the capture region 7 of the filter 120 (FIG. 48). The captured thrombus 8 will gradually be broken down by the body into smaller size particles, which significantly reduce the risk of embolism.

Due to the biodegradable/bioabsorbable material of the holder tube 122, the holder tube 122 will eventually biodegrade/bioabsorb (FIG. 49), which enables the capture arms 121 to move from the capturing configuration to the open configuration. The support hoop 2 and the capture arms 121 remain in the inferior vena cava 4.

FIGS. 45 to 49 illustrate the balloon expandable vena cava filter 120 which has non shape memory metals or polymers. The filter 120 is mounted onto the balloon catheter 150.

The distal tip of the balloon may be inverted to minimise space used by the balloon.

A tip marker may be incorporated to allow guidewire pull back for deployment.

Figure 51:
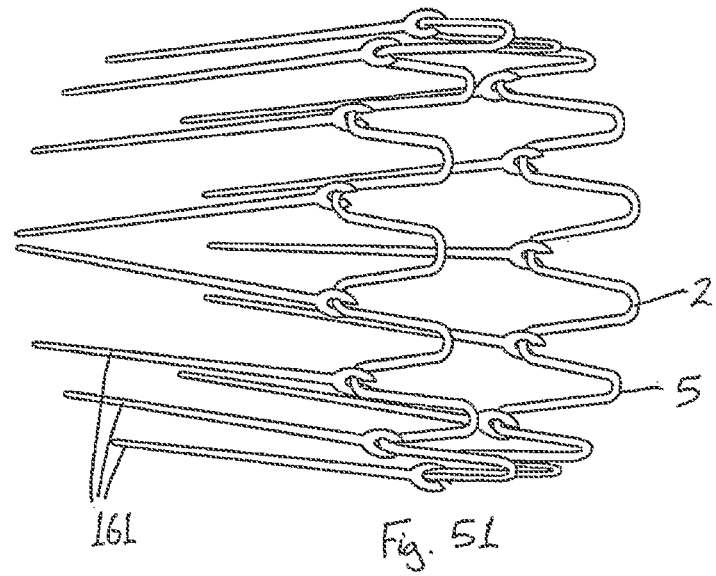
FIGS. 50 and 51 are views similar to FIGS. 27 and 29 of a further vascular filter according to the invention.
Figure 52:
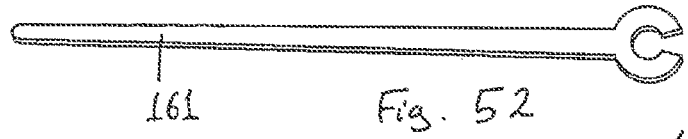
FIG. 52 is an isometric view of one of the capture members of the filter of FIGS. 50 and 51.
Figure 50:
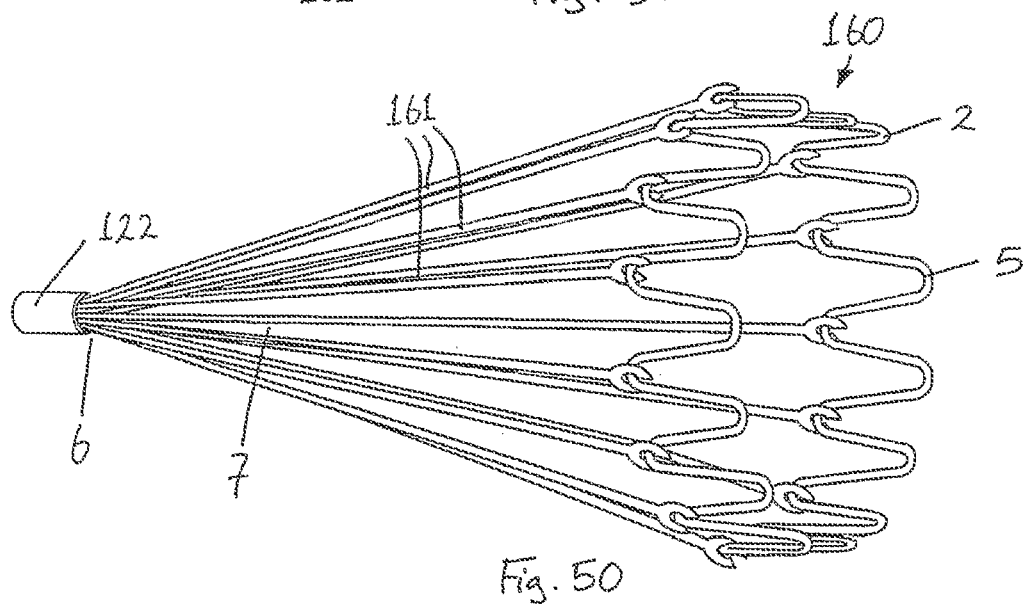

FIGS. 50 to 52 illustrate another vascular filter 160 according to the invention, which is similar to the similar filter 120 of FIGS. 27 to 30 and 32 to 36 and similar elements in FIGS. 50 to 52 are assigned the same reference numerals.

In this case, each capture arm 161 is formed separately from the support hoop 2 and is attached to the support hoop 2 in a snap-fit arrangement.

FIG. 52 illustrates the moulded element 161 which is snap fitted to the sinusoidal wire 5.

Alternatively, the capture arms 161 may be of polymer and may be welded to the degradable holder tube 122 at the apex 6. The capture arm parts 161 are biased towards the open position.

Figure 52E:
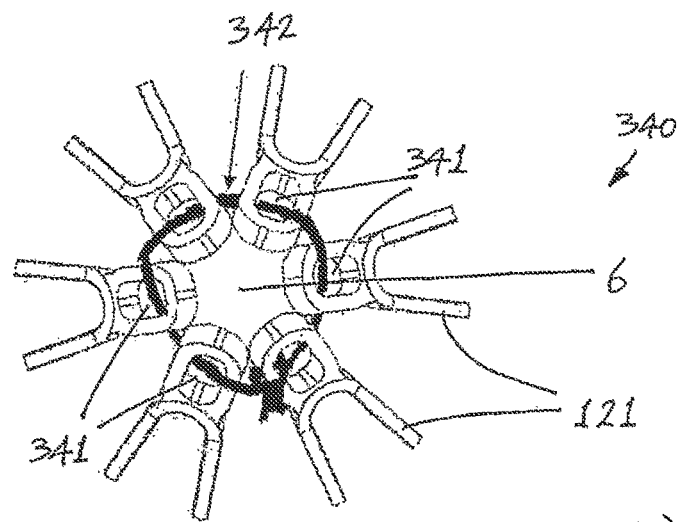
FIG. 52(e) is as enlarged, end view of part of the filter of FIG. 52(c)
Figures 52F, 52G:
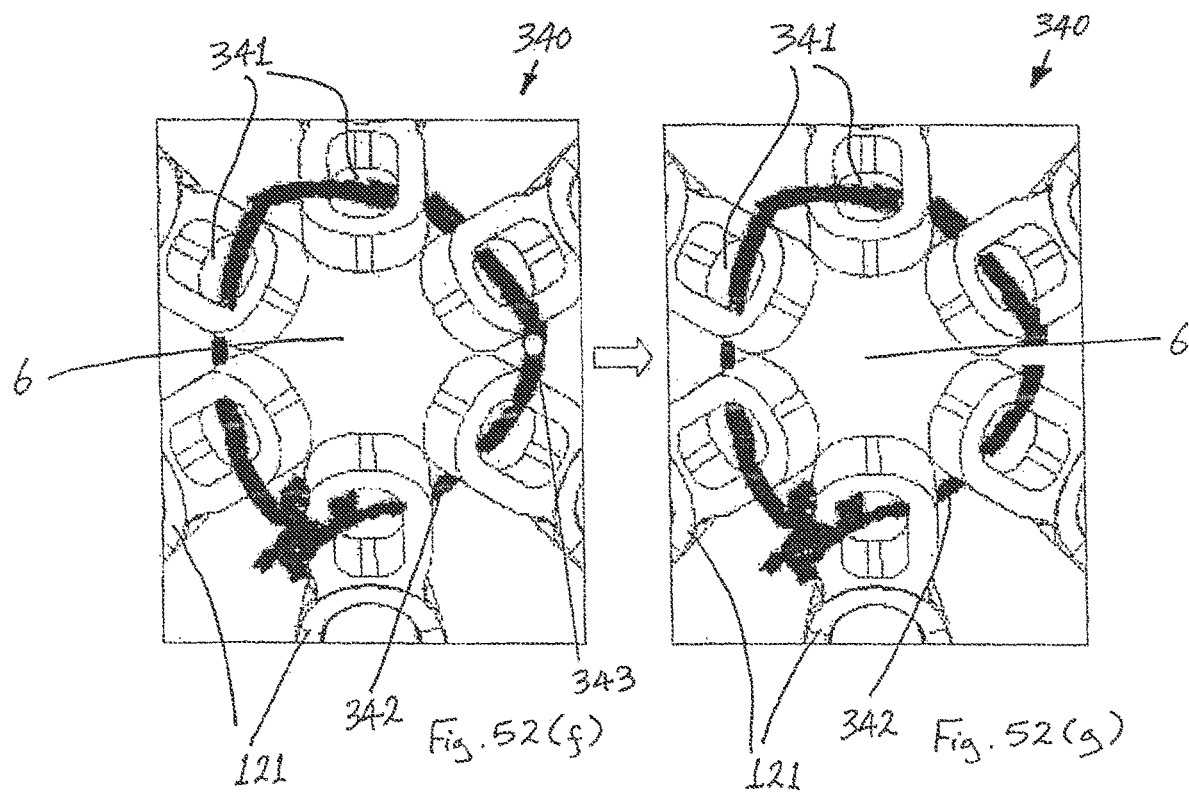
FIGS. 52(f) and 52(g) are end views of the filter of FIG. 52(e), in use.
Figure 52H:
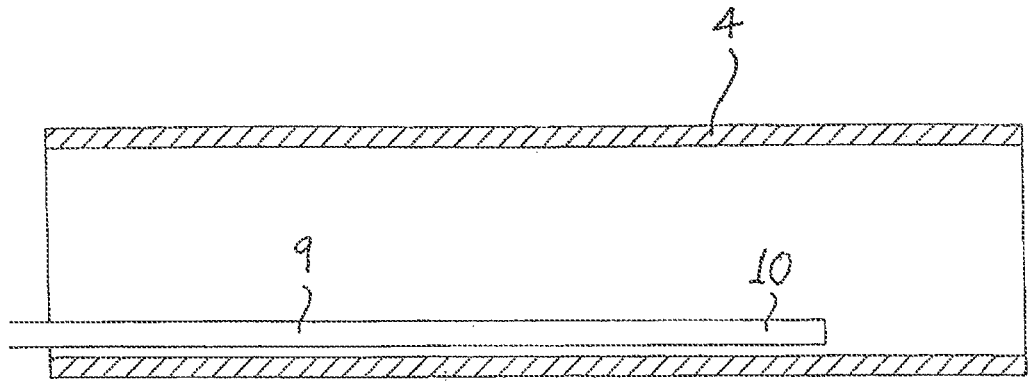
FIGS. 52(h) to 52(n) are partially cross-sectional, side views of the filter of FIG. 52(a), in use.
Figure 52I:
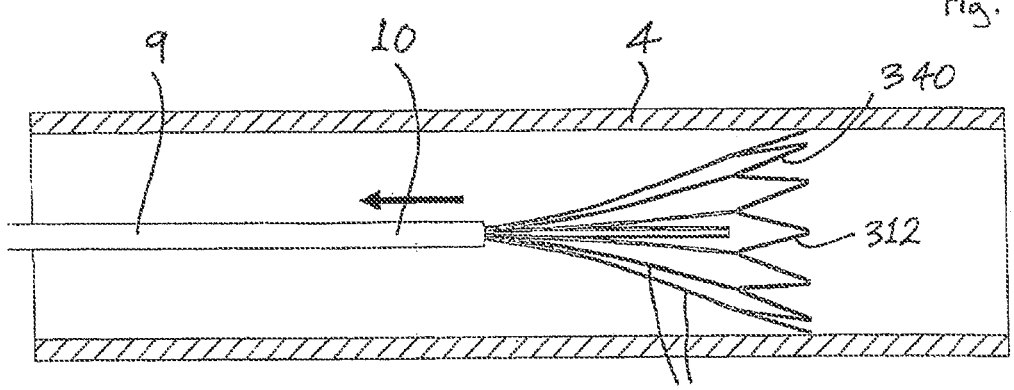
Figure 52J:
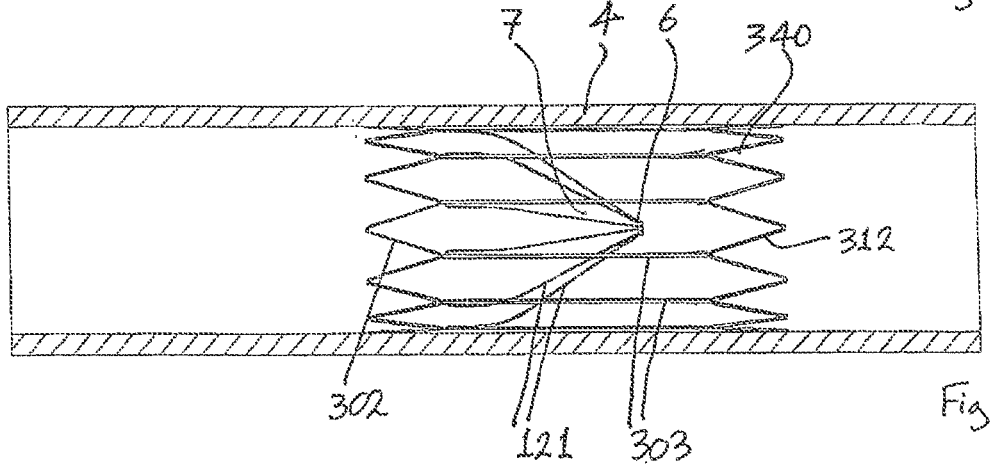
Figure 52K:
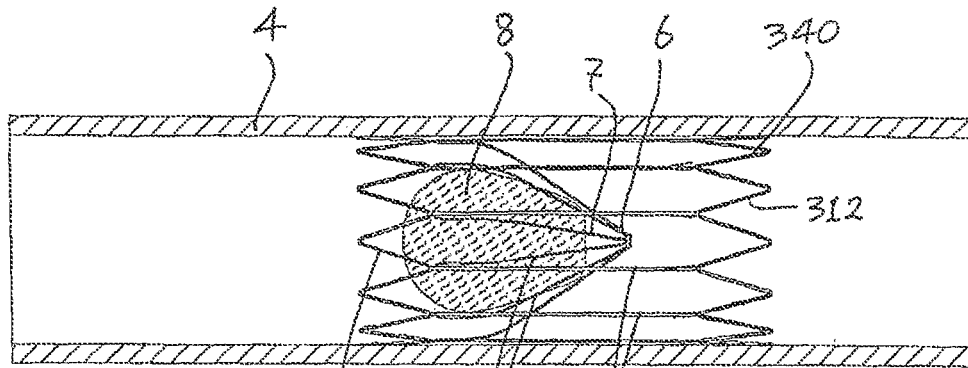
Figure 52L:
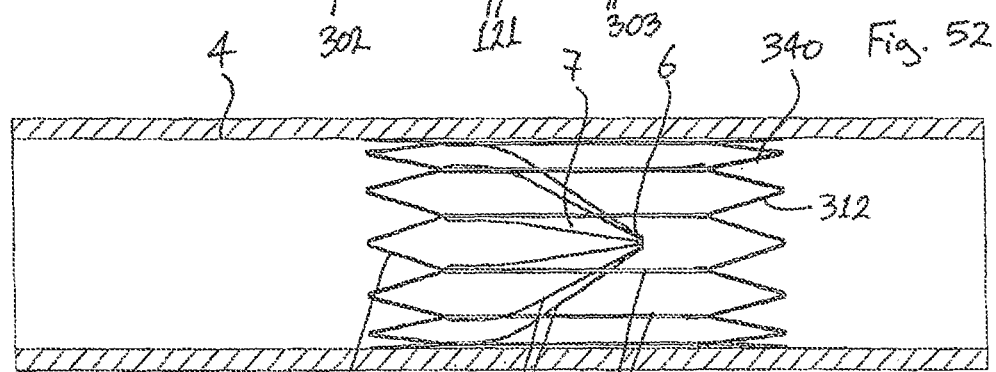
Figure 52M:
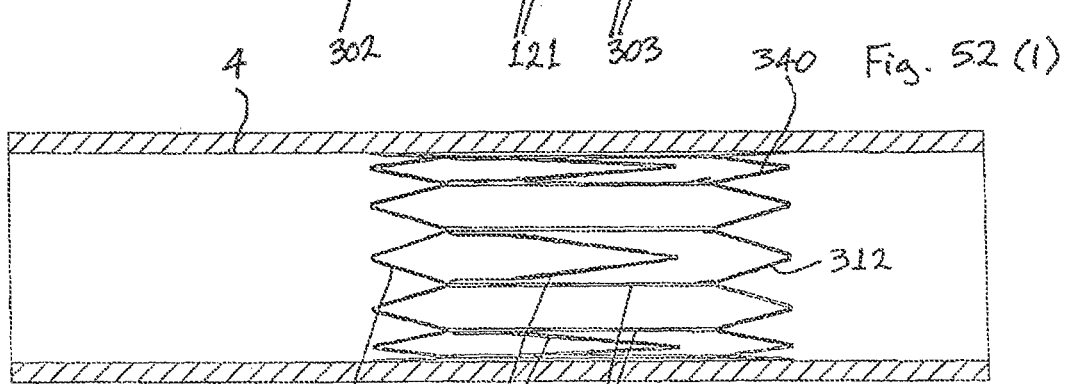
Figure 52N:
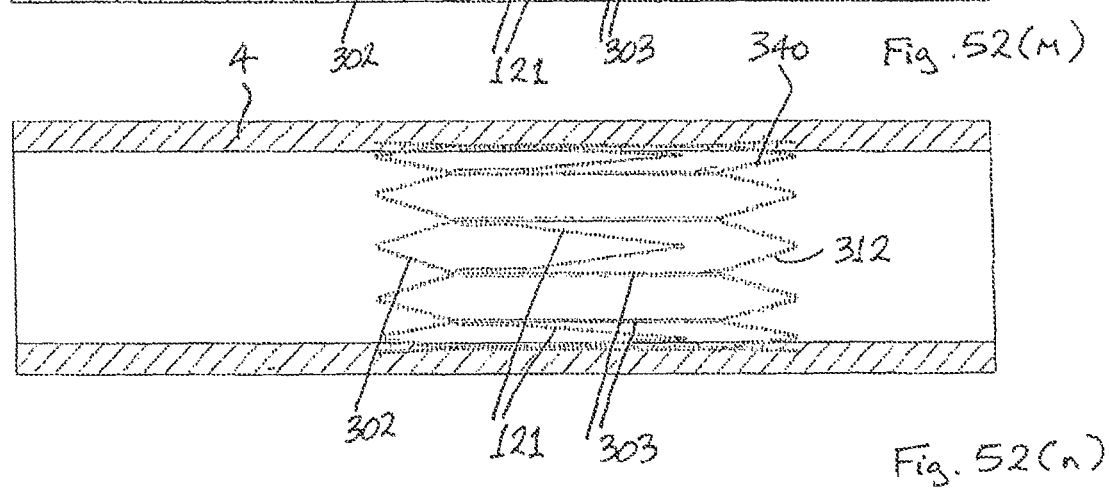

In FIGS. 52(a) to 52(n) there is illustrated vascular filter 340 according to the invention, which is similar to the vascular filter 120 of FIGS. 27 to 30 and 32 to 36, and similar elements in FIGS. 52(a) to 52(n) are assigned the same reference numerals.

In this case the filter 340 comprises a proximal support hoop 302, a distal support hoop 312, a plurality of support struts 303, and a plurality of biodegradable/bioabsorbable barbs 301, similar to those described previously with reference to FIGS. 26(a) to 26(g).

An opening 341 is provided at the distal end of each of the capture arms 121, and a suture 342 extends through the opening 341 to hold the capture arms 121 in the capturing configuration.

The suture 342 is of a biodegradable/bioabsorbable material. The suture 342 comprises an opening 343 through the wall of the suture 342. The opening 343 reduces the tensile strength of the suture 342. In this manner the suture 342 is provided with a predetermined failure point to control biodegrading/bioabsorbing of the suture 342.

FIGS. 52(a) to 52(n) illustrate the apex filter design. FIG. 52(b) illustrates the filter element 121, the crown elements 302, 312, and the connecting elements 303. While shown in a straight configuration, the elements 303 connecting the cranial and caudal ends may include curved or angled elements. Such configuration may provide reduced lateral stiffness. Generally, the elements 303 will nest together for delivery in the delivery system prior to deployment in the vena cava 4.

The apex design comprises the Nitinol frame 302, 312, 203, 121 and the small bioabsorbable element 342. The Nitinol frame is designed with thin elements that allow the device 340 to assume three separate configurations during its use:

1. Delivery configuration.
2. Filter configuration
3. Open configuration

The component has a zigzag type support feature at both its ends 302, 312 referred to in this specification as a crown, which allows the device 340 to be crimped or reduced in diameter so that it can be delivered through the vascular system in a catheter of much smaller diameter than the inferior vena cava 4.

The elastic energy in the deformed crowns 302, 312 enable the device 340 to expand to the vessel diameter. The component is designed so these crowns 302, 312 exert outward radial pressure against the internal wall of the vena cava 4 within the range of vessel typically encountered.

The two sets of crowns 302, 312 are linked by connecting elements 303, and originating from the caudal ends of these connecting elements 303 are thin filter element 121 which have a V-shape. These filter elements 121 can be mechanically deformed and retained in a central conical shape in order to create a filter configuration.

The component is desired so that the crown elements 302, 312 and connecting elements 303 are relatively stiff versus the filter elements 121, making the outer profile of the component substantially cylindrical when the filter elements 121 are deformed inward. This ensures that the crown elements 302, 312 and connecting elements 303 remain in contact with the wall while the device 340 is in the filter configuration promoting tissue ingrowth and minimising the risk of complications with vena cava filters such as migration and perforation.

The filter elements 121 are held together by means of the filament 342 made from a small volume of bioabsorbable material. The material has a known degradation profile such that it has sufficient strength to retain the metal filter elements 121 in the filtering configuration while the patient is at risk of a large embolus passing through the vena cava 4. Once the treatment period has passed, the filament 342 will have degraded sufficiently for the elastic force of the metal filter elements 121 to break the filament 342 and expand outward.

The filament 342 is tied through small eyelet features 341 at the end of the filter elements 121 and a knot is formed around one filter 121 such that once the filament 342 breaks it stays attached to that filter element 121.

Once the filter elements 121 become free the device 340 assumes its open configuration. The filter element 121 spring back to the vessel wall and exert sufficient pressure to promote endothelial covering and encapsulation in tissue, negating any long term complications associated with obstructing the blood flows in the vena cava 4.

In order to ensure that no migration takes place small barbs 301 are located at the cranial end of the connecting elements 303. They have sharp edges that are angled so anchor into the vessel tissue. The design features barbs 301 which may face in either direction, or may have separate barbs 301 facing in opposite directions.

FIGS. 52(*a*) to 52(*n*) illustrate the concept for the convertible blood vessel filter 340 where the device 340 has three configurations, the delivery configuration, filter configuration and the open configuration.

The filter configuration is used to trap thrombus while a patient may be at risk of a thromboembolic event; once the risk has passed the device 340 can then be converted to the open configuration which no longer disrupts blood flow.

The filter configuration is achieved by mechanically deforming the elements 121 of the device 340 and securing these filter elements 121 together at a point within the blood vessel. The filter elements 121 are held by the bioabsorbable securement feature 342, which may be released to allow the elements 121 to revert back to the open configuration.

In the filter configuration, there is sufficient radial pressure and vessel contact to prevent the device 340 from migrating due to movement of surrounding organs and/or the forces of blood flow. However the radial pressure is not sufficiently high to cause perforation of the blood vessel 4.

In the open configuration all elements of the implanted device 340 exert radial pressure against the blood vessel wall promoting tissue ingrowth.

This is achieved by having the device 340 that has a substantially cylindrical outer profile with sufficient mechanical stiffness to maintain the cylindrical outer profile when the filter elements 121 of low mechanical stiffness are deformed centrally. The substantially cylindrical outer profile allows the device 340 to have significant vessel contact over a large area in both the open and filter configurations substantially reducing the risk of clinical issues such as perforation, migration and tilting.

The device 340 is constructed of a superelastic metal or polymer. In one embodiment the device is constructed of Nitinol.

In one embodiment the device 340 is one piece cut from a laser machined tube, expanded and heat set. In another embodiment the device 340 is an assembly of more than one part from either the same material or from differing superelastic materials.

Having a substantially cylindrical outer profile provides a significant advantage in terms of deployment. As the device 340 exits the delivery system, the initial portion of the device 340 will contact the vessel wall prior to full device exiting of the delivery system. This allows for accurate placement of the device 340; as illustrated in FIG. 52(*i*).

In addition it also results in a self centering device 340 preventing tilting and allowing for the maximum clot trapping efficiency.

As the biodegradable members degrade, the degradation products move into the bloodstream and in themselves, if they are large enough, could pose a risk to the patient of pulmonary embolism. It is thus beneficial to have a device that utilises only a small volume of bio-resorbable polymer. Ideally a short length of filament in the order of 1-10 cms of diameter>0.4 mm, more ideally less than 0.3 mm, even more ideally less than 0.2 mm may be used.

Another approach to managing the volume of degradation products being released into the bloodstream at any time interval is taught herein by means of controlling the filter element dimensions and thus the time at which those products are released.

FIG. 52(*e*) illustrates the bioabsorbable element 342 which is configured to break at some point away from the knot. The element 342 is knotted around the frame 121. The element 342 remains connected to one element 121 of the frame after the filament 342 breaks.

The suture 342 may have a particularly small volume of bioabsorbable material. For example the suture 342 may have a diameter of less than 0.4 mm, ideally less than 0.3 mm, more ideally less than 0.2 mm.

By minimising the amount of bioabsorbable material that embolises and enters the blood stream, this reduces the risk of clinical complications. The filament material 342 is tied to the ends of the capture elements 121 in such a way that when it breaks the filament 342 remains tied to one of the capture elements 121 and becomes apposed to the vessel wall. This results in the bioabsorbable material 342 becoming encapsulated in tissue and absorbing therein. This may be achieved by knotting the suture 342 around one of the arms 121 as shown in FIG. 52(*e*). The suture 342 will break at a point away front the knot and release the capture element arms 121 bringing the suture 342 with one of the arms 121.

Introducing a point 343 along the suture 342 that is more susceptible to biodegradation is beneficial with this type of design. This may be achieved by having the region 343 that has a lower cross sectional area than the remainder of the filament 342.

In one embodiment this area of reduced cross section is achieved by lasering a small hole 343 through the filament material 342. Ideally the diameter of the hole 343 would be less than 0.0.0.1 mm. More ideally the diameter of the hole 343 would be 0.0.0.05 mm.

FIG. 52(*f*) illustrates the small hole 343 machined in the filament 342 to create the controlled break area.

The filter elements 342 may have multiple microscopic holes or notches drilled of formed therein to provide a locus for failure away from the joins or knots. This may be beneficial in that the location of eventual failure of the elements 342 is known. Varying the size of the holes will allow the time to failure for each element 342 to be controlled individually. Larger holes will result in a shorter time to failure. This may be beneficial in allowing the timing of degradation products being released into the bloodstream to be controlled. Alternatively, varying the diameter of the elements 342 to sequentially larger diameters will allow similar control over the time to failure of the filter elements 342.

The reduced cross section may alternatively be achieved by softening the material with heat and creating a 'necked down' region which has a reduced cross sectional area.

The convertible filter 340 anchors securely at its deployment site and minimises risk of migration. The filter 340 incorporates the small sharp barbs 301 facing either direction which add fixation points for the device 340 and combined with the radial force of the design, minimise any risk of migration. The barbs 301 may be made of a bioabsorbable material which degrades and metabolises after the device 340 has been encapsulated in tissue. This will prevent any long term effects due to erosion and/or perforation of the vena cava 4 caused by the barb 301.

Suitable bioabsorbable materials for a bioabsorbably barb 301 and/or for the filter filament 342 include:

Poly(p-dioxanone);

Poly(L-Lactide-co-e-Caprolactone); Ideally the mole percentage of L-lactide monomer would be in the range of 60% to 80%. More ideally the mole percentage of L-lactide monomer would be in the range of 65% to 75%. Poly(glycolide-co-trimethylene carbonate);

Ideally the mole percentage of L-lactide monomer would be in the range of 60% to 80%. More ideally the mole percentage of L-lactide monomer would be in the range of 65% to 75%.

Poly(hydroxy butyrate);

Poly(L-lactide-co-glycolide);

Ideally the mole percentage of L-lactide monomer would be greater than 70%.

More ideally the mole percentage of L-lactide monomer would be greater than 80%.

More ideally the mole percentage of L-lactide monomer would be greater than 90%.

The design of FIGS. 52(a) to 52(n) provides a stent-like shape to the vena cava filter 340 giving it a cylindrical outer profile. This design prevents issues such as tilting and perforation and allows for accurate deployment within the vessel 4. The frame design allows the filter elements 121 to be deformed centrally without affecting the cylindrical outer profile and once the risk period for thromboemboli has passed allows the filter 121 to spring back to a position apposed to the vessel wall.

The bioabsorbable element 342 stays attached to the frame 121 after opening. Controlling the break up of the bioabsorbable element 342 and minimising the amount of material that embolises may be achieved by tying the filament 342 around one filter element end. Therefore, once the element 342 breaks, it will remain attached to the frame 121 and become encapsulated in the vein wall along with the frame 121. A controlled break point 343 may be added to the absorbable element 342 away from the knot by any of the means described herein.

Having barbs 301 that are bioabsorbable offers a significant advantage in that they are only required in the short-term and once the frame becomes encapsulated in the vein wall they will no longer be required thus preventing any potential long-term erosion effects of having the barbs 301 on the frame.

FIG. 52(h) illustrates the vena cava 4 being accessed transluminally using the delivery catheter 9. FIG. 52(i) illustrates the vena cava filter 340 being deployed by pulling back the delivery catheter sheath 10. FIG. 52(j) illustrates the device 340 deployed filtering thromboemboli within the vena cava 4. FIG. 52(k) illustrates the device 340 capturing a large clot 8 that may have caused a pulmonary embolism. FIG. 52(l) illustrates the filter 340 in situ after the blood's own natural lysing processes have broken down the clot 8 over time. FIG. 52(m) illustrates that once the threat of pulmonary embolism has passed, the bioabsorbable retainer 342 breaks down and allows the filter arms 121 to become apposed to the wall. FIG. 52(n) illustrates that over time the frame 340 becomes encapsulated in tissue.

Figure 53:
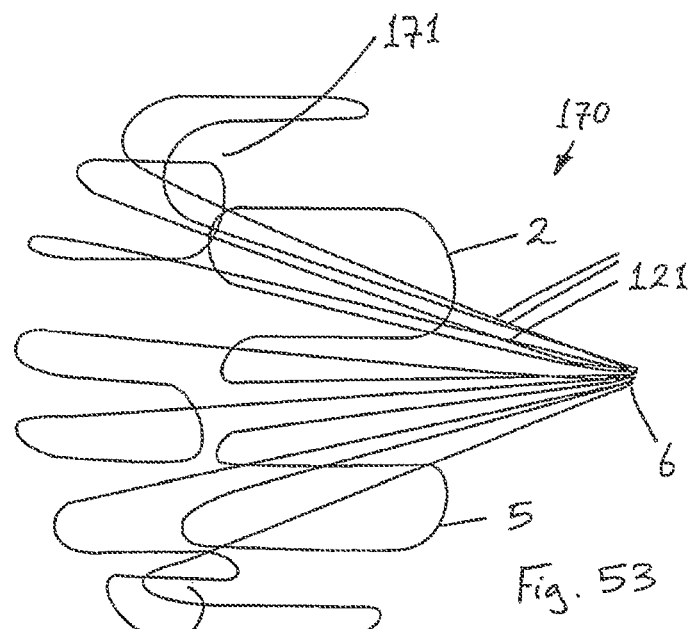
FIG. 53 is an isometric view of another vascular filter according to the invention.
Figure 54:
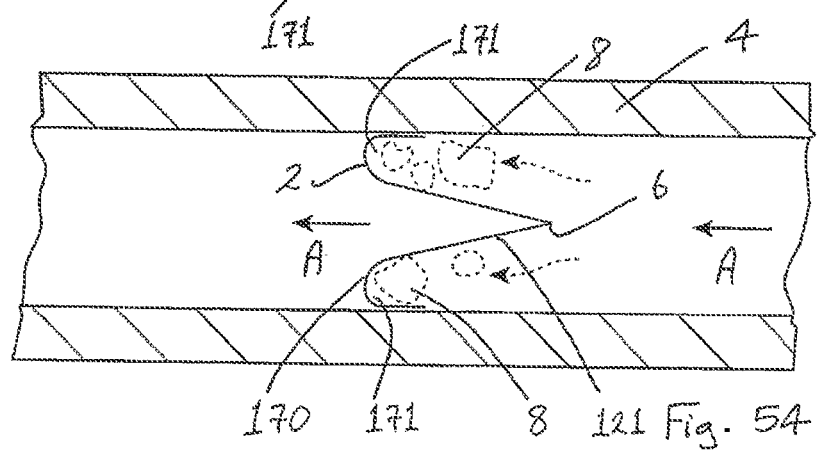
FIG. 54 is a partially cross-sectional, side view of the filter of FIG. 53, in use.

Referring to FIGS. 53 and 54 there is illustrated another vascular filter 170 according to the invention, which is similar to the vascular filter 120 of FIGS. 27 to 30 and 32 to 36, and similar elements in FIGS. 53 and 54 are assigned the same reference numerals.

In this case when the filter 170 is deployed in the inferior vena cava 4, the capture arms 121 extend in the direction opposite to the direction of blood flow A through the inferior vena cava 4 (FIG. 54). As a result, the capture arms 121 define an annular shaped capture region 171 located in the region of the internal wall of the inferior vena cava 4.

FIG. 53 illustrate the Nitinol sinusoid 2 and the inverted elements 121. This configuration acts to divert embolism 8 from the centre of the flow to be retained close to the side of the vessel 4. It creates a type of receiver region 171 to receive the thrombus 8.

Figure 55:
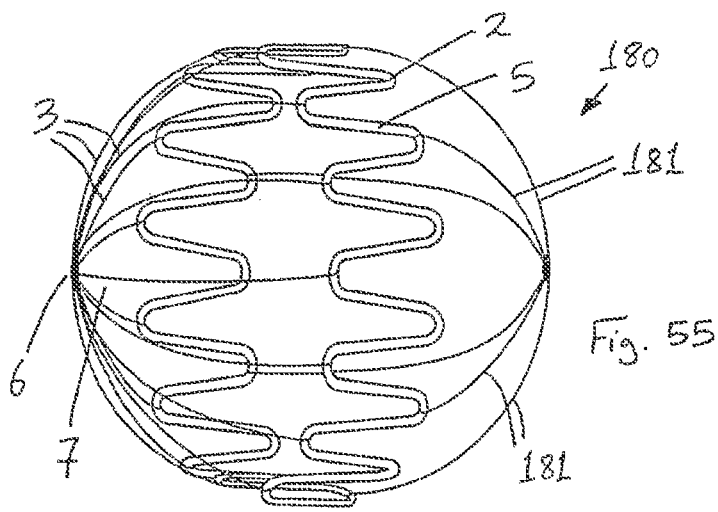

In FIG. 55 there is illustrated another vascular filter 180 according to the invention, which is similar to the vascular filter 90 of FIG. 23, and similar elements in FIG. 55 are assigned the same reference numerals.

In this case the filter 180 comprise six balance arms 181 extending from the support hoop 2 in the opposite direction to the capture arms 3. Each balance arm 181 is attached to the support hoop 2 by wrapping an end of the balance arm 181 around the wire element 5.

Each balance arm 181 is of a biodegradable and/or bioabsorbable material.

Each balance arm 181 extends in a curve. The convex portion of the curve faces radially outwardly.

In use, due to the biodegradable/bioabsorbably material of the balance arms 181, the balance arms 181 will eventually biodegrade/bioabsorb. Thus only the support hoop 2 will remain in the interior vena cava 4.

The filter 180 may be of varying porosity. More space may be provided in the distal sections. The filter 180 has a ball shape. There are no sharp edges on a ball. This may allow enhanced radial force on the vena cava wall for enhanced anchoring.

FIGS. 56 to 59 illustrate another vascular filter 190 according to the invention, which is similar to the vascular filter 120 FIGS. 27 to 30 and 32 to 36 and similar elements in FIGS. 56 to 59 are assigned the same reference numerals.

In this case the filter 190 comprises a plurality of support anchors 191 instead of the support hoop. A support anchor 191 is fixedly attached to a proximal end of each capture arm 121. Upon deployment of the filter 190 in the inferior vena cava 4, the support anchors 191 are embedded into the internal wall of the inferior vena cava 4 (FIG. 57). In this matter the support anchors 191 support the capture arms 121 in position relative to the wall of the inferior vena cava 4.

The biodegradable barbs 191 secure the filter device 190 at the time of implantation and are resorbed either fully or partially at the time of retrieval.

It is believed that use of the barbs 191 on permanent filters could reduce long term implantation problems.

It is believed that the use of bio-resorbable barbs on any implant could reduce long term implantation problems. In particular a barb could be over-moulded or formed onto any metallic or polymeric structure and formed into the desired shape to anchor it to the vascular or anatomical structure. Alternatively the barbs could be moulded, machined, or formed from pre-forms such as extruded tiles or rods. The benefits include the fact that after a period of time the barb would be absorbed and the irritation removed from the implant site. Barbs could be attached to the end of or any intermediate point that could come in contact with a blood vessel during implantation by means of endovascular or surgical treatment.

Referring to FIGS. 60 to 63 there is illustrated another vascular filter assembly according to the invention. The vascular filter assembly comprises a vascular filter 200 according to the invention and a retrieval catheter 202 for retrieving the filter 200 from a location in the inferior vena cava 4. The vascular filter 200 is similar to the vascular filter 190 of FIGS. 56 to 59, and similar elements in FIGS. 60 to 63 are assigned the same reference numerals.

In this case the support anchors 201 are shaped to facilitate removal from the internal wall of the inferior vena cava 4, upon application of a removal force C in a direction parallel to the longitudinal axis B-B of the inferior vena cava 4 (FIG. 62).

The retrieval catheter 202 comprises a hook 203 for engaging the holder tube 122 of the filter 200, and a reception space 204. The hook 203 is movable proximally relative to the reception space 204 to at least partially receive the filter 200 in the reception space 204.

In use, when it is desired to retrieve the deployed filter 200 from the interior vena cava 4, the retrieval catheter 202 is introduced into the inferior vena cava 4. The retrieval catheter 202 is advanced through the inferior vena cava 4 with the hook 203 within the reception space 204.

When the distal end of the retrieval catheter 202 is adjacent to the holder tube 122, the hook 203 is advanced distally out of the reception space 204 (FIG. 61) to engage the holder tube 122 of the filter 200. The hook 203 is then moved proximally which exerts a retrieval force C on the filter 200 in a direction parallel to the longitudinal axis B-B of the inferior vena cava 4. Due to the shape of the support anchors 201, this retrieval force C causes the support anchors 201 to be removed from the internal wall of the inferior vena cava 4 (FIG. 62). The filter 200 is therefore free to be moved proximally into the reception space 204 by moving the hook 203 proximally. The retrieval catheter 202 and the retrieval filter 200 are then withdrawn from the inferior vena cava 4.

FIG. 60 illustrates the directional barbs 201 for retrievability. The blood flow A acts to better embed the barbs 201 in the vessel wall. The retrieval system 203 pushes the barbs 201 downwards and away from the artery wall 4. These FIGS. are illustrated with four filtering arms 121 for schematic purposes only. It is intended that the invention may use any number of arms 121, for example up to a maximum of twenty for optimum entrapment of thrombo-embolism.

Figure 63B:
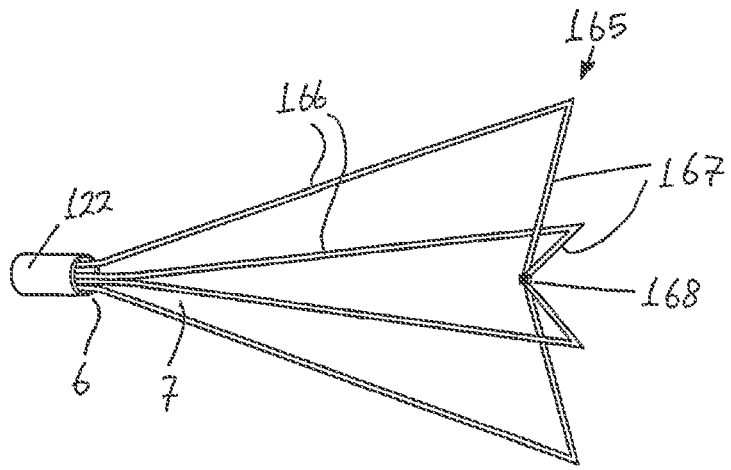
FIG. 63(b) is an isometric view of the filter of FIG. 63(a) in an expanded deployed configuration.
Figure 63C:
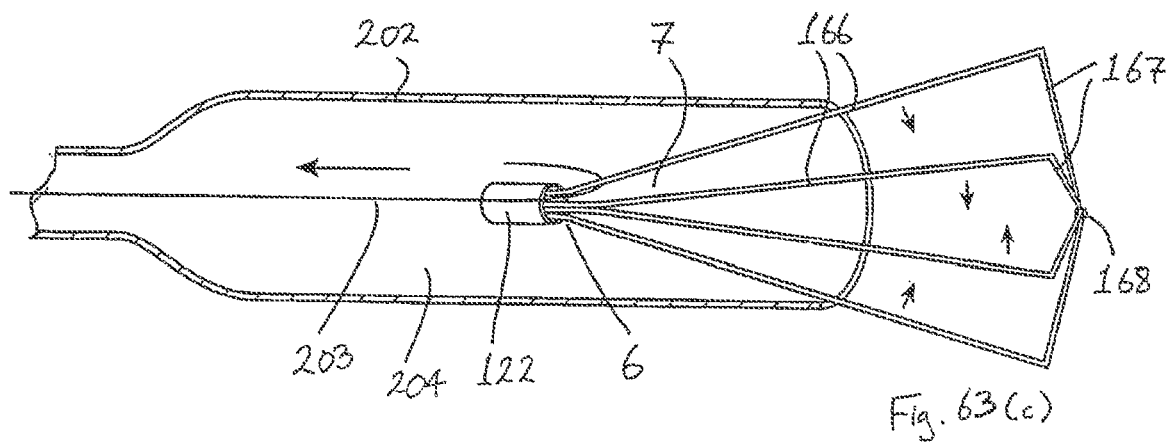
FIG. 63(c) is a partially cut-away, isometric view of the filter of FIG. 63(a), in use.
Figure 63A:
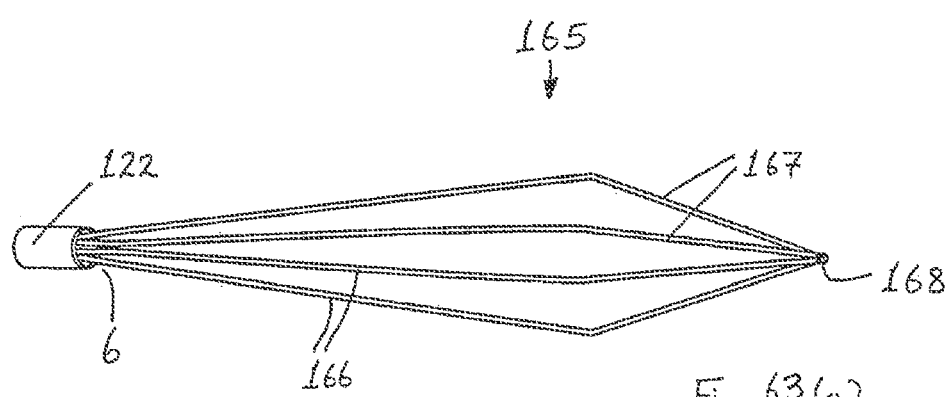
FIG. 63(a) is an isometric view of another vascular filter according to the invention in a collapsed delivery configuration.

Referring to FIGS. 63(a) to 63(c) there is illustrated another vascular filter assembly according to the invention. The vascular filter assembly comprises a vascular filter 165 according to the invention and the retrieval catheter 202. The vascular filter 165 is similar to the vascular filter 120 of FIGS. 27 to 30 and 32 to 36, and similar elements in FIGS. 63(a) to 63(c) are assigned the same reference numerals.

In this case the filter 165 comprises a plurality of support arms 167 instead of the support hoop. In the expanded deployed configuration, the support arms 167 extend radially outwardly from a hinge point 168 (FIG. 63(b)).

The holder tube 122 is not biodegradable/bioabsorbable in this case.

In use, the hook 203 is movable proximally relative to retrieval catheter 202 to cause the distal end of the retrieval catheter 202 to engage the capture arms 166. Further movement of the hook 203 proximally relative to the retrieval catheter 202 exerts a collapsing force on the capture arms 166 (FIG. 63(c)) to move the filter 165 from the expanded deployed configuration to the collapsed delivery configuration.

In FIG. 63(b) the ends 122, 168 are tethered. On retrieval, the cap 122 is engaged in the retrieval catheter 202, and the filter 165 is pushed down to elongate the filter 165 (FIG. 63(c)).

The elongation of the filter 165 pulls the capture arms 166 off the internal wall of the inferior vena cava 4.

The elongation of the filter 165 is based on hinge points at the vessel contact areas of the device. In another embodiment the retrieval may be accomplished from the proximal end by engaging the retrieval hoop at the proximal inverted apex. This embodiment would allow the implanted device to be retrieved from the femoral puncture site, which may be advantageous.

FIGS. 63(d) to 63(g) illustrate a further vascular filter 205 according to the invention, which is similar to the vascular filter 190 of FIGS. 56 to 59, and similar elements in FIGS. 63(d) to 63(g) are assigned the same reference numerals.

In this case the filter 205 is a removable filter. The support anchors 206 are biodegradable to facilitate retrieval of the filter 205 into the retrieval catheter 202 (FIG. 63(f)).

Figure 64:
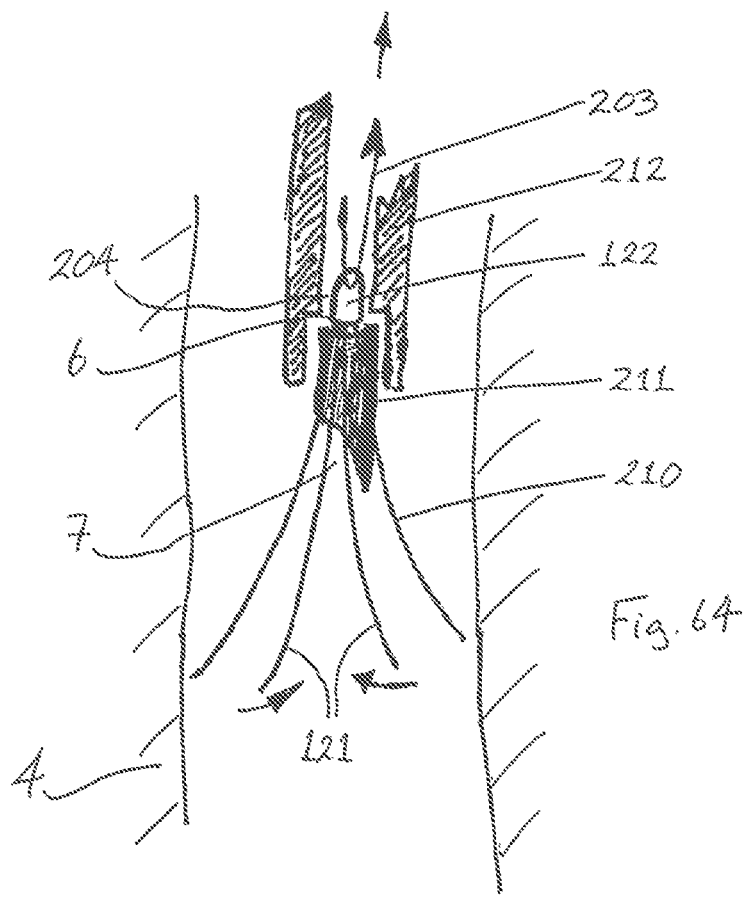
FIG. 64 is a partially cross-sectional, side view of another vascular filter according to the invention, in use.
Figures 65, 66:
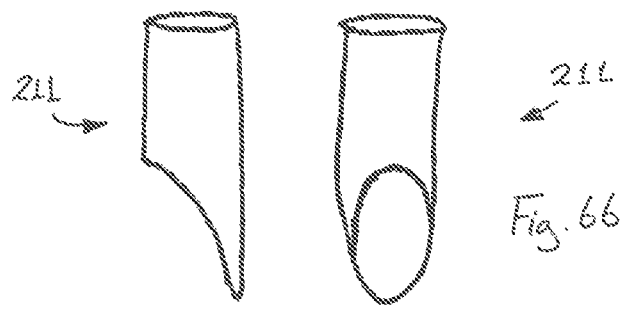
FIG. 65 is a side view of a part of the filter of FIG. 64.
FIG. 66 is a front view of the part of FIG. 65.

By looping individual legs with a torque controlled retrieval system, it will allow individual detachment of the barbs 201, as illustrated in FIGS. 64 to 66 by rotating the retrieval system such that it engages the filter arms individually and sequentially.

In FIGS. 64 to 66 there is illustrated another vascular filter assembly according to the invention. The vascular filter assembly comprises a vascular filter 210 according to the invention and a retrieval catheter 212. The vascular filter 210 is similar to the vascular filter 190 of FIGS. 56 to 59, and the retrieval catheter 212 is similar to the retrieval catheter 202 of FIGS. 60 to 63, and similar elements in FIGS. 64 to 66 are assigned the same reference numerals.

The retrieval system incorporates an actuation to aid the removal of the filter arms 121/anchors from the cava 4. Retrieval pulls back the central hub 122 and the filter arms 121 until the actuator 211 abuts the shoulder. Then due to the geometry, the individual arms 121 are selectively deflected in a sequence off the cava wall and towards the centre reducing the retrieval force required.

FIGS. 67 to 69 illustrate a further vascular filter 220 according to the invention, which is similar to the vascular filter 1 of FIGS. 1 to 9, and similar elements in FIGS. 67 to 69 are assigned the same reference numerals.

In this case the filter 220 comprises a wire element 221 which extends circumferentially and longitudinally in a spiral towards the apex 6 to define the conically shaped capture region 7.

The larger diameter turns of the spiral at the proximal end 222 of the filter 220 act as the support hoop to support the filter 220 in position relative to the internal wall of the inferior vena cava 4.

The small diameter turns of the spiral at the distal end 223 of the filter 220 act as the capture arm to capture thrombus 8 passing through the inferior vena cava 4.

As illustrated in FIGS. 68 and 69, the spiral configuration enables the filter 220 to be collapsed down in an efficient manner for delivery to the desired location in the inferior vena cava 4.

In this case the wire element 221 is not of a biodegradable or bioabsorbable material.

Referring to FIG. 70 there is illustrated another vascular filter 230 according to the invention, which is similar to the vascular filter 220 of FIGS. 67 to 69, and similar elements in FIG. 70 are assigned the same reference numerals.

In this case, when the filter 230 is deployed in the inferior vena cava 4, the wire element 221 extends towards the apex 6 in the direction opposite to the direction of blood flow A through the inferior vena cava 4. As a result the wire element 221 defines an annular shaped capture region 231 located in the region of the internal wall of the inferior vena cava 4.

The large diameter turns of the spiral at the distal end 231 of the filter 230 act as the support hoop.

FIGS. 67 to 70 illustrate coil vena cava filters 220, 230. The filter 220 has a conical section 223 and a mural section 222. The mural section 222 anchors the filter device 220 either with radial force or with barbs which may be bio-resorbable. The coil pitch decreases towards the apex 6. The coil may be concentric or non centric. The inverted coil design of FIG. 70 has its minimum pitch at the inversion.

The filter net 221 may absorb from inside to outside. The wall of the wire element 221 may be thicker at the outer section. The biodegradable filter 229 may absorb from the inner section out.

In FIGS. 71 to 76 there is illustrated another vascular filter assembly according to the invention. The vascular filter assembly comprises a vascular filter 240 according to the invention and a catheter 241. The vascular filter 240 is similar to the vascular filter 220 of FIGS. 67 to 69, and the catheter 241 is similar to the retrieval catheter 202 of FIGS. 60 to 63, and similar elements in FIGS. 71 to 76 are assigned the same reference numerals.

In this case wire element 221 defines an offset conically shaped capture region 242. When the filter 240 is deployed in the inferior vena cava 4, the apex 6 is offset from the longitudinal axis B-B extending through the centre of the inferior vena cava 4, and the capture region 242 is located in the region of the internal wall of the inferior vena cava 4.

The catheter 241 is employed as a delivery catheter to deliver the filter 240 to the desired location in the inferior vena cava 4 (FIGS. 74 and 75), and as a retrieval catheter to retrieve the filter 240 from the inferior vena cava 4 (FIG. 76). The hook 203 of the catheter 241 is engagable with corresponding notch 243 defined on the wire element 221. The hook 203 is rebated to collapse the filter 240 from the expanded deployed configuration (FIG. 72) to the collapsed delivery/retrieval configuration (FIG. 73), prior to moving the filter 240 proximally into the reception space 204, as illustrated in FIG. 76.

Retrieval of the filter 240 may be performed by pulling the filter device 240 into the catheter 241. This retrieval may be simplified by rotating the coil filter 240 in the direction of the helix, which tends to locally peel the coil 240 away from the intima. FIG. 76 illustrates the vessel wall with the coil 240 being rotated away.

Figure 78:
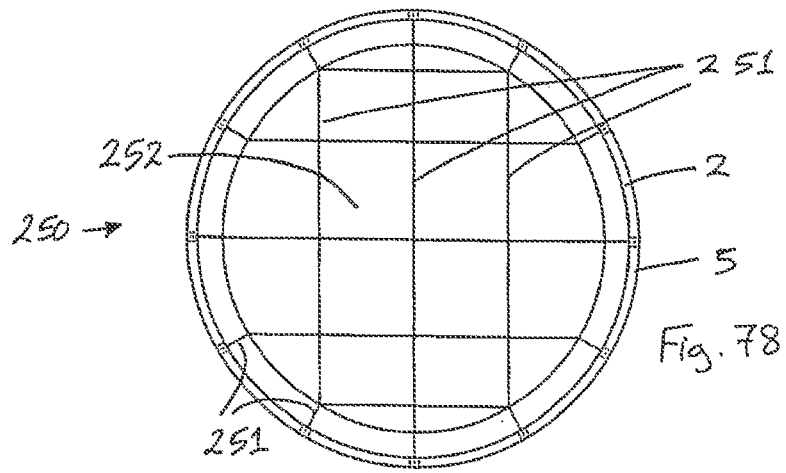
FIGS. 77 and 78 are views similar to FIGS. 1 and 2 of another vascular filter according to the invention.
Figure 77:
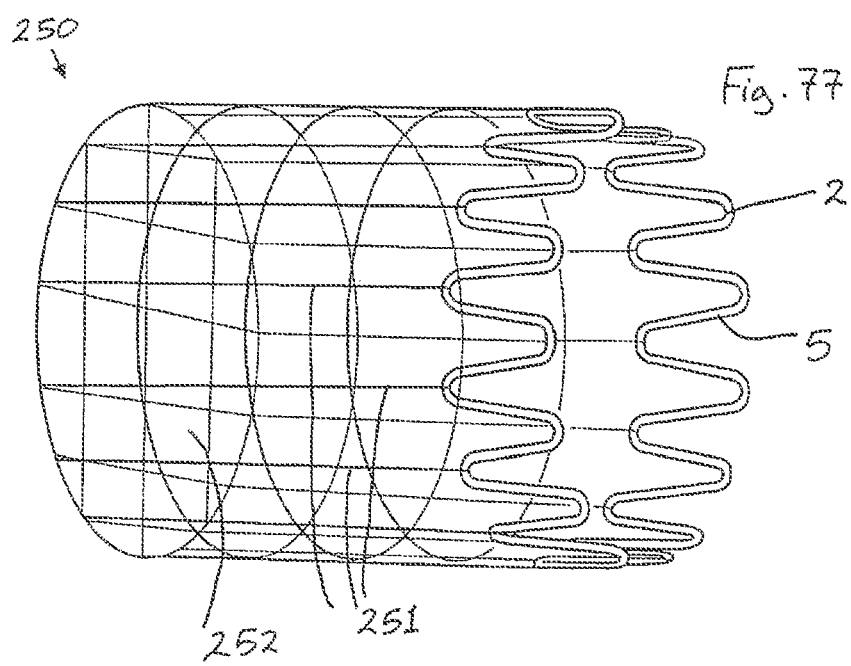

FIGS. 77 and 78 illustrate a further vascular filter 250 according to the invention, which is similar to the vascular filter 1 of FIGS. 1 to 9, and similar elements in FIGS. 77 and 78 are assigned the same reference numerals.

In this case the capture arms 251 extend in a cylindrical manner to define a cylindrically shaped capture region 252.

Figure 79:
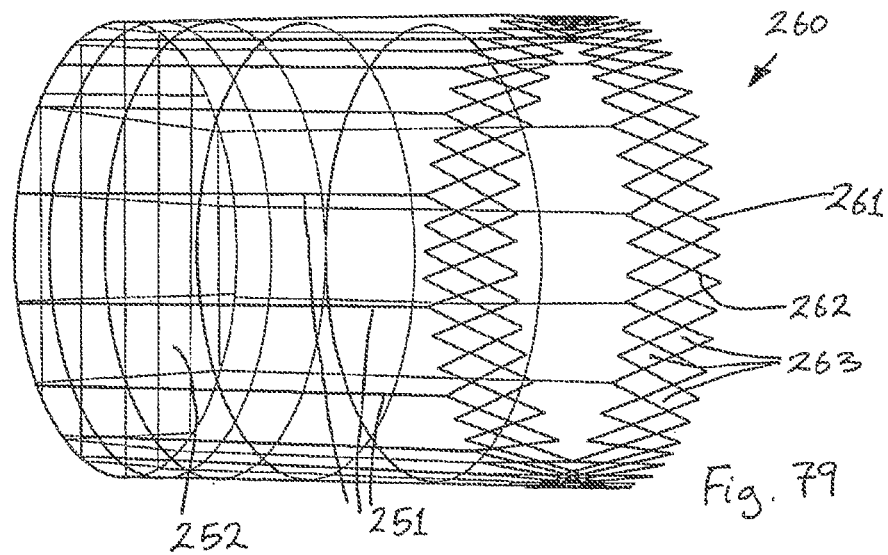
FIG. 79 is an isometric view of a further vascular filter according to the invention.

Referring to FIG. 79 there is limited a further vascular filter 260 according to the invention, which is similar to the vascular filter 250 of FIGS. 77 and 78, and similar elements in FIG. 79 are assigned the same reference numerals.

In this case the support hoop 261 is provided in the form of a mesh or trellis 262. The mesh/trellis 262 comprises a number of openings 263 therethrough.

The mesh design of FIG. 79 may employ a homogenous mesh, or a variable mesh, for example with larger openings closer to the wire 261. The mesh may be fabricated from a bio-resorbable material or may be metallic or a bio-stable polymer.

The wire 261 may have a spiral/helical shape memory. The wire 261 may overlap on the walls or be joined at the extremities of the trellis 262.

The filter 260 has a wind sock type design. The mesh 251 is bonded to the mural structure 261. The support hoop 261 may have a sinusoid form, or a spiral form, or a coil form.

The embolus diverting verse cava tiller may be concentric wife the embolus, or may be non concentric.

The invention is not limited to the embodiments hereinbefore described, with reference to the accompanying drawings, which may be varied in construction and detail.

What is claimed:

1. A vascular filter comprising:
   a circumferential support frame having a first end region and a second end region;
   a plurality of arms having first ends connected to one of the first and second end regions and second free ends; and
   a biodegradable or bio-absorbable connection element connecting the second free ends of the plurality of arms to define an apex, wherein the apex is disposed between the first end region and the second end region;
   wherein the plurality of arms are movable from a capturing configuration to an open configuration, wherein in the capturing configuration, the second ends of the arms are connected to one another at the apex by the connection element to define a filter region, wherein upon degradation or absorption of the connection element, the second ends of the plurality of arms move to the open configuration in which the second ends of the arms are spaced apart.

2. The vascular filter of claim 1, wherein when in the open configuration, the arms are adjacent the circumferential support frame.

3. The vascular filter of claim 1, wherein the arms define a generally conically shaped filter region.

4. The vascular filter of claim 1, wherein the arms are biased adjacent the support frame.

5. The vascular filter of claim 1, wherein the apex defines an opening.

6. The vascular filter of claim 1, wherein at least a portion of the support frame is a mesh defining a plurality of openings.

7. The vascular filter of claim 6, wherein the mesh is bio-resorbable.

8. The vascular filter of claim 6, wherein the connection element extends through openings in the second ends of the arms.

9. The vascular filter of claim 1, wherein the support frame and the plurality of arms are all formed as a single integral piece.

10. The vascular filter of claim 1, wherein the connection element extends through openings in the second ends of the arms.

11. The vascular filter of claim 1, wherein the connection element comprises a suture.

12. The vascular filter of claim 1, wherein the support frame includes at least one anchor extending radially outward from an outer surface of the support frame.

13. The vascular filter of claim 12, wherein the at least one anchor is bioabsorbable.

14. The vascular filter of claim 12, wherein the at least one anchor includes a plurality of anchors, wherein some of the anchors face the first end region and some of the anchors face the second end region.

15. A vascular filter, comprising:
   a circumferential support frame having a first end region and a second end region;
   a plurality of arms having first ends connected to one of the first and second end regions and second free ends; and
   a biodegradable or bio-absorbable connection element connecting the second free ends of the plurality of arms to define an apex;
   wherein the plurality of arms are movable from a capturing configuration to an open configuration, wherein in the capturing configuration, the second ends of the arms are connected to one another at the apex by the connection element to define a filter region, wherein upon degradation or absorption of the connection element, the second ends of the plurality of arms move to the open configuration in which the second ends of the arms are spaced apart;

wherein the support frame includes a distal circumferential hoop, a proximal circumferential hoop, and a plurality of struts connecting the distal and proximal circumferential hoops.

16. The vascular filter of claim 15, wherein at least one of the distal or proximal hoop extends in a crown or sinusoid wave pattern.

17. A vascular filter comprising:
an expandable circumferential support frame;
a plurality of arms having first ends connected to the support frame and second free ends; and
a biodegradable or bio-absorbable connection element connecting the second free ends of the plurality of arms to define an apex, wherein the apex is disposed between first and second end regions of the support frame;

wherein the plurality of arms are movable from a capturing configuration to an open configuration, wherein in the capturing configuration, the second ends of the arms are connected at the apex by the connection element to define a filter region, wherein upon degradation or absorption of the connection element, the second ends of the plurality of arms move to the open configuration in which the second ends of the arms are spaced apart.

18. The vascular filter of claim 17, wherein when in the open configuration, the arms are adjacent the circumferential support frame.

19. The vascular filter of claim 17, wherein the arms define a generally conically shaped filter region.

* * * * *